US011779217B2

(12) United States Patent
Rondoni et al.

(10) Patent No.: US 11,779,217 B2
(45) Date of Patent: Oct. 10, 2023

(54) SYSTEM AND METHOD FOR COLLECTING AND DISPLAYING DATA ACQUIRED FROM AN IMPLANTABLE THERAPY DEVICE USING A CONSUMER ELECTRONIC DEVICE

(71) Applicant: Inspire Medical Systems, Inc., Golden Valley, MN (US)

(72) Inventors: John Rondoni, Plymouth, MN (US); David Todd Dieken, Minneapolis, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 0 days.

(21) Appl. No.: 16/425,910

(22) Filed: May 29, 2019

(65) Prior Publication Data

US 2019/0365228 A1    Dec. 5, 2019

Related U.S. Application Data

(60) Provisional application No. 62/678,665, filed on May 31, 2018.

(51) Int. Cl.
*A61B 5/00* (2006.01)
*A61N 1/36* (2006.01)

(52) U.S. Cl.
CPC .......... *A61B 5/0031* (2013.01); *A61B 5/0022* (2013.01); *A61B 5/4815* (2013.01);
(Continued)

(58) Field of Classification Search
CPC ... A61B 5/0031; A61B 5/0022; A61B 5/4815; A61B 5/743; A61B 5/4848;
(Continued)

(56) References Cited

U.S. PATENT DOCUMENTS 8,438,041 B2   5/2013   Green, III et al.
8,509,882 B2   8/2013   Albert et al.
(Continued)

FOREIGN PATENT DOCUMENTS

EP    2540344        1/2013
EP    3767923 A1    1/2021
(Continued)

OTHER PUBLICATIONS

International Search Report and Written Opinion for PCT/US2019/034544, dated Oct. 15, 2019.

*Primary Examiner* — Ankit D Tejani
*Assistant Examiner* — Joshua Brendon Solomon
(74) *Attorney, Agent, or Firm* — Dicke, Billig & Czaja, PLLC

(57) ABSTRACT

A method comprises establishing communication between a therapy device implantable in a patient and a consumer electronic device operable by the patient. The method comprises controlling, by the consumer electronic device, a predetermined set of therapy device functions in response to patient inputs to the consumer electronic device. The method also comprises transmitting therapy data from the therapy device to the consumer electronic device. The method further comprises presenting therapy data on a display of the consumer electronic device.

34 Claims, 36 Drawing Sheets

(52) U.S. Cl.
CPC .......... *A61B 5/743* (2013.01); *A61N 1/36135* (2013.01); *A61N 1/36146* (2013.01)

(58) Field of Classification Search
CPC .............. A61B 5/6898; A61N 1/36135; A61N 1/36146; A61N 1/36038; A61N 1/36003; A61N 1/3605; A61N 1/362; A61N 1/3956; A61N 1/37235; A61N 1/37247; G16H 40/67
See application file for complete search history.

(56) References Cited

U.S. PATENT DOCUMENTS

| | | | |
|---|---|---|---|
| 8,655,451 | B2 | 2/2014 | Klosterman et al. |
| 9,839,786 | B2 | 12/2017 | Rondoni et al. |
| 2002/0128860 | A1 | 9/2002 | Leveque et al. |
| 2003/0208465 | A1 | 11/2003 | Yurko et al. |
| 2007/0213783 | A1* | 9/2007 | Pless .................. A61N 5/0622 607/42 |
| 2008/0091466 | A1 | 4/2008 | Butler et al. |
| 2008/0103572 | A1* | 5/2008 | Gerber ................ A61N 1/0558 607/116 |
| 2008/0119705 | A1 | 5/2008 | Patel et al. |
| 2009/0024187 | A1* | 1/2009 | Erickson ........... A61N 1/37247 607/59 |
| 2009/0281590 | A1* | 11/2009 | Maskara ........... A61N 1/36843 607/25 |
| 2010/0049008 | A1* | 2/2010 | Doherty .............. A61B 5/0476 600/301 |
| 2012/0095528 | A1 | 4/2012 | Miller, III et al. |
| 2012/0277543 | A1 | 11/2012 | Homchowdhury et al. |
| 2014/0032242 | A1 | 1/2014 | LaBorde et al. |
| 2014/0088994 | A1 | 3/2014 | Kroh |
| 2014/0257849 | A1 | 9/2014 | Richards |
| 2014/0350635 | A1 | 11/2014 | Strother et al. |
| 2015/0006201 | A1 | 1/2015 | Pait et al. |
| 2015/0065047 | A1 | 3/2015 | Wu et al. |
| 2015/0119741 | A1 | 4/2015 | Zigel et al. |
| 2015/0224307 | A1* | 8/2015 | Bolea .................. A61B 5/0036 607/42 |
| 2015/0342519 | A1 | 12/2015 | Zheng |
| 2015/0367137 | A1 | 12/2015 | Rosellini |
| 2016/0193468 | A1 | 7/2016 | Rondoni et al. |
| 2016/0306929 | A1 | 10/2016 | Butka et al. |
| 2017/0079580 | A1 | 3/2017 | Moore et al. |
| 2017/0119308 | A1 | 5/2017 | Fuh et al. |
| 2017/0203103 | A1* | 7/2017 | Levine ............... A61N 1/36053 |
| 2017/0216610 | A1 | 8/2017 | Yoder et al. |
| 2018/0028111 | A1* | 2/2018 | Waris ................. A61B 5/4815 |
| 2018/0064404 | A1* | 3/2018 | Zheng ................. G06F 19/00 |

FOREIGN PATENT DOCUMENTS

| | | |
|---|---|---|
| JP | 2002102362 A | 4/2002 |
| JP | 2012509155 A | 4/2012 |
| JP | 2016527057 A | 9/2016 |
| WO | 2008130801 | 10/2008 |
| WO | 2010059839 A2 | 5/2010 |
| WO | 2015021348 A2 | 2/2015 |
| WO | 2017027729 | 2/2017 |
| WO | 2017083480 | 5/2017 |
| WO | 2017184753 A1 | 10/2017 |
| WO | 2019174565 A1 | 9/2019 |

\* cited by examiner

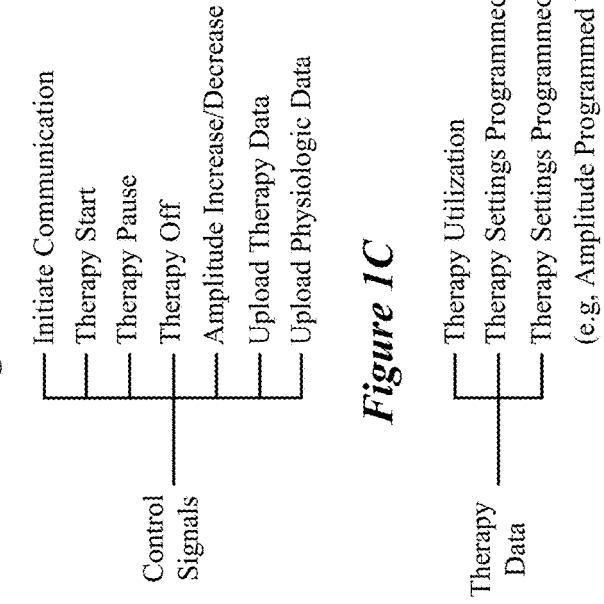
*Figure 1A*
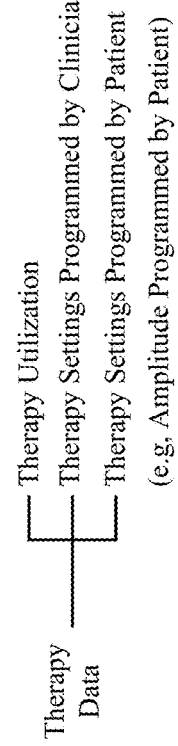
*Figure 1B*
*Figure 1C*
*Figure 1D*
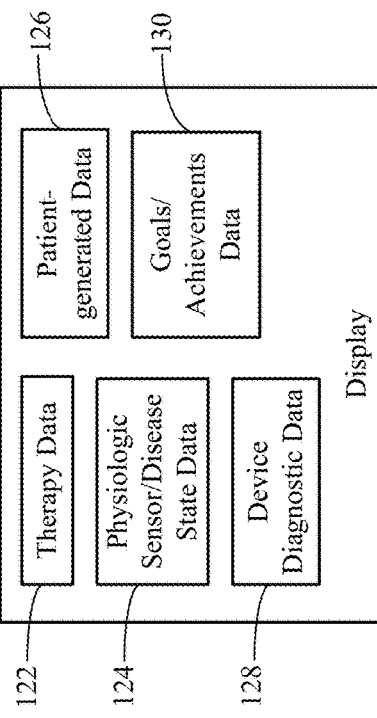
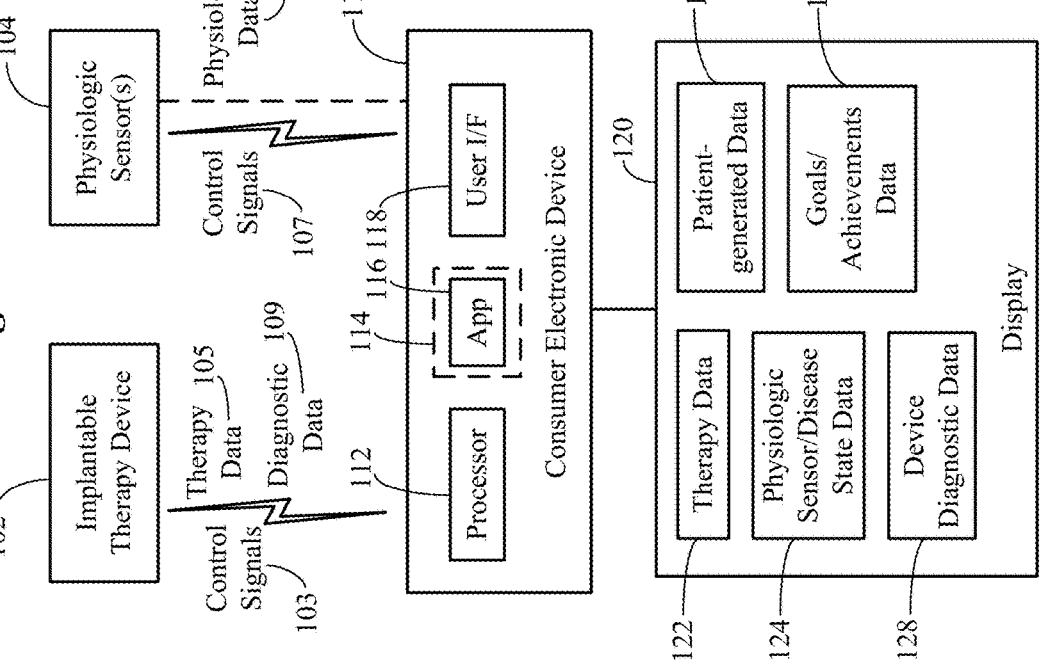

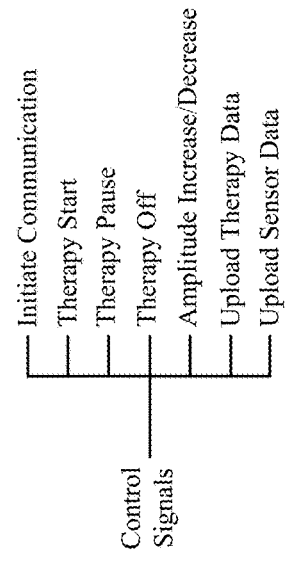
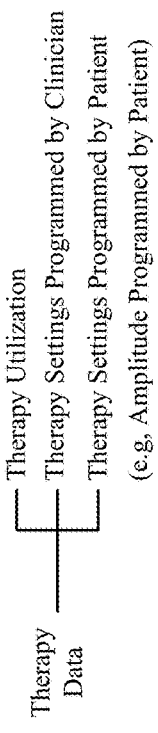
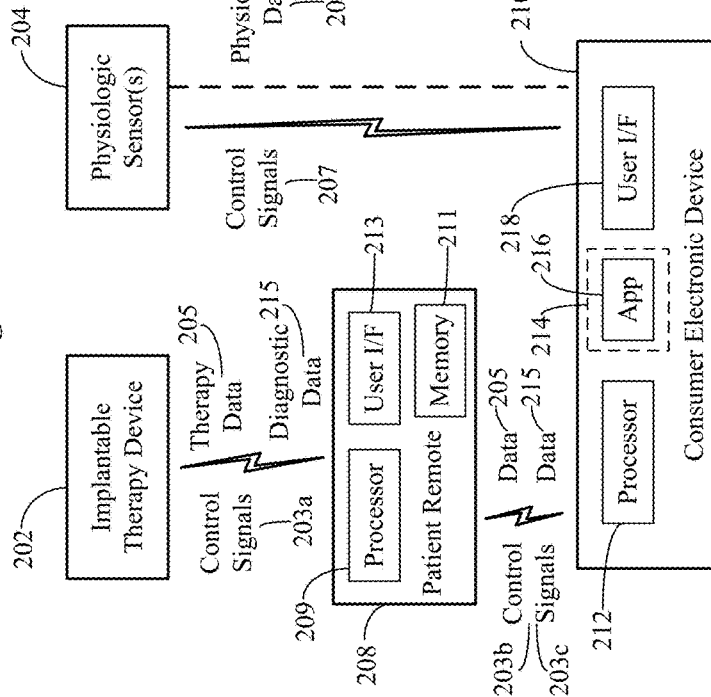
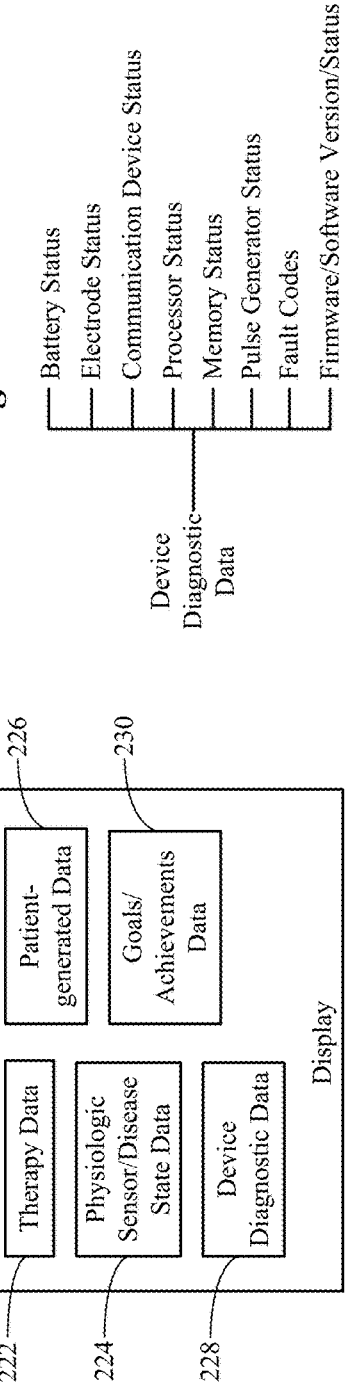

SYSTEM AND METHOD FOR COLLECTING AND DISPLAYING DATA ACQUIRED FROM AN IMPLANTABLE THERAPY DEVICE USING A CONSUMER ELECTRONIC DEVICE

RELATED PATENT DOCUMENTS

This application claims the benefit of Provisional Patent Application Ser. No. 62/678,665 filed on May 31, 2018, to which priority is claimed pursuant to 35 U.S.C. § 119(e), and which is incorporated herein by reference in its entirety.

SUMMARY

Embodiments are directed to a method comprising establishing communication between a therapy device implantable in a patient and a consumer electronic device operable by the patient. The method comprises controlling, by the consumer electronic device, a predetermined set of therapy device functions in response to patient inputs to the consumer electronic device. The method also comprises transmitting therapy data from the therapy device to the consumer electronic device. The method further comprises presenting therapy data on a display of the consumer electronic device.

Embodiments are directed to a method comprising establishing communication between a therapy device implantable in a patient and a patient remote operable by the patient. The method comprises controlling, by the patient remote, a predetermined set of therapy device functions in response to patient inputs to the patient remote. The method also comprises transmitting therapy data from the therapy device to the patient remote. The method further comprises transmitting the therapy data from the patient remote to a consumer electronic device. The method also comprises presenting therapy data on a display of the consumer electronic device.

Embodiments are directed to a system comprising a therapy device implantable in a patient and a consumer electronic device operable by the patient. The consumer electronic device is configured to control a predetermined set of therapy device functions in response to patient inputs to the consumer electronic device. The consumer electronic device is further configured to receive therapy data transmitted from the therapy device, and present the therapy data on a display of the consumer electronic device.

Embodiments are directed to a system comprising a therapy device implantable in a patient and a patient remote operable by the patient. The patient remote is configured to control a predetermined set of therapy device functions in response to patient inputs to the consumer electronic device. The patient remote is configured to receive therapy data transmitted by the therapy device. A consumer electronic device is operable by the patient and configured to communicate with the patient remote. The consumer electronic device is further configured to receive therapy data transmitted from the patient remote and present the therapy data on a display of the consumer electronic device.

The above summary is not intended to describe each disclosed embodiment or every implementation of the present disclosure. The figures and the detailed description below more particularly exemplify illustrative embodiments

BRIEF DESCRIPTION OF THE DRAWINGS

Throughout the specification reference is made to the appended drawings, where like reference numerals designate like elements, and wherein:

FIG. 1A illustrates a system for collecting and displaying patient data including data acquired from an implantable therapy device in accordance with various embodiments;

FIG. 1B shows various control signals that are communicated between a consumer electronic device and an implantable therapy device in accordance with various embodiments;

FIG. 1C shows various types of therapy data that are communicated from an implantable therapy device to a consumer electronic device in accordance with various embodiments;

FIG. 1D shows various types of device diagnostic data that are communicated from an implantable therapy device to a consumer electronic device in accordance with various embodiments;

FIG. 2A illustrates a system for collecting and displaying patient data including data acquired from an implantable therapy device in accordance with various embodiments;

FIG. 2B shows various control signals that are communicated between a consumer electronic device and an implantable therapy device in accordance with various embodiments;

FIG. 2C shows various types of therapy data that are communicated from an implantable therapy device to a consumer electronic device in accordance with various embodiments;

FIG. 2D shows various types of device diagnostic data that are communicated from an implantable therapy device to a consumer electronic device in accordance with various embodiments;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 3A:
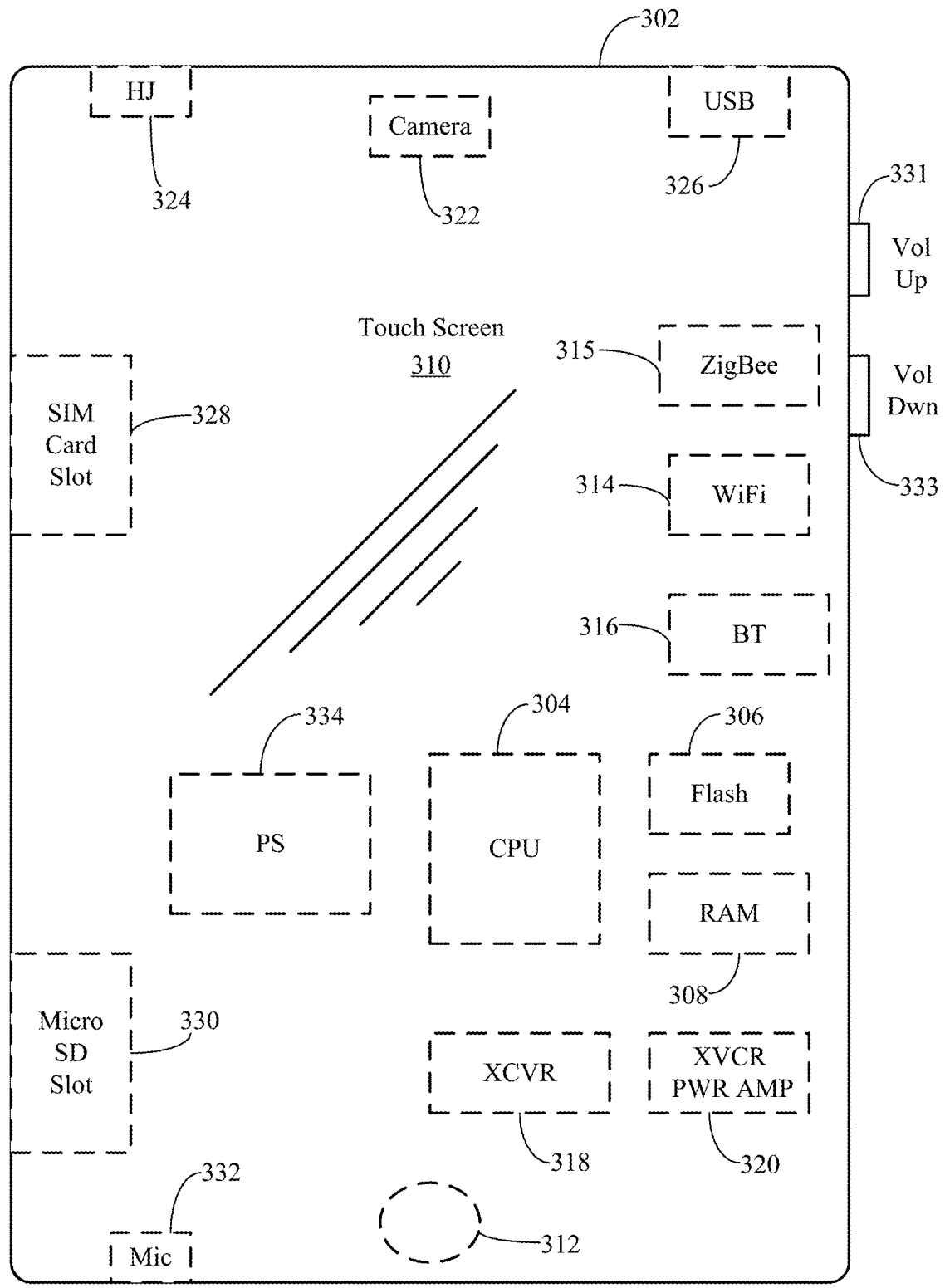
FIG. 3A illustrates a representative consumer electronic device configured to communicate with an implantable therapy device and/or a patient remote in accordance with various embodiments.

In the following description, reference is made to the accompanying set of drawings that form a part of the description hereof and in which are shown by way of illustration several specific embodiments. It is to be understood that other embodiments are contemplated and may be made without departing from the scope of the present disclosure. The following detailed description, therefore, is not to be taken in a limiting sense.

Many therapies involve patient choice, such as the patient needing to turn on or otherwise enable or change various therapy parameters. Therapies for which patient choice is involved are subject to patient adherence challenges. Clinicians lack insight into therapy utilization and outcomes when patients are out of the clinic and between visits. However, utilization and outcomes on a daily basis are more important to health outcomes than the acute assessments performed by clinicians during patient visits. Correlating utilization to objective and subjective therapy outcome measures is difficult for patients and clinicians. This challenge is further complicated due to the long periods between patient visits. Existing methods can display utilization and/or disease state metrics, but do not display correlation between the two in a way that is easy to understand. As such, desired patient action based on the information may not follow.

Embodiments of the disclosure are directed to collecting settings, utilization, and outcomes data directly from a therapeutic medical device. Embodiments of the disclosure combined device data with subjective and objective data sources to create a holistic clinical picture. Embodiments of the disclosure involve patient data collection on a patient's personal computing device and combining this data with subjective and objective outcomes.

The term "consumer electronic device" used herein encompasses a wide variety of devices that are not subject to medical regulatory body approval (e.g., FDA approval). Examples of a consumer electronic device include various portable (e.g., hand-held) computing and communication devices, such as a laptop, a notebook, a tablet, a phablet, a personal digital assistant, a cellular phone, and a smartphone. In some cases, the consumer electronic device can be a personal computer (PC). A consumer electronic device includes one or more communication devices that facilitate communication between the consumer electronic device and a medical device, such as a medical device subject to medical regulatory body approval. For example, the consumer electronic device can include one or more of a Bluetooth®, ZigBee®, or IEEE 802.11 compliant communication interface. The consumer electronic device can also include one or more communication devices that facilitate communication between the consumer electronic device and one or more physiologic sensors, monitoring devices, and/or personal health devices via a Bluetooth®, ZigBee®, IEEE 802.11, or ISO/IEEE 11073 compliant communication interface. The consumer electronic device may also include one or more communication devices that allow the consumer electronic device to communicate with public communication infrastructure (e.g., the Internet) and/or private communication infrastructure. For example, one or more communication devices can be configured to provide wireless communication via a GSM (Global System for Mobile Communications), CDMA (Code Division Multiple Access), GPRS (General Packet Radio Service) and/or HSDPA (High-Speed Downlink Packet Access) communication interface.

The term "app" used herein generally refers to a software application (e.g., program code) that is executed by a processor, such as a processor of a consumer electronic device. In some embodiments, an app refers to a software application executable by a processor of a mobile device, such as a laptop, a notebook, a tablet, a phablet, a personal digital assistant or a smartphone. Various app platforms exist for different operating systems, such as Apple iOS® platforms, Google Android® platforms, and Microsoft Windows® platforms. For example, an app of the present disclosure can be implemented to execute on smartphones such as the Apple iPhone® or Samsung Galaxy®, tablets such as the Apple iPad® or Google Nexus®, embedded devices executing the Google Android® operating system, and computer operating systems such as Apple Mac OS X® and Microsoft Windows 8®.

FIG. 1A illustrates a system for collecting and displaying patient data including data acquired from an implantable therapy device in accordance with various embodiments. The system shown in FIG. 1A includes an implantable therapy device 102 configured to deliver a therapy to a patient. Representative examples of the implantable therapy device 102 are described herein, including those shown in FIGS. 63A and 63B. The implantable therapy device 102 is configured to communicate with a consumer electronic device 110 via a wireless (e.g., radiofrequency) link. Among other components, the consumer electronic device 110 includes a processor 112, memory 114, an app 116 stored in the memory 114, and a user interface 118. The consumer electronic device 110 also includes a display 120, which can be a component of the user interface 118 (e.g., a touch screen). In some embodiments, the consumer electronic device 110 can be communicatively coupled to one or more physiologic sensors 104 via a wired link or a wireless link. The one or more physiologic sensors 104 can be coupled to or situated in proximity to the patient.

The processor 112 of the consumer electronic device 110, when executing program code of the app 116, is configured to communicate various control signals 103 to the implantable therapy device 102. For example, and with reference to FIG. 1B, the processor 112 can generate a control signal 103 to initiate communication between the implantable therapy device 102 and the consumer electronic device 110. Control signals 103 issued by the processor 112 can cause the processor of the implantable therapy device 102 to execute various patient-initiated functions in response to patient inputs to the user interface 118. For example, the processor 112 can generate control signals 103 to cause the implantable therapy device 102 to start therapy delivery, cause the implantable therapy device 102 to pause therapy delivery, and cause the implantable therapy device 102 to terminate therapy delivery. The processor 112 can generate control signals 103 to cause the implantable therapy device 102 to increase or decrease an amplitude or magnitude of therapy delivery (e.g., to increase or decrease stimulation amplitude) in response to patient inputs to the user interface 118. Other control signals 103 and corresponding device functions are contemplated, which will vary depending on the type and functionality of the implantable therapy device 102. In some embodiments, communication between the consumer electronic device 110 and the implantable therapy device 102 can be secured communication, such as in the manner disclosed in commonly-owned U.S. Provisional Application Ser. No. 62/203,435 (Rondoni et al.) filed Aug. 11, 2015, which is incorporated herein by reference.

The processor 112 of the consumer electronic device 110, when executing program code of the app 116, is configured to communicate various control signals 107 to one or more physiologic sensors 104. The processor 112 can generate control signals 107 to initiate communication between the consumer electronic device 110 and the one or more physiologic sensors 104. Control signals 107 issued by the processor 112 can cause a processor or controller of a physiologic sensor 104 to transmit physiologic data 106 from a memory of the physiologic sensor 104 to the memory 114 of the consumer electronic device 110. It is noted that various types of physiologic data 106 can be produced by the implantable therapy device 102, which can be received by the memory 114 of the consumer electronic device 110. It is also noted that the consumer electronic device 110 can include or incorporate one or more physiologic sensors 104. For example, a microphone of the consumer electronic device 110 can serve as a physiologic sensor 104, such as for monitoring patient respiration, respiratory sounds, and/or snoring.

Control signals 103 issued by the processor 112 of the consumer electronic device 110 can cause a processor of the implantable therapy device 102 to upload therapy data 105 from a memory of the implantable therapy device 102 to the memory 114 of the consumer electronic device 110. As is shown in FIG. 1C, the therapy data 105 can include therapy utilization, therapy settings programmed by the clinician, and therapy settings programmed by the patient. For example, the patient can use the user interface 118 to increase or decrease the stimulation amplitude of a therapy within a stimulation amplitude range pre-programmed by a clinician.

Control signals 103 issued by the processor 112 of the consumer electronic device 110 can cause the processor of the implantable therapy device 102 to transmit device diagnostic data 109 from the memory of the implantable therapy device 102 to the memory 114 of the consumer electronic device 110. For example, and with reference to FIG. 1D, the device diagnostic data 109 transmitted from the implantable therapy device 102 to the consumer electronic device 110 can include battery status, electrode status, communication device status, processor status, memory status, pulse generator status, fault codes, and firmware/software version/status.

The user interface 118 of the consumer electronic device 110 is configured to allow the patient to input patient-generated data into the memory 114 of the consumer electronic device 110. The patient-generated data represents subjective data concerning the health of the patient, such as general wellness and specific parameters such as tiredness level. The processor 112, executing program code of the app 116, can open a dialog box on the display 120 into which subjective health information can be input by the patient. The processor 112, executing program code of the app 116 or a separate app, can present a series of questions from a questionnaire or a clinician on the display 120 to be answered by the patient via the user interface 118. For example, the processor 112 in cooperation with the app 116 or a separate app can present an Epworth Sleepiness Scale (ESS) questionnaire on the display 120, requiring the patient to answer eight questions from which a sleepiness score is calculated by the processor 112.

The memory 114 of the consumer electronic device 110 aggregates patient medical data acquired from disparate sources, including the implantable therapy device 102, one or more physiologic sensors 104, and the patient himself or herself. The processor 112 cooperates with the display 120 of the consumer electronic device 110 to present various data stored in the memory 114. Preferably, the processor 112 and display 120 cooperate to present disparate types of patient medical data in close proximity on the display 120, which provides for visual correlation of the disparate data by the patient.

For example, therapy data 122 can be presented on the display 120 in close proximity to physiologic sensor data 124 to facilitate visual correlation between changes in a disease state indicated by the physiologic sensor data 124 in response to therapy delivered to the patient. By way of further example, therapy data 122 can be presented on the display 120 in close proximity to patient-generated data 126, which provides for visual correlation between therapy information and patient-subjective input (e.g., notes, questionnaire score). In another example, therapy data 122, patient-generated data 126, and goals/achievements data 130 can be presented in close proximity to one another on the display 120, which provides an indication of patient utilization and compliance with a therapy. In a further example, therapy data 122, patient-generated data 126, and physiologic sensor data 124 can be presented in close proximity to one another on the display 120, which provides visual correlation between changes in a disease state and patient-subjective input in response to therapy delivered to the patient.

FIG. 2A illustrates a system for collecting and displaying patient data including data acquired from an implantable therapy device in accordance with various embodiments. The system shown in FIG. 2A includes an implantable therapy device 202 configured to deliver a therapy to a patient. The implantable therapy device 202 is configured to communicate with a patient remote 208 via a wireless (e.g., radiofrequency, inductive) link. The patient remote 208 can be used by the patient to adjust various operating parameters and/or functions of the implantable therapy device 202. Among other components, the patient remote 208 includes a processor 209 coupled to memory 221 and a user interface 213. The processor 209, when executing program code of software stored in the memory 211, is configured to communicate various control signals 203a to the implantable therapy device 202. For example, and with reference to FIG. 2B, the processor 209 can generate a control signal 203a to initiate communication between the implantable therapy device 202 and the patient remote 208. Control signals 203a issued by the processor 209 can cause the processor of the implantable therapy device 202 to execute various patient-initiated functions in response to patient inputs to the user interface 213.

For example, the processor 209 of the patient remote 208 can generate control signals 203a to cause the implantable therapy device 202 to start therapy delivery, cause the implantable therapy device 202 to pause therapy delivery, and cause the implantable therapy device 202 to terminate therapy delivery. The processor 209 can generate control signals 203a to cause the implantable therapy device 202 to increase or decrease an amplitude (or magnitude) of therapy delivery (e.g., to increase or decrease stimulation amplitude) in response to patient inputs to the user interface 213. Other control signals 203a and corresponding device functions are contemplated, which will vary depending on the type and functionality of the implantable therapy device 202.

A control signal 203a issued by the processor 209 can cause a processor of the implantable therapy device 202 to upload therapy data 205 from a memory of the implantable therapy device 202 to the memory 211 of the patient remote 208. As is shown in FIG. 2C, the therapy data 205 can include therapy utilization, therapy settings programmed by the clinician, and therapy settings programmed by the patient. For example, the patient can use the user interface 213 to increase or decrease the stimulation amplitude of a therapy within a stimulation amplitude range pre-programmed by a clinician.

A control signal 203a issued by the processor 209 can cause the processor of the implantable therapy device 202 to transmit device diagnostic data 215 from the memory of the implantable therapy device 202 to the memory 211 of the patient remote 208. For example, and with reference to FIG. 2D, the device diagnostic data 215 transmitted from the implantable therapy device 202 to the patient remote 208 can include battery status, electrode status, communication device status, processor status, memory status, pulse generator status, fault codes, and firmware/software version/status.

The patient remote 208 is configured to communicate with a consumer electronic device 210 via a wireless (e.g., radiofrequency) link. Among other components, the consumer electronic device 210 includes a processor 212, memory 214, an app 216 stored in the memory 214, and a user interface 218. The consumer electronic device 210 also includes a display 220, which can be a component of the user interface 218 (e.g., a touch screen). The processor 212, when executing program code of the app 216, can communicate control signals 203c that are received and acted upon by the processor 209 of the patient remote 208. Similarly, the processor 209 of the patient remote 208 can communicate control signals 203b that are received and acted upon by the processor 212 of the consumer electronic device 210. For example, control signals 203b, 203c, can be communicated between the patient remote 208 and the consumer electronic device 212 to initiate communication between the two devices 208, 210.

In response to a patient input to the user interface 218 of the consumer electronic device 210, the processor 212 transmits a control signal 203c to cause the processor 209 of the patient remote 208 to transmit therapy data 205 to the processor 212 for storage in the memory 214. At the same time, or in response to a separate control signal 203c, device diagnostic data 215 is transmitted from the memory 211 of the patient remote 208 to the memory 214 of the consumer electronic device 210.

In some embodiments, the consumer electronic device 210 can be communicatively coupled to one or more physiologic sensors 204 via a wired link or a wireless link. The one or more physiologic sensors 204 can be coupled to or situated in proximity to the patient, and be configured to sense/monitor any of the physiologic signals or conditions discussed above. In some embodiments, the patient remote 208 can be configured to communicatively couple to the one or more physiologic sensors 204 via a wired link or wireless link. The processor 212 of the consumer electronic device 210, when executing program code of the app 216, is configured to communicate various control signals 207 to the one or more physiologic sensors 204. The processor 212 can generate control signals 207 to initiate communication between the consumer electronic device 210 and the one or more physiologic sensors 204. The processor 212 can generate control signals 207 to cause the one or more physiologic sensors 204 to upload physiologic data 206 to the memory 214 of the consumer electronic device 210. It is noted that various types of physiologic data 206 can be produced by the implantable therapy device 202, which can be received by the memory 214 of the consumer electronic device 210 via the patient remote 208. It is also noted that the consumer electronic device 210 can include or incorporate one or more physiologic sensors 204. For example, and as previously discussed, a microphone of the consumer electronic device 210 can serve as a physiologic sensor 204, such as for monitoring patient respiration, respiratory sounds, and/or snoring.

The user interface 218 of the consumer electronic device 210 is configured to allow the patient to input patient-generated data into the memory 214 of the consumer electronic device 210. The patient-generated data represents subjective data concerning the health of the patient, such as general wellness and specific parameters such as tiredness level. The processor 212, executing program code of the app 216, can open a dialog box on the display 220 into which subjective health information can be input by the patient. The processor 212, executing program code of the app 216 or a separate app, can present a series of questions from a questionnaire or a clinician on the display 220 to be answered by the patient via the user interface 218. For example, the processor 212 in cooperation with the app 216 or a separate app can present an Epworth Sleepiness Scale (ESS) questionnaire on the display 220, requiring the patient to answer eight questions from which a sleepiness score is calculated by the processor 212.

The memory 214 of the consumer electronic device 210 aggregates patient medical data acquired from disparate sources, including the implantable therapy device 202, the patient remote 208, the one or more physiologic sensors 204, and the patient himself or herself. The processor 212 cooperates with the display 220 of the consumer electronic device 210 to present various data stored in the memory 214. Preferably, the processor 212 and display 220 cooperate to present disparate types of patient medical data in close proximity on the display 220, which provides for visual correlation of the disparate data by the patient.

For example, therapy data 222 can be presented on the display 220 in close proximity to physiologic sensor data 224 to facilitate visual correlation between changes in a disease state indicated by the physiologic sensor data 224 in response to therapy delivered to the patient. By way of further example, therapy data 222 can be presented on the display 220 in close proximity to patient-generated data 226, which provides for visual correlation between therapy information and patient-subjective input (e.g., notes, questionnaire score). In another example, therapy data 222, patient-generated data 226, and goals/achievements data 230 can be presented in close proximity to one another on the display 220, which provides an indication of patient utilization and compliance with a therapy. In a further example, therapy data 222, patient-generated data 226, and physiologic sensor data 224 can be presented in close proximity to one another on the display 220, which provides visual correlation between changes in a disease state and patient-subjective input in response to therapy delivered to the patient.

The implantable therapy device 102, 202 represents a wide variety of implantable medical devices capable of delivering a therapy to the patient. For example, the implantable therapy device 102, 202 can be an implantable pulse generator, neurostimulator, cardiac pacemaker, resynchronizer, cardioverter/defibrillator, drug administration device (e.g., drug pump, external or implantable), diaphragm stimulator, bladder stimulator, cochlear implant, hearing aid, muscle stimulator or other type of stimulation device. The implantable therapy device 102, 202 and/or the one or more physiologic sensors 104, 204 can be configured to sense and monitor one or more of oxygen saturation (e.g., via a pulse oximeter), sleep stage, respiration, snoring, posture (e.g., sleeping position, such as left, right, prone, supine via an accelerometer), brain activity (e.g., electroencephalogram, EEG), muscle activity (e.g., electromyogram, EMG), glucose level, heart mechanical activity (e.g., heart sounds, seismocardiogram, SCG), heart electrical activity (electrocardiogram, ECG), heart rate, heart rate variability, blood pressure, temperature, and nerve activity.

Figure 63B:
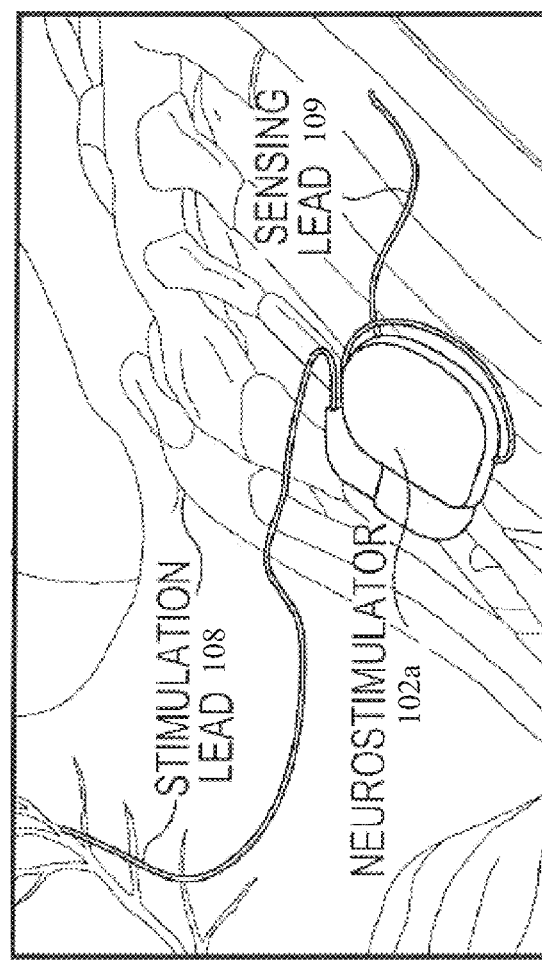
FIGS. 63A and 63B illustrate a representative therapy device implanted in a patient in accordance with various embodiments.
Figure 63A:
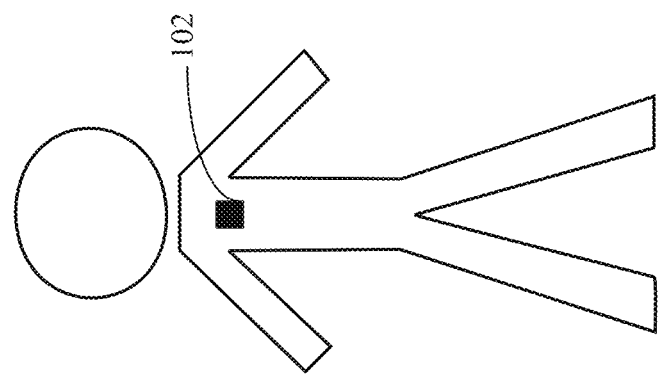

According to some embodiments, the implantable therapy device 102, 202 is a neurostimulation device configured to deliver a neurostimulation therapy for treating an obstructive disordered breathing condition, a representative example of which is shown implanted in a patient in FIG. 63B. In such embodiments, the neurostimulation device 102, 202 includes a neurostimulator 102a and a stimulation lead 108 that extends from the housing of the neurostimulator 102a to the hypoglossal nerve in the patient's neck. A sensing lead 109 extends from the housing of the neurostimulator 102a and is implanted at an intercostal muscle location of the rib cage. The sensing lead 109 detects intercostal muscle movement during patient respiration, signals from which are used to detect patient respiration. A pulse generator in the neurostimulator 102a provides electrical stimulation to the hypoglossal nerve via the stimulation lead based on detected patient respiration. A patient remote (e.g., patient remote 208) can communicate with the neurostimulator 102a and allow the patient to adjust a predetermined set of neurostimulator parameters and/or functions (e.g., therapy on, therapy pause, therapy off, amplitude increase, amplitude decrease). In some embodiments, the patient remote can be implemented to provide the functionality of the patient remote disclosed in commonly-owned U.S. Pat. No. 9,839,786 (Rondoni et al.) and U.S. Pat. Pub. No. 2016/0193468 (Rondoni et al.), each of which is incorporated herein by reference. The neurostimulator 102a can be implemented to provide the functionality of the neurostimulator disclosed in U.S. Pat. Pub. No. 2016/0193468 (Rondoni et al.).

FIG. 3A illustrates a representative consumer electronic device configured to communicate with an implantable therapy device and/or a patient remote in accordance with various embodiments. The consumer electronic device 302 is preferably a portable, hand-held computing and/or communication device that a patient uses on a daily basis. The consumer electronic device 302 shown in FIG. 3A can be representative of a smartphone, tablet, phablet, or other personal digital assistant.

The consumer electronic device 302 includes a processor (CPU) 304 coupled to flash memory 306 and RAM 308. Firmware and software executable by the consumer electronic device 302 is stored in the flash memory 306, then transferred to RAM 308 when executed by the CPU 304. The flash memory 306 preferably stores one or more apps that, when executed by the CPU 304, facilitate communication and interaction with an implantable therapy device and/or a patient remote in a manner described herein. The flash memory 306 also provide storage of the data acquired from the implantable medical device and one or more physiologic sensors, including therapy data, physiologic data, and device diagnostic data. Patient-generated data is also stored in the flash memory 306. A touchscreen 310 serves as an input/output user interface. One or more manual buttons 312 may be included to facilitate execution of various functions.

The consumer electronic device 302 includes a number of different radios, including a Wi-Fi® radio 312, a Bluetooth® radio 316, and a cellular radio 318. In some implementations, a ZigBee® radio 315 can also be included. The Bluetooth® radio 316 can provide communication via a standard Bluetooth® protocol or a low energy Bluetooth® (BLE) protocol. In some implementations, the cellular radio 318 is supplied power from a dedicated power amplifier 320. The cellular radio 318 can be configured to provide wireless communication in accordance with one or more protocols, including GSM, CDMA, GPRS and/or HSDPA. The consumer electronic device 302 can communicate with a network and/or the Internet via one or more of the radios 314, 315, 316, 318. For example, the consumer electronic device 302 can communicate data acquired from the implantable therapy device, one or more physiologic sensors, and patient-generated data input by the patient to a remote server via a network and/or the Internet. The remote server can be configured to process data received from the consumer electronic device 302, and the consumer electronic device 302 can access the processed data from the remote server.

The consumer electronic device 302 can also include a camera 322, a headphone jack 324, a USB interface 326, a SIM card slot 328, micro SD slot 330, and up and down volume controls 331, 333. A power supply 334 (battery and power management circuitry) provides power to the various components of the consumer electronic device 302.

A microphone 332 can be implemented to serve its normal function as an audio input device and, in some embodiments, serve as a physiologic sensor. For example, the consumer electronic device 302 can be situated near the patient's face, and the microphone 332 can be used to sense the patient's breathing, respiratory sounds, and snoring. One of the most common signs of obstructive sleep apnea is loud and chronic (ongoing) snoring. The microphone 322 can serve as a snoring sensor. A snoring tracking app (e.g., Snore Tracker app) stored in the flash memory 306 and executed by the CPU 304 can monitor a patient's snoring and produce snoring data for display on the touchscreen 310. The storing data represents objective disease state data which can be used to assess a breathing disorder, such as sleep apnea.

In some embodiments, the microphone 332 can be used as a data input sensor configured to receive sonic data from a patient remote. For example, the patient remote can include a sonic transceiver (e.g., piezoelectric or electromagnetic transducer, buzzer, speaker) which transmits sonic data to the microphone 332 of the consumer electronic device 302. In some embodiments, the sonic data is transmitted at a frequency above an audio range of normal human hearing (e.g., ultrasonic data). In other embodiments, the sonic data is transmitted at a frequency within the audio range of normal human hearing (e.g., <18-20 kHz), which allows the patient to effectively listen to the data transfer as an indicator of successful or unsuccessful communication between the consumer electronic device 302 and the patient remote. The sonic data can be transmitted using digital modulation (e.g., phase shift keying) of a high-frequency carrier. The consumer electronic device 302 can include a demodulator configured to demodulate sonic data transmitted using digital modulation. It is noted that, in some embodiments, an external microphone (wireless or wired) can be used as a snoring sensor. The external microphone can be communicatively coupled to the consumer electronic device 302 via a wireless (e.g., via Bluetooth® radio 316) or wired connection (e.g., USB).

Figure 3B:
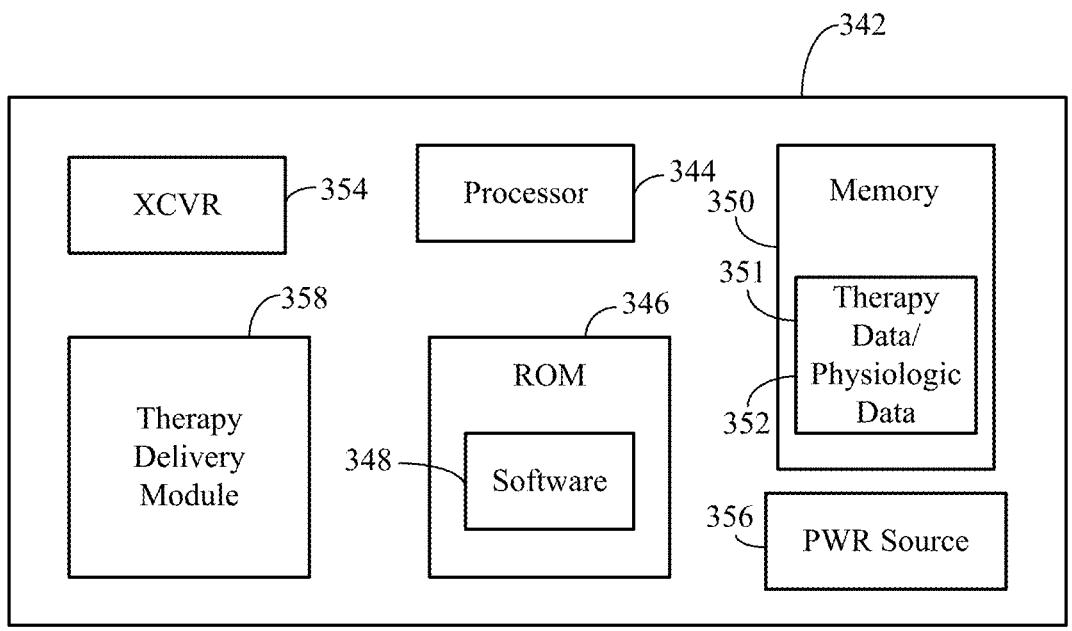
FIG. 3B illustrates a representative implantable therapy device configured to deliver a therapy to a patient and to produce therapy data and physiologic data associated with the patient in accordance with various embodiments.

FIG. 3B illustrates a representative implantable therapy device configured to deliver a therapy to a patient and to produce therapy data and physiologic data associated with the patient in accordance with various embodiments. The implantable therapy device 342 includes a processor 344 coupled to memory 346, 350. The processor 344 can be a microprocessor, an embedded microprocessor, an embedded controller, or a digital signal processor (DSP), for example. The processor 344 is configured to execute program code stored as software 348 in a read-only memory (ROM) 346. The program code, when executed by the processor 344, causes the processor 344 to implement the various therapy device functions described herein. The processor 344 cooperates with memory 350 (e.g., flash, SRAM) to store therapy data 351 generated by/stored in the implantable therapy device 342 and physiologic data 352 generated by one or more sensors of the implantable therapy device 342. A power source 356, which can be rechargeable, provides power to the various components of the implantable therapy device 342. The implantable therapy device 342 includes a therapy delivery module 358. The therapy delivery module 358 can include a pulse generator coupled to an electrode arrangement, for example. A transceiver 354 is configured to facilitate wireless communication between the implantable therapy device 342 and another device or system (e.g., patient remote, consumer electronic device) via any of the devices/protocols disclosed herein. Therapy data 351 and physiologic data 352 stored in the memory 350 can be transmitted to another device or system via the transceiver 354.

Figure 3C:
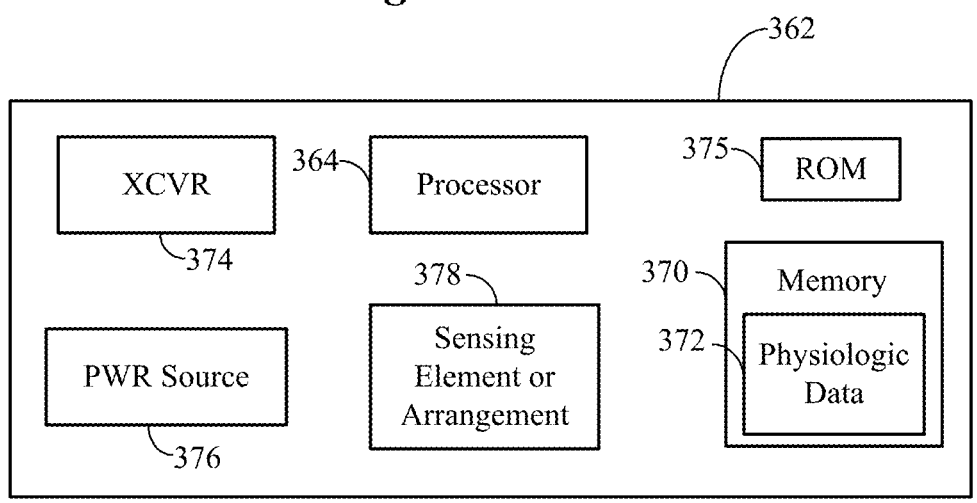
FIG. 3C illustrates a representative physiologic sensor configured to produce sensor data associated with a particular patient in accordance with various embodiments.

FIG. 3C illustrates a representative physiologic sensor configured to produce sensor data associated with a particular patient in accordance with various embodiments. The physiologic sensor 362 includes a processor 364 coupled to a memory 370. The processor 364 can be a microprocessor, an embedded microprocessor, an embedded controller, a digital signal processor, an ASIC, a field programmable gate array, or a programmable logic device, for example. In some embodiments, the processor 364 is configured to execute program code stored as software in a nonvolatile memory 375 (e.g., ROM) to implement the various physiologic sensor functions described herein. The processor 364 cooperates with memory 370 (e.g., flash, SRAM) to store physiologic data 372 acquired by a sensing element or arrangement 378. A power source 376, which can be rechargeable, provides power to the various components of the physiologic sensor 362.

The physiologic sensor 362 includes a transceiver 374 which can be configured to facilitate wired or wireless communication with another device or system (e.g., consumer electronic device, patient remote) via any of the devices/protocols disclosed herein. In some embodiments, the transceiver 374 is configured to facilitate communication between the physiologic sensor 362 and a network or the Internet via a router and/or modem. In such embodiments, physiologic data 372 can be communicated to another device or system (e.g., consumer electronic device, patient remote, remote server) via the network or the Internet. In other embodiments, the transceiver 374 is configured to facilitate communication between the physiologic sensor 362 and a transceiver of another device or system (e.g., consumer electronic device, patient remote), which in turn can transmit the physiologic data 372 to a remote server or other remote device/system via a network or the Internet.

Figure 3D:
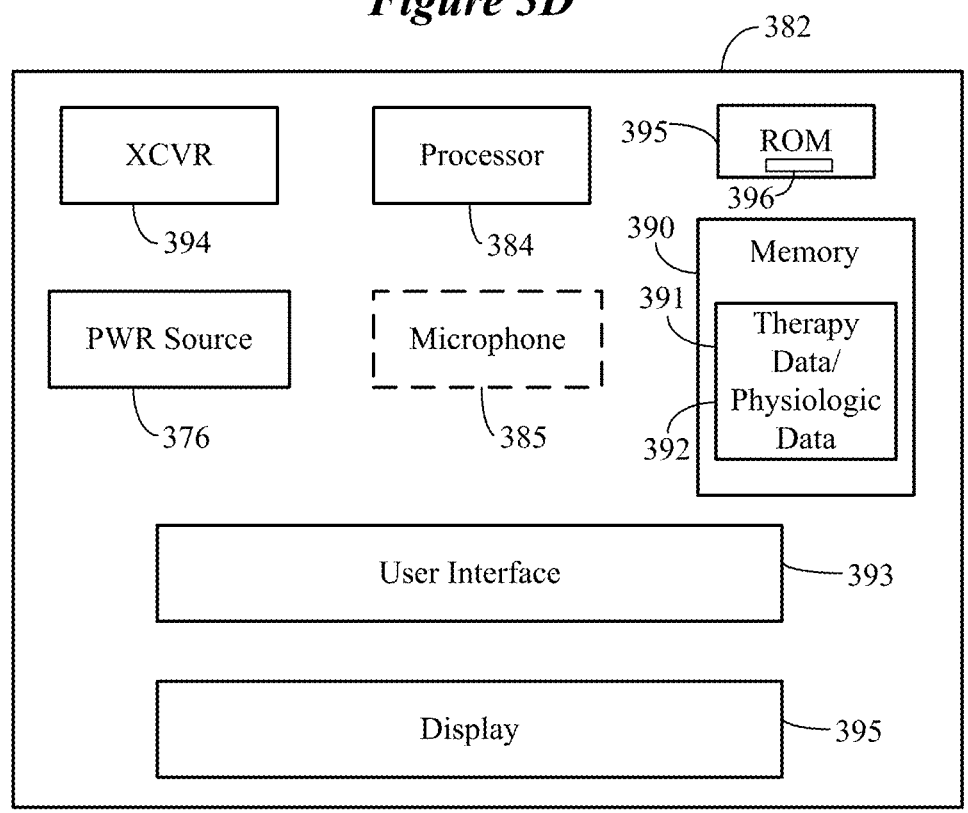
FIG. 3D illustrates a representative patient remote configured to wirelessly communicate with an implantable therapy device in accordance with various embodiments.

FIG. 3D illustrates a representative patient remote configured to wirelessly communicate with an implantable therapy device in accordance with various embodiments. The patient remote 382 includes a processor 384 coupled to memory 390, 395. The processor 384 can be a microprocessor, an embedded microprocessor, an embedded controller, or a digital signal processor (DSP), for example. The processor 384 is configured to execute program code stored as software 396 in a read-only memory (ROM) 395. The program code, when executed by the processor 384, causes the processor 384 to implement the various patient remote functions described herein.

A transceiver 394 is configured to facilitate wireless communication between the patient remote 382 and an implantable therapy device via any of the devices/protocols disclosed herein. The transceiver 394 is also configured to facilitate wireless communication between the patient remote 382 and another device or system (e.g., consumer electronic device, network, the Internet, remote server) via any of the devices/protocols disclosed herein. Although shown as a single component, it is understood that the transceiver 394 can represent two or more transceivers, each of which can be configured to implement a different communication protocol. In some embodiments, the transceiver 394 is configured to communicate with one or more physiologic sensors coupled to or situated in proximity to a patient. Sensor data acquired by the one or more physiologic sensors can be stored as physiologic data 392 in the memory 390.

The processor 384 cooperates with memory 390 (e.g., flash, SRAM) to store therapy data 391 generated by/stored in an implantable therapy device and physiologic data 352 generated by one or more sensors of the implantable therapy device (and optionally by one or more additional physiologic sensors). Therapy data 391 and physiologic data 392 stored in the memory 390 can be transmitted to another device or system (see examples above) via the transceiver 394. A power source 376, which can be rechargeable, provides power to the various components of the patient remote 382. In some embodiments, the patient remote 382 can include a microphone 385, which can serve as a respiration sensor for sensing and monitoring patient respiration and respiratory disturbances, such as patient snoring. Snoring data can be stored in the memory 390 as physiologic data 392.

Figure 3E:
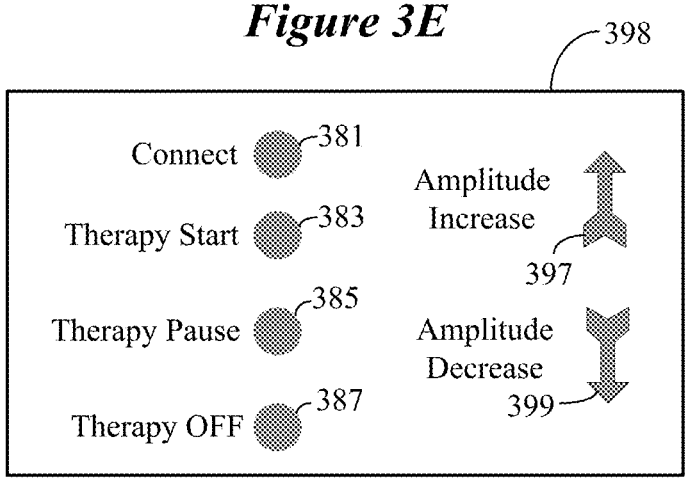
FIG. 3E is a representative set of patient controls that can be implemented by the patient remote shown in FIG. 3D.

The patient remote 382 also includes a user interface 393 and a display 395. In some embodiments, the user interface 393 includes a number of manually-actuated buttons, such as mechanical or capacitive buttons. In such embodiments, the display 395 can be a standard display (e.g., LED, OLED, LCD, E-ink). In other embodiments, the display 395 is implemented as a touchscreen, which can serve as the user interface 393, exclusively or in combination with one or more manually-actuated buttons. FIG. 3E is a representative set of patient controls 398 that can be implemented by the user interface 393 and/or the display 395. The patient controls 398 include a connect control 381, which, when actuated by a patient, causes the processor 384 and transceiver 394 to initiate communication with an implantable therapy device. Actuation of the connect control 381 can also facilitate communication between the patient remote 382 and another system or device, such as a consumer electronic device. The patient controls 398 also included a therapy start button 383, a therapy pause button 385, and a therapy OFF button 387, which respectively cause the implantable therapy device to start therapy delivery (sometimes after a predetermined start delay, such as 15 minutes), pause therapy delivery, and terminate therapy delivery. An amplitude increase button 397 and an amplitude decrease button 399, when actuated by the patient, respectively causes the implantable therapy device to increase and decrease the amplitude or magnitude of the delivered therapy. For example, the amplitude of a neurostimulation therapy delivered by the implantable therapy device can be increased or decreased via the amplitude increase 397 and amplitude decrease 399 buttons.

Figure 4A:
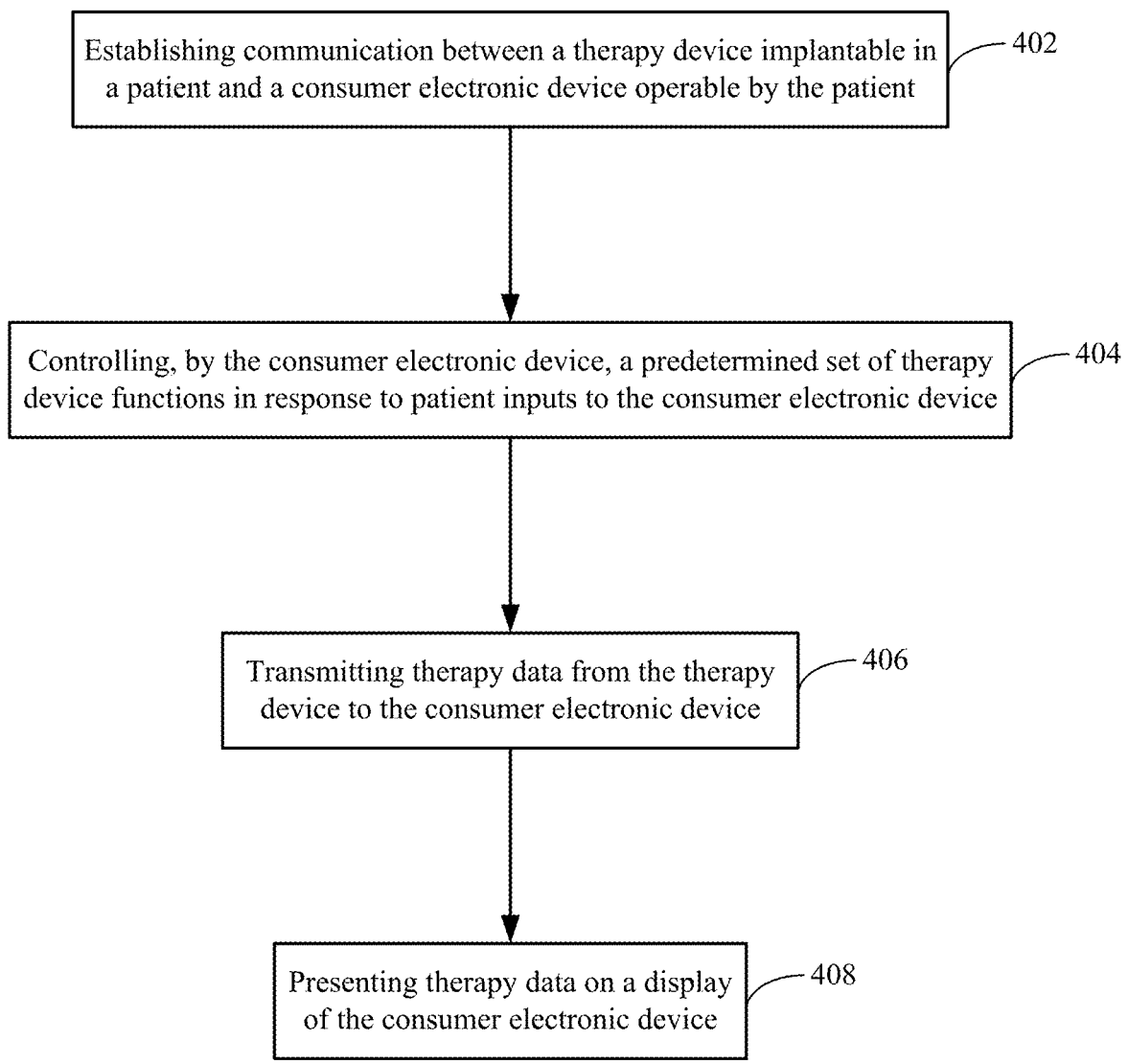
FIG. 4A illustrates a method of acquiring data from an implantable therapy device and displaying the data using a consumer electronic device operated by a patient in accordance with various embodiments.

FIG. 4A illustrates a method of acquiring data from an implantable therapy device and displaying the data using a consumer electronic device operated by a patient in accordance with various embodiments. The method shown in FIG. 4A involves establishing 402 communication between a therapy device implantable in a patient and a consumer electronic device operable by the patient. The method involves controlling 404, by the consumer electronic device, a predetermined set of therapy device functions in response to patient inputs to the consumer electronic device. The method also involves transmitting 406 therapy data from the therapy device to the consumer electronic device. In some embodiments, physiologic data produced by the therapy device is transmitted along with the therapy data to the consumer electronic device. The method further involves presenting 408 therapy data on a display of the consumer electronic device. In some embodiments, physiologic data and therapy data are presented on the display of the consumer electronic device. In further embodiments, patient-generated data is input to the consumer electronic device by the patient. The patient-generated data, therapy data, and optionally the physiologic data can be presented on the display of the consumer electronic device.

Figure 4B:
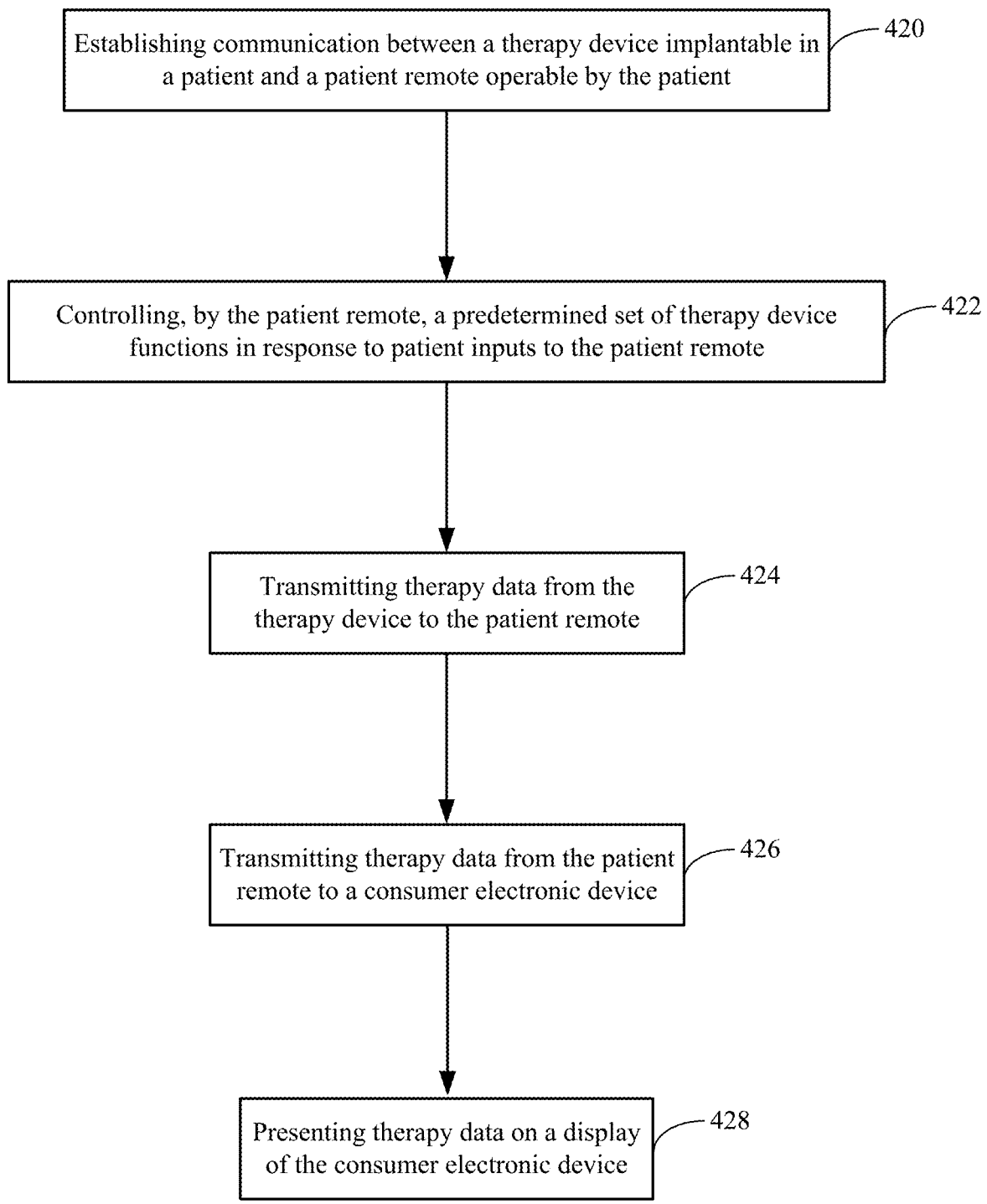
FIG. 4B illustrates a method of acquiring data from an implantable therapy device using an intermediate device operated by a patient, and presenting the data using a consumer electronic device operated by the patient in accordance with various embodiments.

FIG. 4B illustrates a method of acquiring data from an implantable therapy device using an intermediate device operated by a patient, and presenting the data using a consumer electronic device operated by the patient in accordance with various embodiments. The method shown in FIG. 4B involves establishing 420 communication between a therapy device implantable in a patient and a patient remote operable by the patient. The method involves controlling 422, by the patient remote, a predetermined set of therapy device functions in response to patient inputs to the patient remote. The method also involves transmitting 424 therapy data from the therapy device to the patient remote. In some embodiments, physiologic data produced by the therapy device is transmitted along with the therapy data to the patient remote. The method further involves transmitting 426 therapy data from the patient remote to a consumer electronic device. In some embodiments, physiologic data produced by the therapy device and the therapy data are transmitted from the patient remote to the consumer electronic device. The method also involves presenting 428 therapy data on a display of the consumer electronic device. In some embodiments, physiologic data and therapy data are presented on the display of the consumer electronic device. In further embodiments, patient-generated data is input to the consumer electronic device by the patient. The patient-generated data, therapy data, and optionally the physiologic data can be presented on the display of the consumer electronic device.

Figure 5:
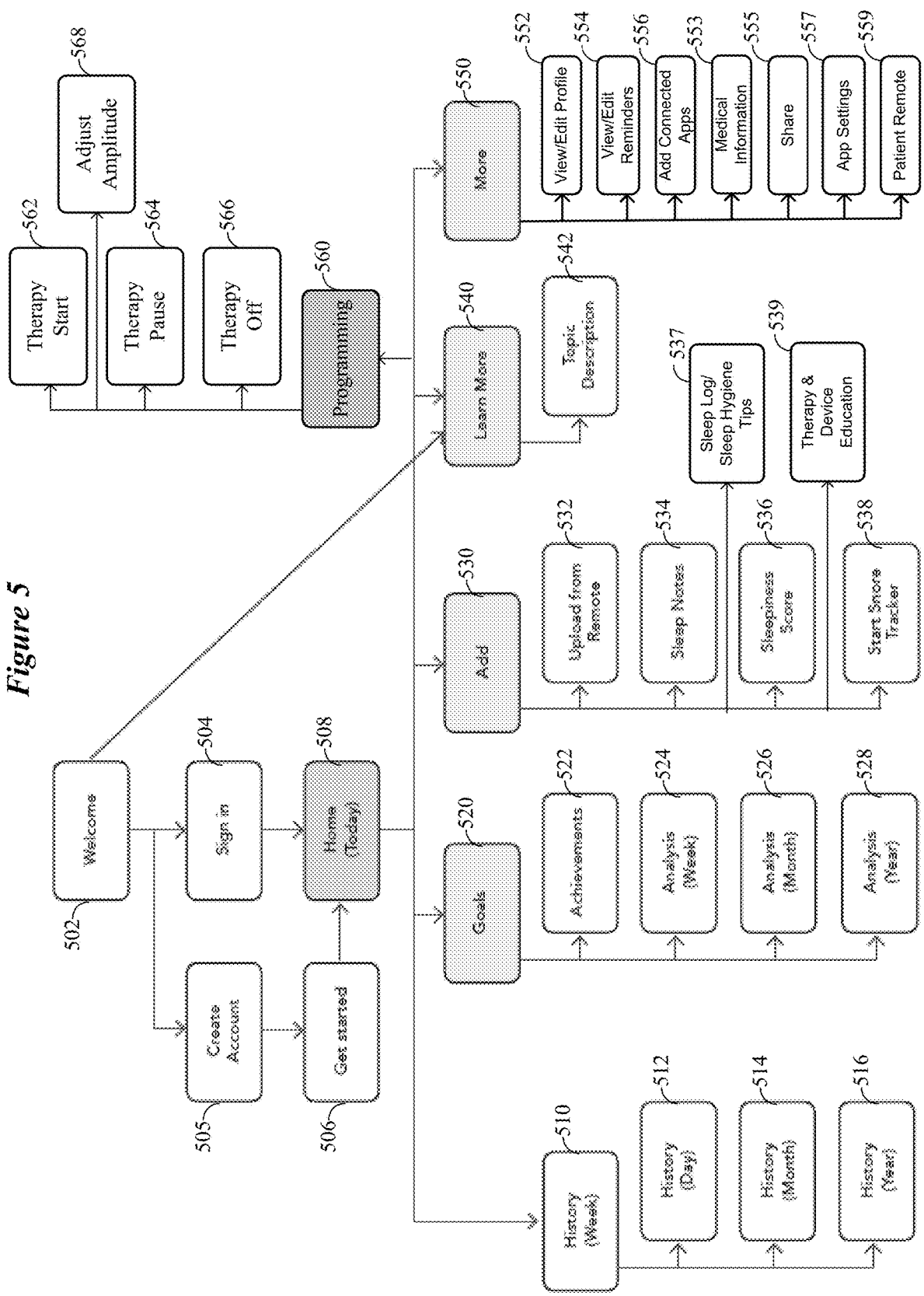
FIG. 5 is a high-level site map of various screens and functions implemented by a consumer electronic device configured to receive and process therapy data acquired from an implantable therapy device in accordance with various embodiments.

FIG. 5 is a high-level site map of various screens and functions implemented by a consumer electronic device configured to receive and process therapy data acquired from an implantable therapy device in accordance with various embodiments. The consumer electronic device is preferably a smartphone, phablet or tablet configured to execute a mobile app that causes a processor of the consumer electronic device to generate screen images and perform functions associated with the screens shown in FIGS. 5-61. For purposes of illustration, and not of limitation, the screens shown in FIGS. 5-61 and associated processes are carried out by a smartphone used by a patient. Also for purposes of illustration, and not of limitation, the therapy data stored in and processed by the patient's smartphone is therapy data acquired from a neurostimulator configured to deliver a neurostimulation therapy for treating an obstructive disordered breathing condition of the patient. Other data is acquired and processed by the patient's smartphone, including patient-generated data (e.g., sleep log data) and physiologic sensor data (e.g., snoring data) which provides insight into a disease state of the patient (e.g., sleep apnea).

Figure 6:
FIGS. 6-61 are screens presented on a display of a consumer electronic device in accordance with an app executed by a processor of the consumer electronic device according to various embodiments.
Figure 10:
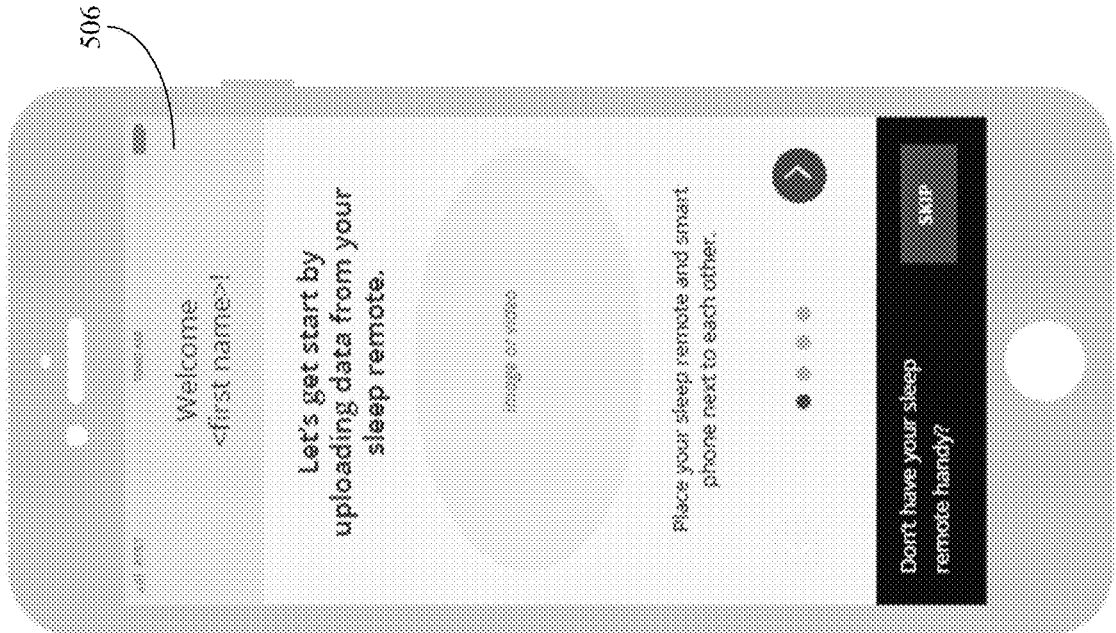

Execution of the app is initiated by the patient tapping on the app icon presented on the touch screen of the patient's smartphone. The patient is initially presented with a Welcome screen 502, an example of which is shown in FIG. 6. From the Welcome screen 502, the patient can jump to a Learn More screen 540, shown in FIG. 7, a Create Account screen 505, shown in FIG. 9, or a Sign In screen (similar to screen 505 in FIG. 9, but requesting email address and password). If the patient needs to create a new account, it can be assumed that no therapy and related data for the patient is available in the smartphone. As such, the patient is directed to a Get Started screen 506, which is shown in FIG. 10, after which the patient is directed to a Home screen 508. If the patient has an account, the patient is directed to the Sign In screen. After signing in, the patient is presented with the Home screen 508, which is a default view of patient information for the current date (Today). Different versions of the Home screen 508 are shown in FIGS. 12-18. Differences in the Home screen 508 result from the availability or absence of different data available for presentation.

From the Home screen 508, the patient can jump to different screens, including History screens 510-516, Goals screens 520-528, Add Data screens 530-538, Learn More screens 540-542, More screens 550-556, and Programming screens 560-568. History screens 510 (week), 512 (Day), 514 (month), and 516 (Year) present therapy data and other patient-related data for each of these spans of time. The Goals screens 520-528 include a Goal Summary screen 520, an Achievements Summary screen 522, and Goal/Achievement analysis screens for different spans of time, including screens 524 (week), 526 (month), and 528 (year). The Add Data screens 530-538 include a Data Upload screen 532, a Sleep Notes screen 534, a Sleepiness Score screen 536, and a Start Snore Tracker screen 538. The Learn More screens include Learn More screen 540 and Learn More Topic screen 542. The More screens include a More screen 550, Profile screen 552, a Reminders screen 554, and an Add Connected Apps screen 556.

Figure 8:
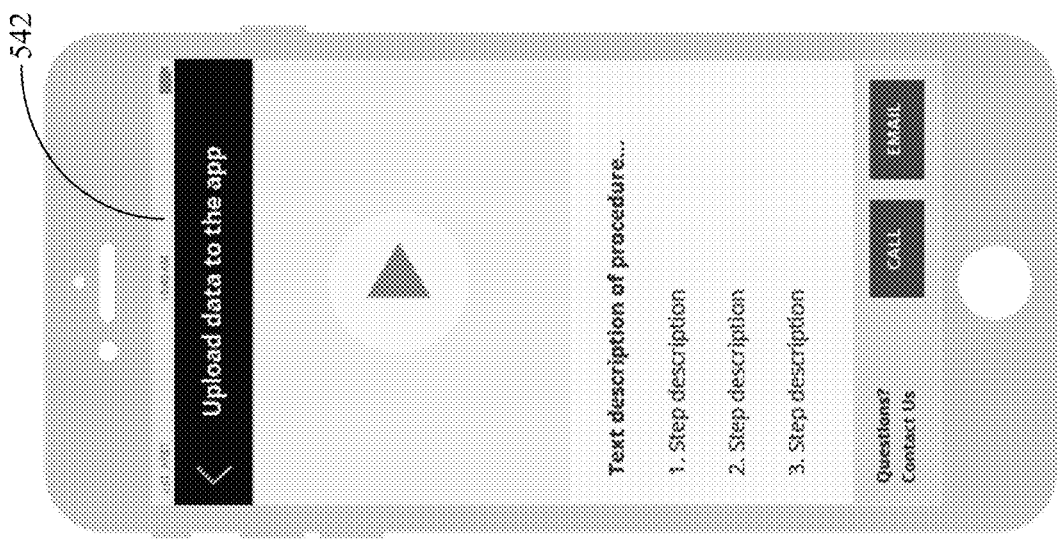
Figure 7:
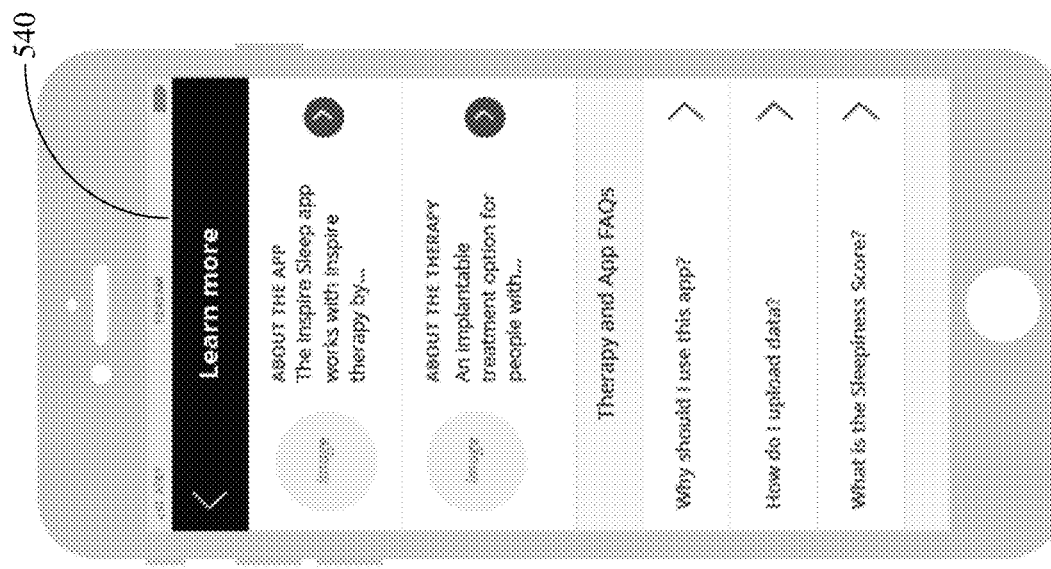
Figure 9:
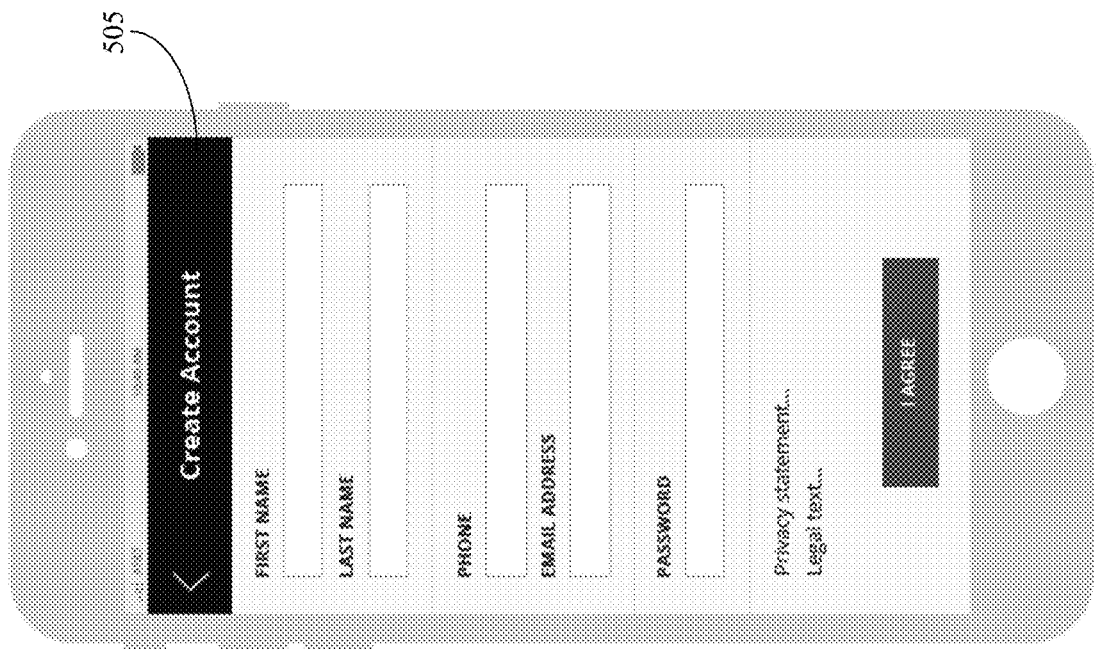

The following discussion describes many of the screens shown in site map of FIG. 5. For example, FIG. 6 shows the Welcome screen 502, which allows the patient to jump to the Learn More screen 540, Create Account screen 505, or the Sign In screen 504. FIG. 7 shows the Learn More screen 540, which provides the patient with more information on the app and the therapy being delivered to the patient (e.g., detailed information and FAQs). FIG. 8 shows a Learn More Topic screen 542, which allows the patient to input a specific question to the app (e.g., How do I upload data to the app?). The answer to the patient's question can be presented as text only, text and images, videos, or combination of these outputs. The answer can also include links to one or more websites outside of the app. FIG. 9 shows the Create Account screen 505, which allows the patient to create an account using the patient's first name, last name, phone number, email address, and a password.

FIG. 10 shows the Get Started screen 506, which provides patient instructions for uploading data to the app. In the embodiment shown in FIG. 10, the Get Started screen 506 instructs the patient to place the smartphone next to the patient remote (referred to herein as a sleep remote). As was discussed previously, the patient remote includes a memory that stores therapy data and physiologic data acquired from the patient's implantable therapy device. Actuation of an upload button (not shown) presented on the smartphone's screen initiates the upload of data from the patient remote to the patient's smartphone (e.g., via a radiofrequency link). In some embodiments, and as previously discussed, the smartphone is configured to acquire therapy and physiologic data directly from the implantable therapy device. In such embodiments, one or more screens are presented on the display of the smartphone that provide instructions for uploading data directly to the smartphone. In either of these embodiments, the status of the uploading process is presented on an Upload screen 532. For example, the patient will receive a confirmation that the data is being uploaded and a subsequent confirmation that the data upload was successfully completed. It is noted that Upload screens similar to screens 506 and 532 are presented when uploading data via the Add Data screen 530.

Figure 12:
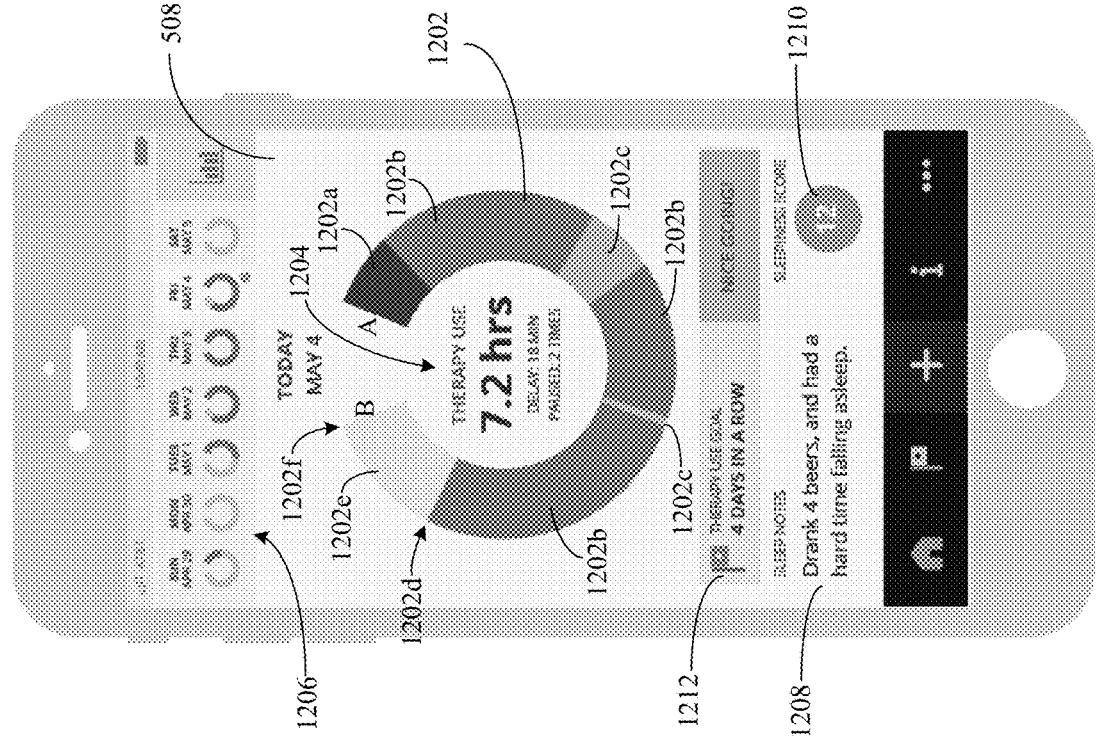

FIG. 12 shows the Home screen 508, which is a default view of data for Today's date (e.g., May 4$^{th}$). The Home screen 508 includes a graph icon 1202 which, in this illustrative example, depicts therapy utilization data for the patient on May 4$^{th}$ in the form of a stacked bar graph. The stacked bar graph 1202 is presented in an open ring configuration. One end of the open ring graph 1202, denoted end A, defines the start of therapy use by the patient. The other end of the open ring graph 1202, denoted end B, defines the end of therapy as defined by a target therapy duration established by a clinician. The total duration between ends A and B represents the target therapy duration established for the patient. In this illustrative example, the target therapy duration is 8.0 hours.

The stacked bar graph 1202 indicates the duration of each of a number of different phases of therapy utilization in temporal order. The different phases include a start delay 1202a, a therapy ON phase 1202b, a therapy pause phase 1202c, and a therapy OFF phase 1202d. Each of these phases can be denoted by a different color or a different hatching pattern in the stacked bar graph 1202. The start delay 1202a is typically programmed by the patient's clinician, while the therapy ON, pause, and OFF phases 1202b, 1202c, 1202d are controlled by the patient (in response to patient inputs to the patient remote or to patient controls presented on the display of the smartphone). For the stacked bar graph 1202 shown in FIG. 12, it can be seen that a first duration of therapy 1202b was delivered to the patient after the start delay 1202a, followed by a first pause duration 1202c and a second duration of therapy 1202b. After the second duration of therapy 1202b, the patient initiated a second pause duration 1202c, followed by a third duration of therapy 1202b. The patient terminated the therapy 1202d by initiating a therapy OFF command prior to reaching the target therapy duration 1202f. The duration 1202e represents the duration of time between the therapy OFF phase 1202d and the target therapy duration 1202f. In this illustrative example, the therapy utilization by the patient for May 4$^{th}$ was 7.2 hours, the start delay 1202a was 18 minutes, and there were a total of 2 pause events. This data 1204 is presented in textual form in the middle of the open ring stacked bar graph 1202.

The home screen 508 includes a top banner that displays the days of the current week and an open ring stacked bar graph 1202 for each of the days of the current week. It is noted that the patient can swipe to the left or to the right in order to select another day. Also, tapping the graph icon 1202 opens a History screen, the default of which is a week view of patient utilization data and other related data (see, e.g., FIGS. 28-30). The home screen 508 can further include therapy use goals and/or achievements 1212. Goals and achievements serve to motivate and reward patient compliance with a therapy.

Figure 14:
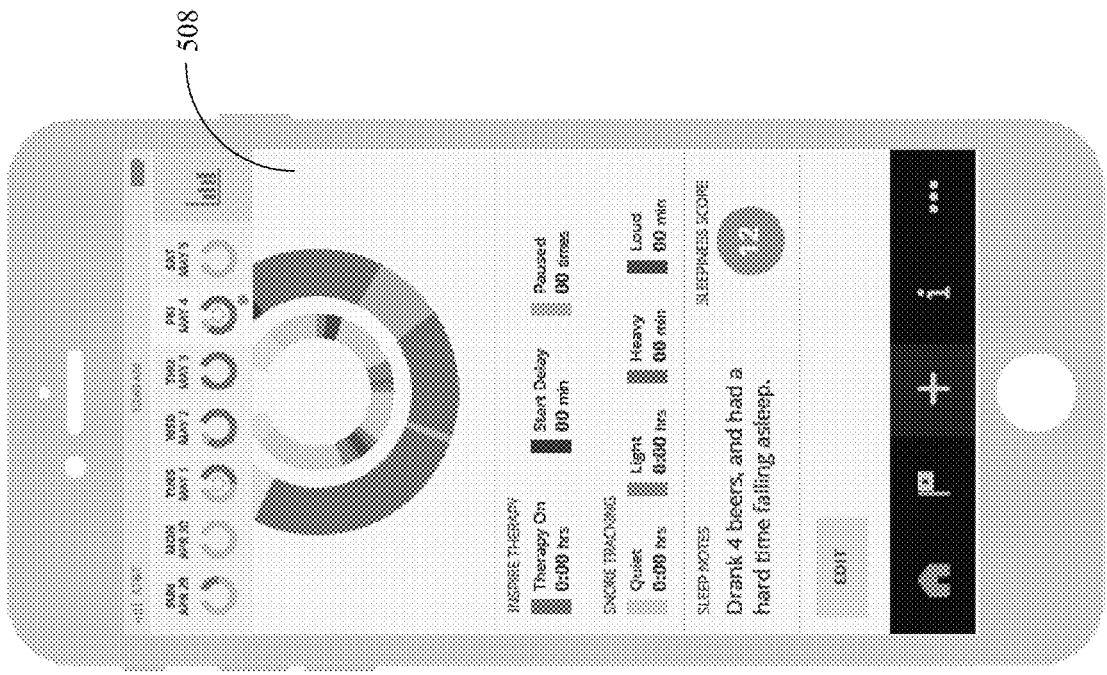
Figure 16:
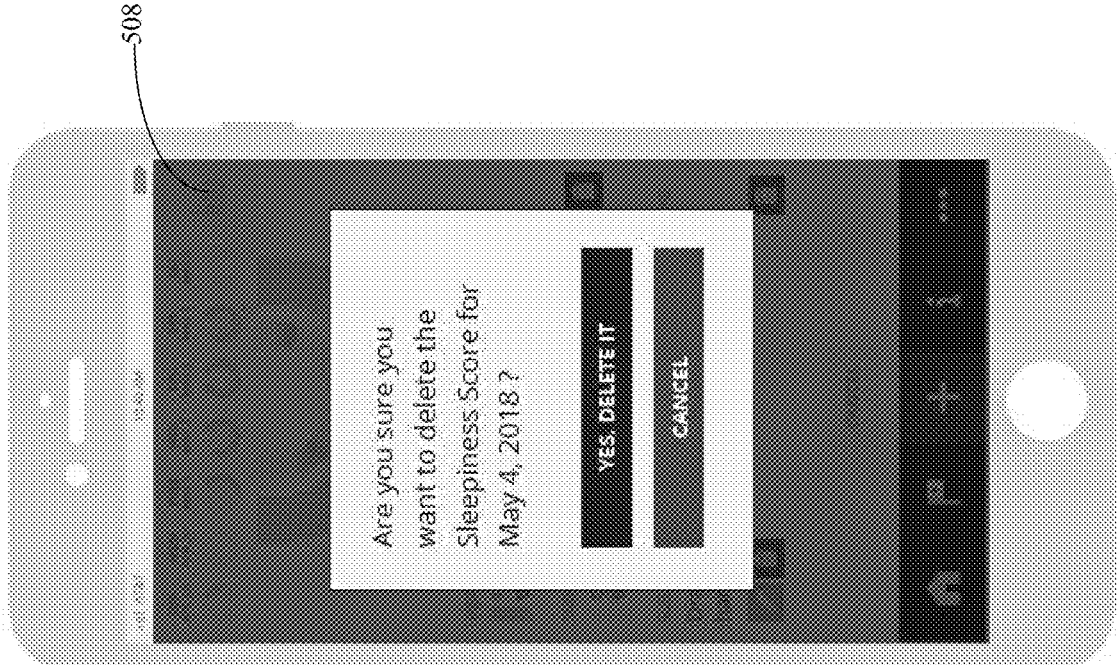
Figure 15:
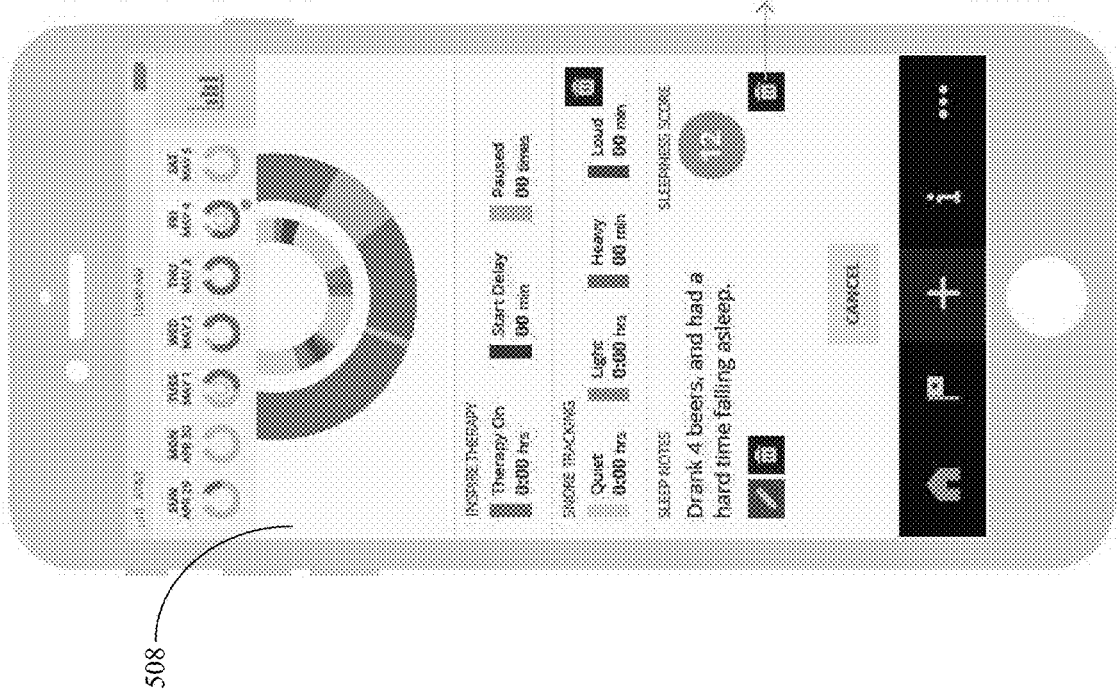
Figure 20:
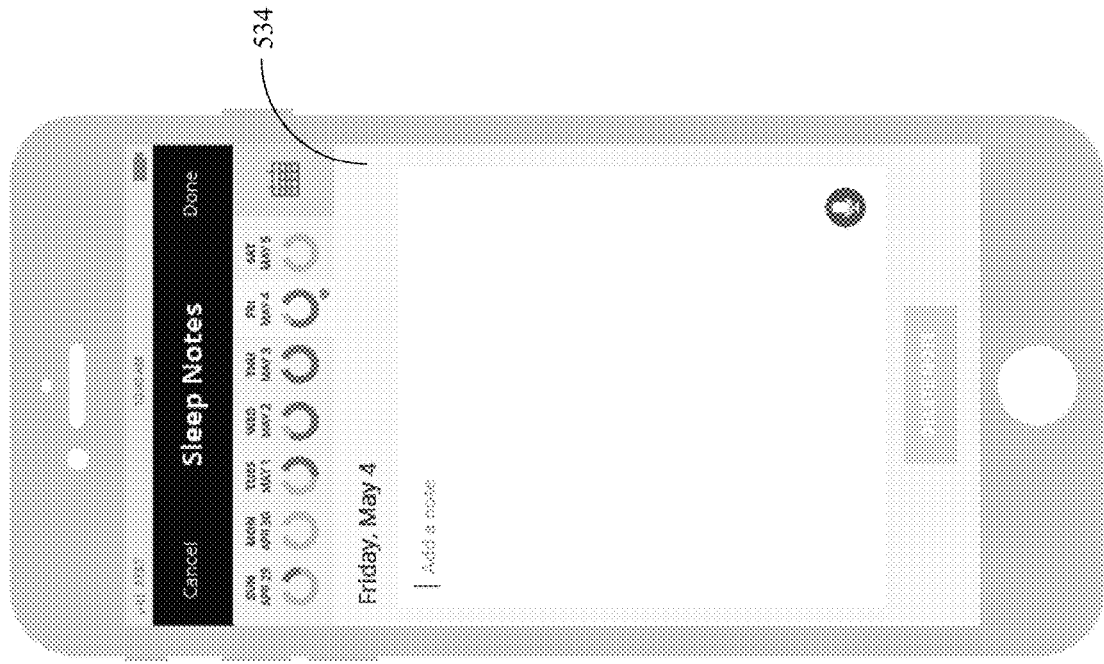
Figure 19:
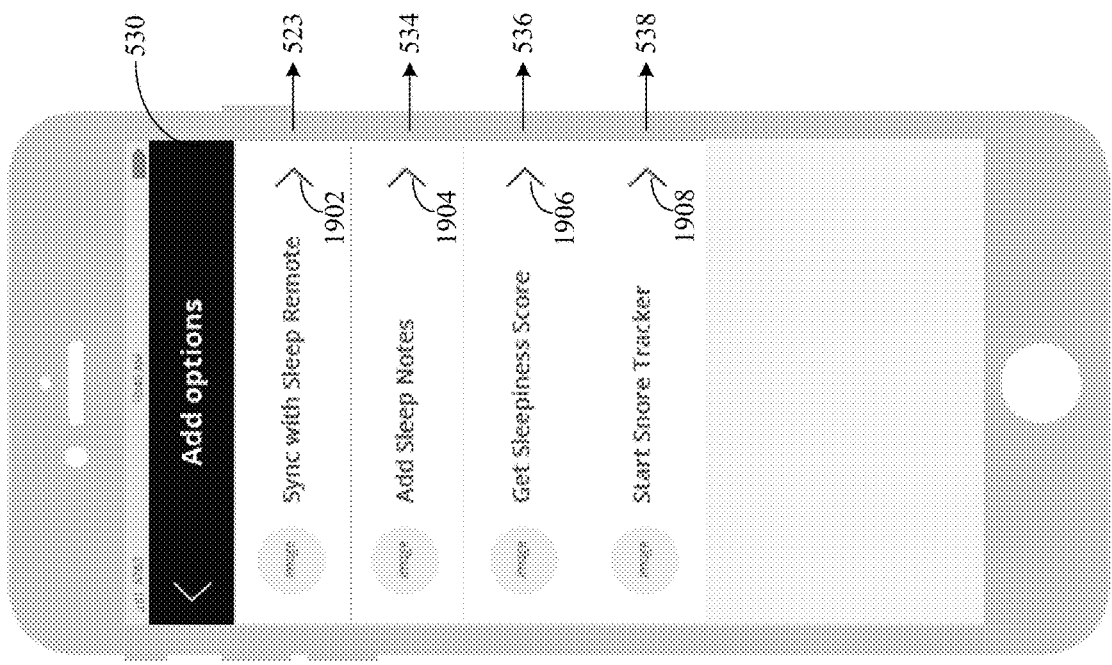
Figure 22:
Figure 21:
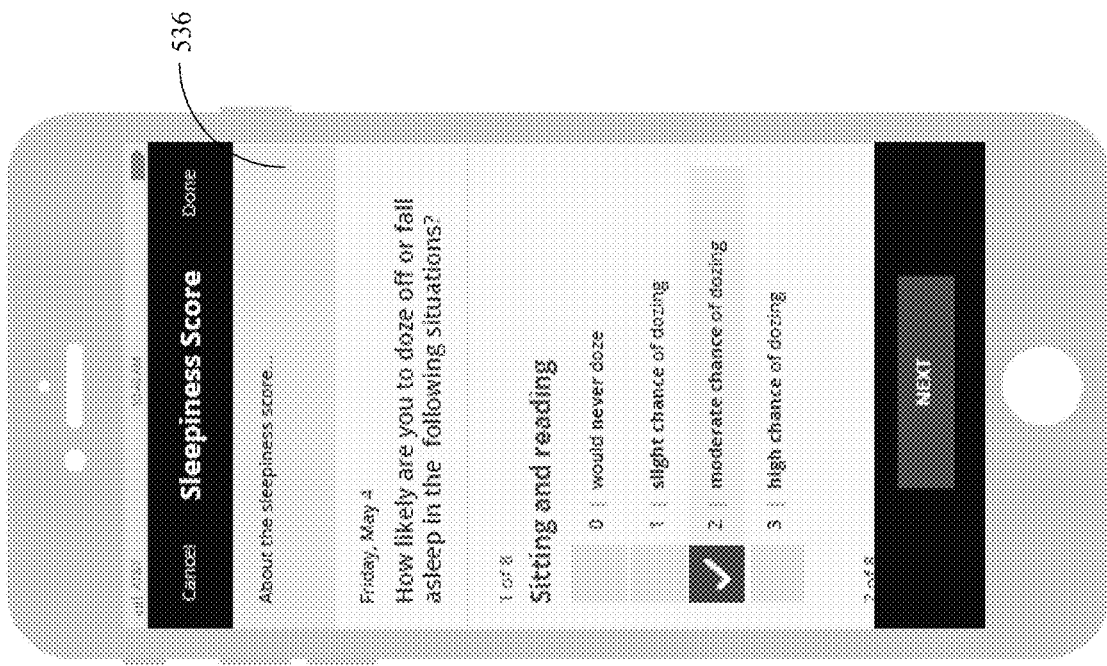

The home screen 508 also includes patient-generated data in the form of sleep notes 1208 entered by the patient and a sleepiness score 1210. The sleep notes 1208 can be entered by the patient using the Sleep Notes screen 534, shown in FIG. 20. The patient can add notes for one or more days, and notes can be entered by typing or talking. With reference to FIG. 20, a calendar icon opens a date selected by the patient. The Sleep Notes screen 534 allows the patient to add, edit, and delete notes. As is shown in FIGS. 14 and 15, the patient can also edit and delete the sleep notes 1208 at a later time. The sleepiness score 1210 is computed by a processor of the smartphone based on patient answers to a number of survey questions. In particular, and as shown in FIGS. 21 and 22, a clinical survey, such as an Epworth Sleepiness Scale (ESS) questionnaire, can be presented to the patient. Patient answers to the survey questions form the basis of the sleepiness score 1210. The patient can also edit and delete the sleepiness score 1210, as is shown in FIGS. 15 and 16. It is noted that the sleep notes 1208 and the sleepiness score 1210 can be accessed via the Add Data screen 530 shown in FIG. 19 (via buttons 1904 and 1906). The Add Data screen 530 also allows the patient to initiate synchronizing with the patient remote (via button 1902) and start the Snore Tracker (via button 1908).

Figure 13:
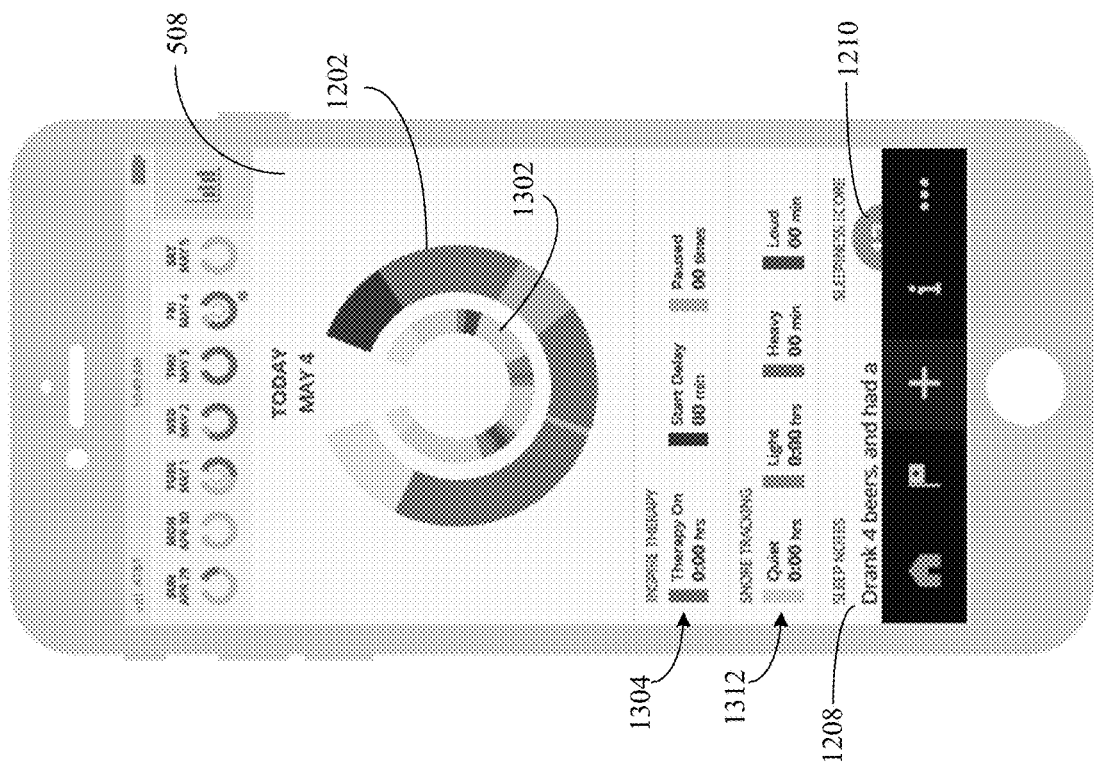

FIG. 13 shows a version of the Home screen 508 that has the same functionality and similar content as the Home screen 508 shown in FIG. 12. In addition to displaying the therapy utilization bar graph 1202, the Home screen 508 of FIG. 13 further includes a therapy utilization summary 1304, which provides details concerning the duration of therapy ON, start delay duration, and the number of therapy pause events. The Home screen 508 in FIG. 13 also includes snoring data, in graphical and summary form.

The snoring data is shown as a stacked bar graph 1302 having an open ring configuration similar to that of the therapy utilization bar graph 1202. The snoring graph icon 1302 is situated within the interior of the therapy utilization graph icon 1202. The snoring graph icon 1302 and the therapy utilization graph icon 1202 are positioned in temporal (radial) alignment with one another. The snoring bar graph 1302 presents snoring data as bars of different character (color, hatching) having a size proportional to a magnitude (e.g., intensity or severity) of the snoring data. For example, different colors or hatching patterns can be used to denote different categories of snoring, such as quiet, light, heavy, and loud storing. The processor of the smartphone can analyze a snoring signal received from the microphone and discriminate the different categories of snoring based on different amplitude thresholds associated with each snoring category. A summary 1312 of the snore tracking data is presented on the Home screen 508. It is noted that scrolling down the Home screen 508 exposes the sleep notes 1208 and the sleepiness score 1210.

Figure 24:
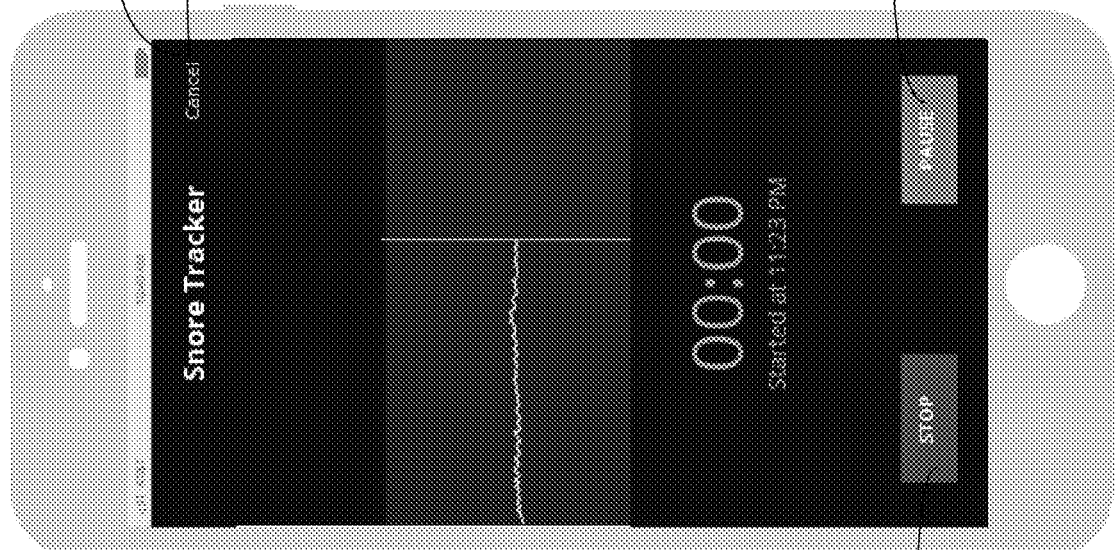
Figure 23:
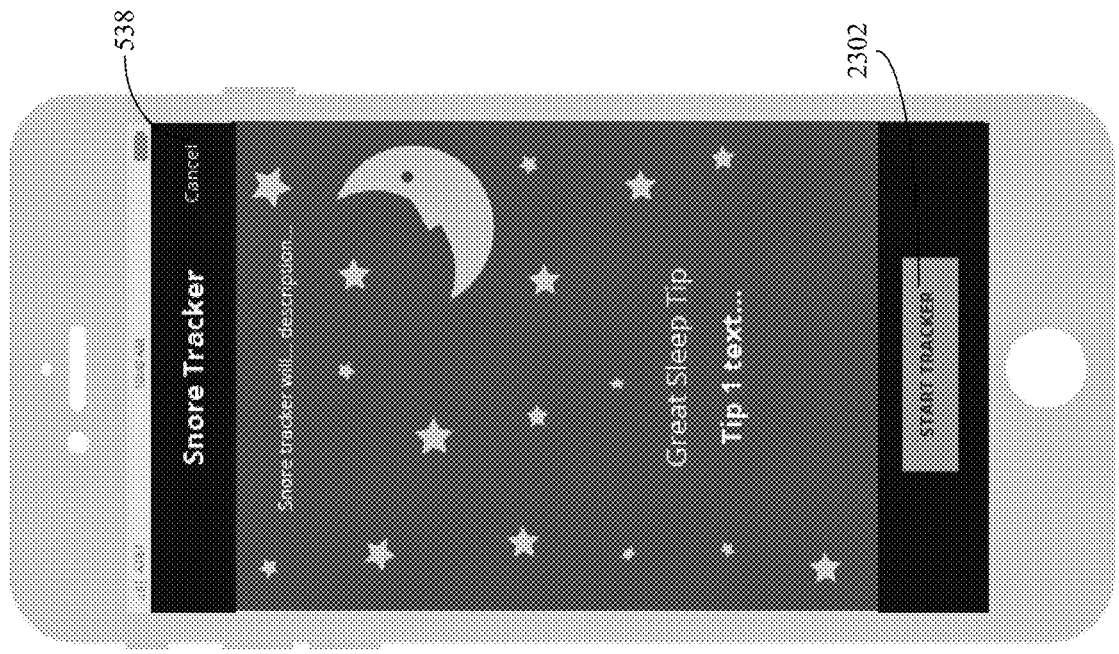
Figure 25:
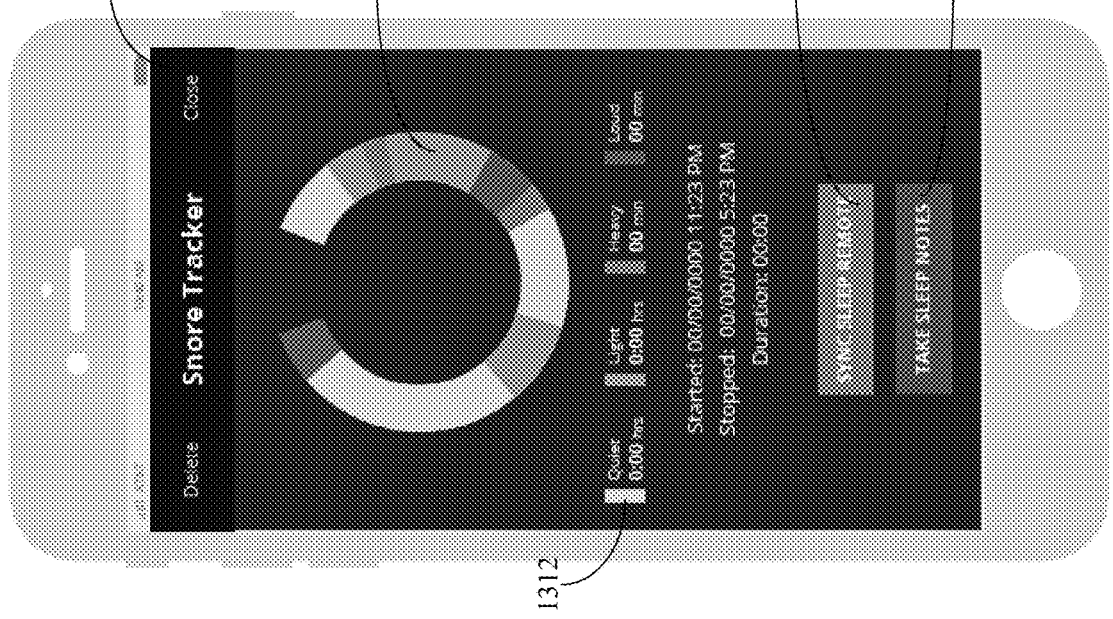

In some embodiments, the stacked bar graph 1302 (inner ring of data) can be representative of any type of sensor data or disease burden data. For example, the inner ring of data 1302 can be disease burden data derived from any of the following or a combination: Apnea-Hypopnea Index (AHI), oxygen saturation (SpO2), oxygen desaturation index (ODI), snoring, blood glucose level, heart rate variability, blood pressure, and atrial fibrillation (AF). The inner ring of data 1302 can be posture data (e.g., sleeping position, such as left, right, prone, supine via an accelerometer). The inner ring of data 1302 can be sleep stage data derived from one or more of the following or a combination: brain activity (e.g., electroencephalogram, EEG), muscle activity (e.g., electromyogram, EMG), heart mechanical activity (e.g., heart sounds, seismocardiogram, SCG), heart electrical activity (electrocardiogram, ECG), heart rate, heart rate variability, blood pressure, temperature, and nerve activity. Alternatively, posture and/or sleep state data can be overlayed or placed in yet a third ring of data or both. Additional sensor data and/or disease burden data can be represented as an additional inner ring or rings of data (e.g., a third inner ring of data, a fourth inner ring of data As was previously discussed, the Snore Tracker can be activated by the patient using button 1908 on the Add Data screen 530 shown in FIG. 19. Actuation of button 1908 causes the Snore Tracker screen 538 shown in FIGS. 23-25 to be presented on the smartphone display. The Snore Tracker screen 538 shown in FIG. 23 provides a short description and tips that can cycle each time the Snore Tracker is selected. The Snore Tracker can be started by patient actuation of button 2302. As is shown in FIG. 24, the patient can stop, pause, and cancel the Snore Tracker by actuation of buttons 2402, 2404, and 2406, respectively. A graphical representation (e.g., in signal form) of the patient's snoring data can be displayed, as can be the time the Snore Tracker was started in the total duration of snore tracking. The Snore Tracker screen 538 shown in FIG. 25 includes the snoring bar graph 1302 and summary 1312 of the snoring data by severity category. The start time, stop time, and total duration of snore tracking is also displayed. Button 2502 allows the patient to synchronize the smartphone with the patient remote in order to update the therapy data stored in the smartphone. Button 2504 allows the patient to jump to the Sleep Notes screen 534 shown in FIG. 20 to enter and edit sleep notes.

Although the Home screen 508 shown in FIG. 13 includes snoring data, other objective data indicative of a patient's disease state can be displayed in FIG. 13, exclusive of or in addition to snoring data. For example, Apnea-Hypopnea Index (AHI), oxygen saturation data (SpO$_2$) and/or oxygen desaturation data index (ODI) can be computed/acquired (e.g., from the implantable therapy device and/or one or more physiologic sensors), monitored, and displayed on the Home screen 508. Obstructive and central apnea events can be detected (e.g., by the implantable therapy device), monitored, and displayed on the Home screen 508. These objective data can be displayed in close proximity to therapy utilization data to allow visual correlation between disease state events and/or trends and therapy utilization data. Disease state information over time can also be presented separately on the Home screen 530 or on another screen. Moreover, disease state information can be displayed as a heatmap (e.g., hotter colors where severity is larger, cooler colors where verity is smaller). Disease state information can be correlated to other sensor information, in addition to or instead of therapy utilization data. For example, disease state information can be displayed with posture data (supine, prone, left, right) detected by an accelerometer of the smartphone. Disease state information can be displayed with sleep state information, such as REM and Non-REM sleep state data. The source of objective data displayed in FIG. 13 can include a wide variety of sources (e.g., Bluetooth®, ZigBee®, ODI, snoring, other external sleep sensor, sensor with implanted system).

Figure 11:
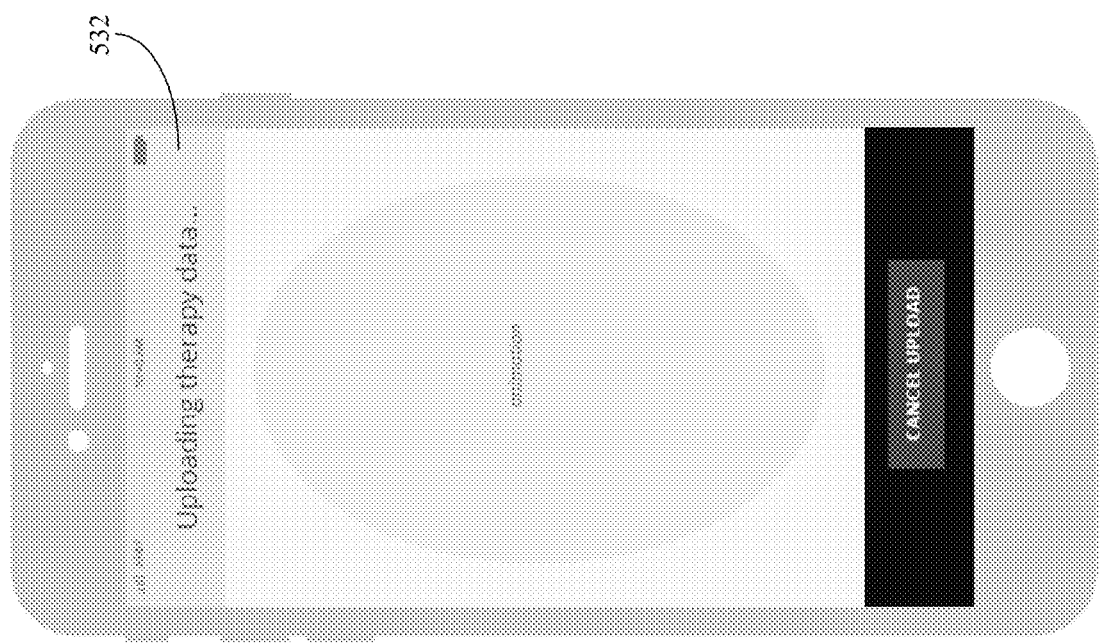
Figure 17:
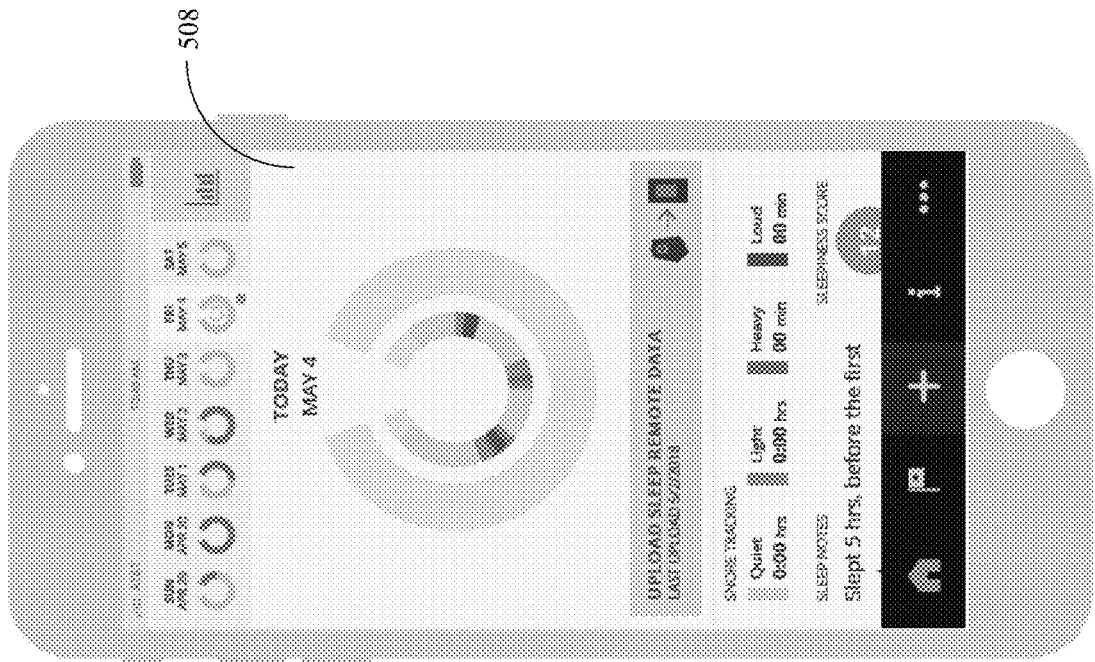
Figure 18:
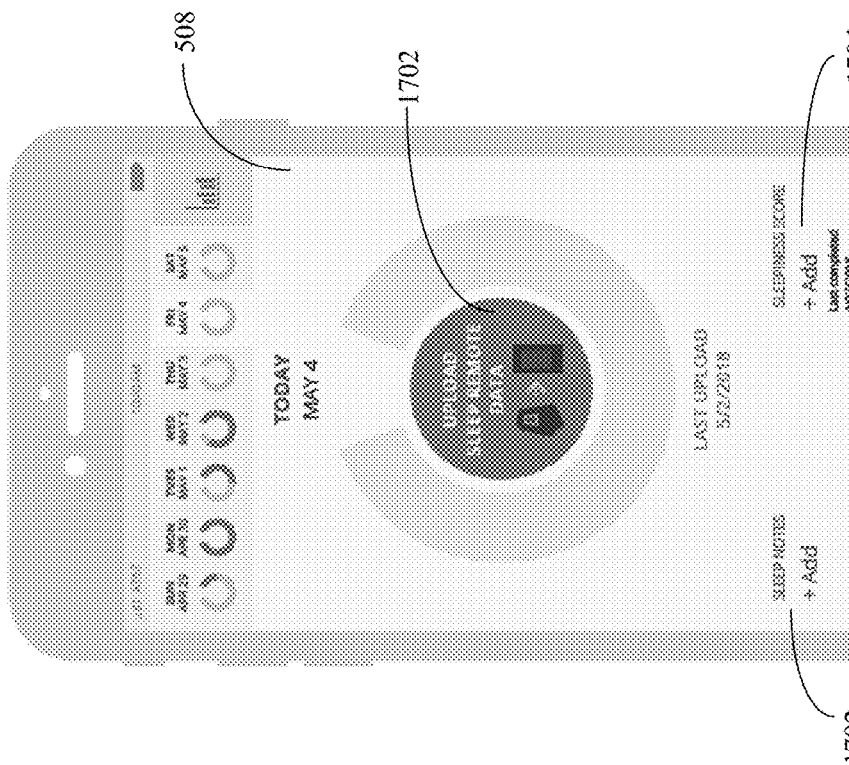

FIG. 17 shows a version of the Home screen 508 in which no data has been uploaded for the current day (Today). The last upload date is displayed on the Home screen 508. The center region of the Home screen 508 changes to an action button 1702 which, when actuated by the patient, causes the Upload screen 532 of FIGS. 10 and 11 to be displayed. Following the instructions of the Upload screen 532, therapy data can be transferred from the patient remote or the implantable therapy device to the smartphone. Button 1702 allows the patient to add sleep notes via the Sleep Notes screen 534 shown in FIG. 20. Button 1704 allows the patient to add a sleepiness score via the Sleepiness Score screen 536 shown in FIGS. 21-22. FIG. 18 is an example of what the Home screen 508 looks like when therapy data is unavailable for the current day (Today), but snoring data and patient-generated data (sleep notes and sleepiness score) are available.

Figure 26:
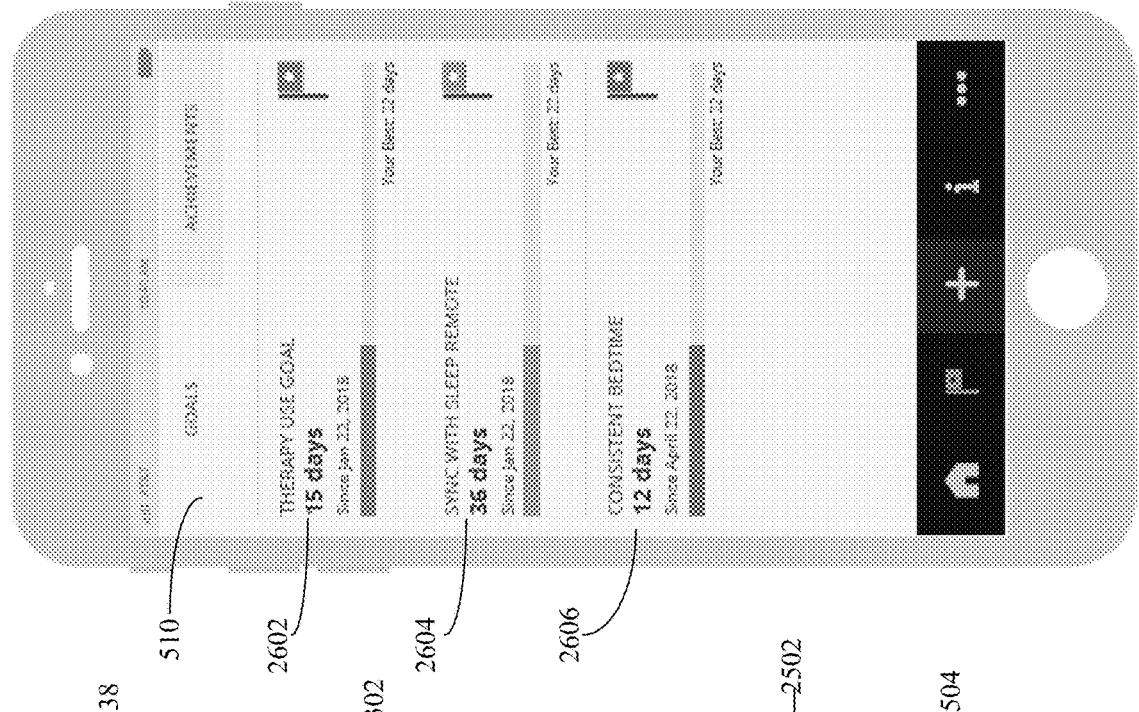
Figure 27:
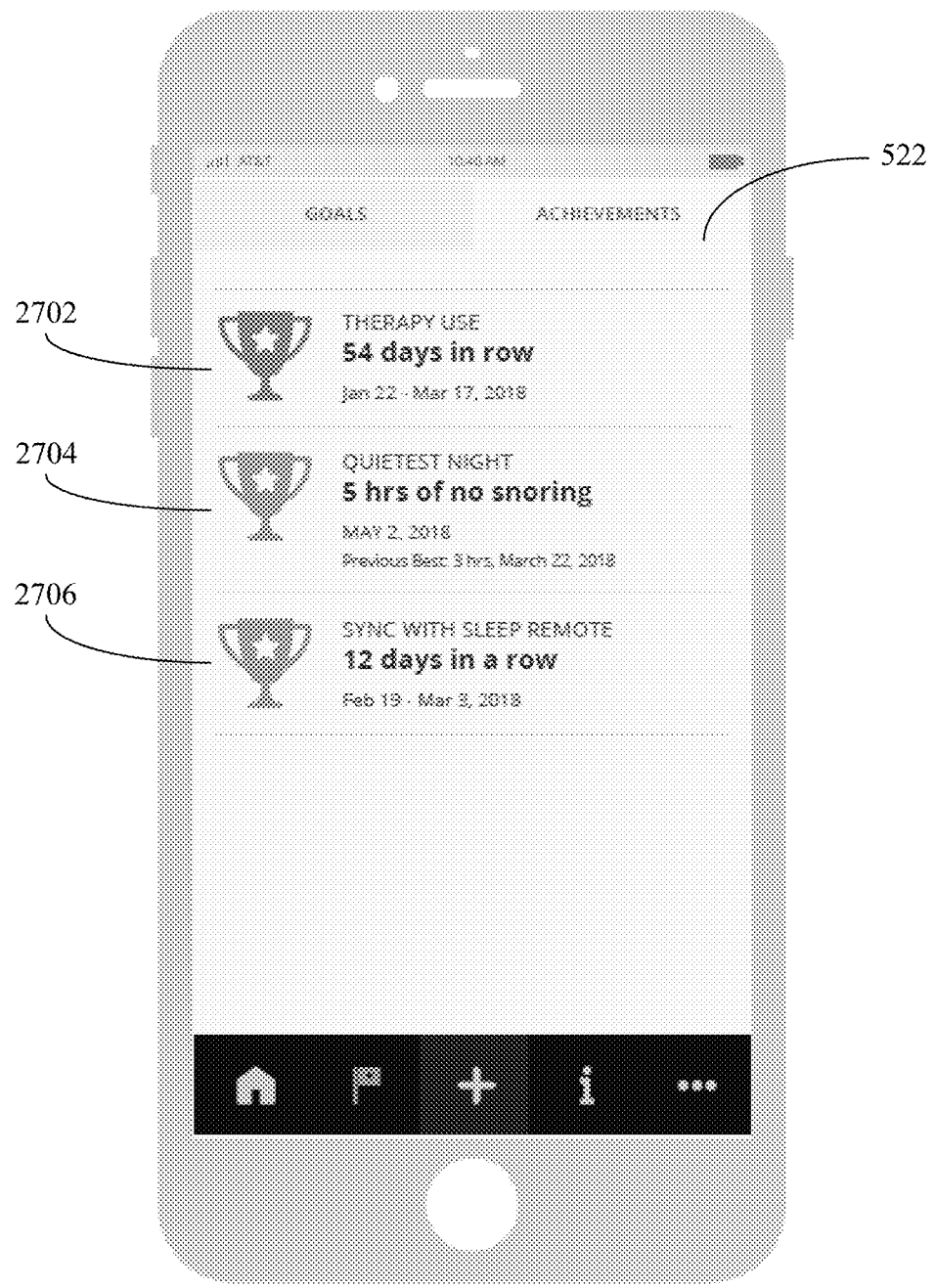

The Goals screen 520 is shown in FIG. 26. The Goals screen 520 includes a "Therapy Use" goal 2602, a "Sync with Patient Remote" goal 2604, and a "Consistent Bedtime" goal 2606. Each of these goals 2602, 2604, 2606 includes a graphical indicator showing current progress towards each goal. The Achievement screen 522 is shown in FIG. 27. The Achievement screen 522 includes a "Therapy Use" achievement 2702, a "Quietest Night" achievement, and a "Sync with Patient Remote" achievement 2706.

Figure 29:
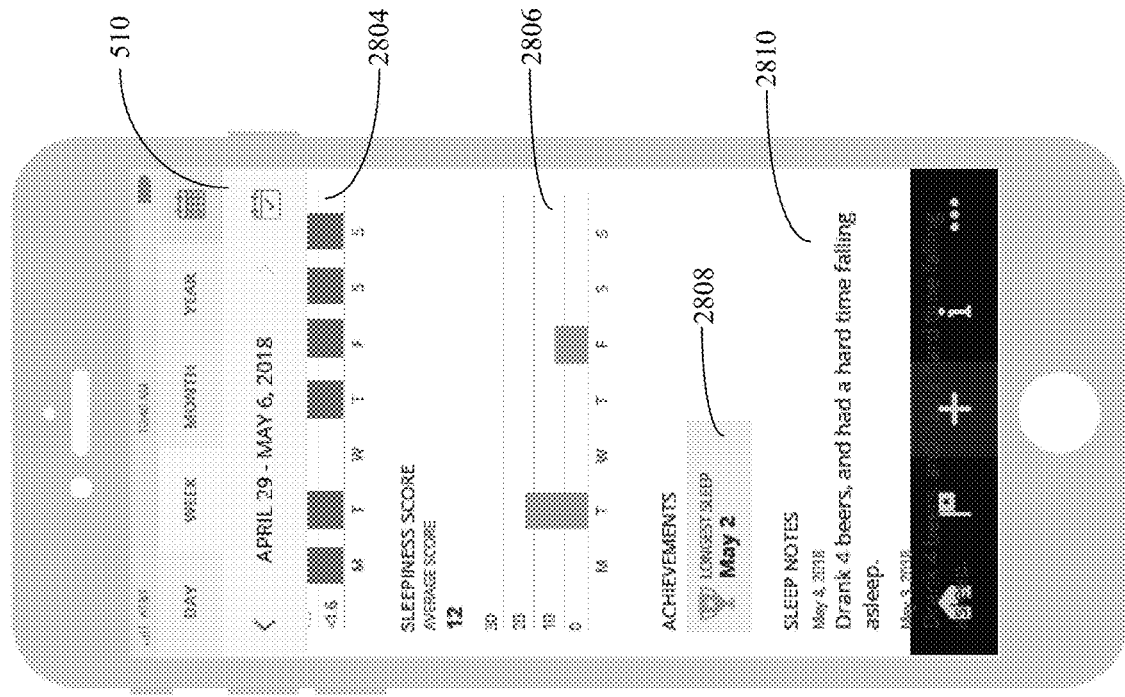
Figure 28:
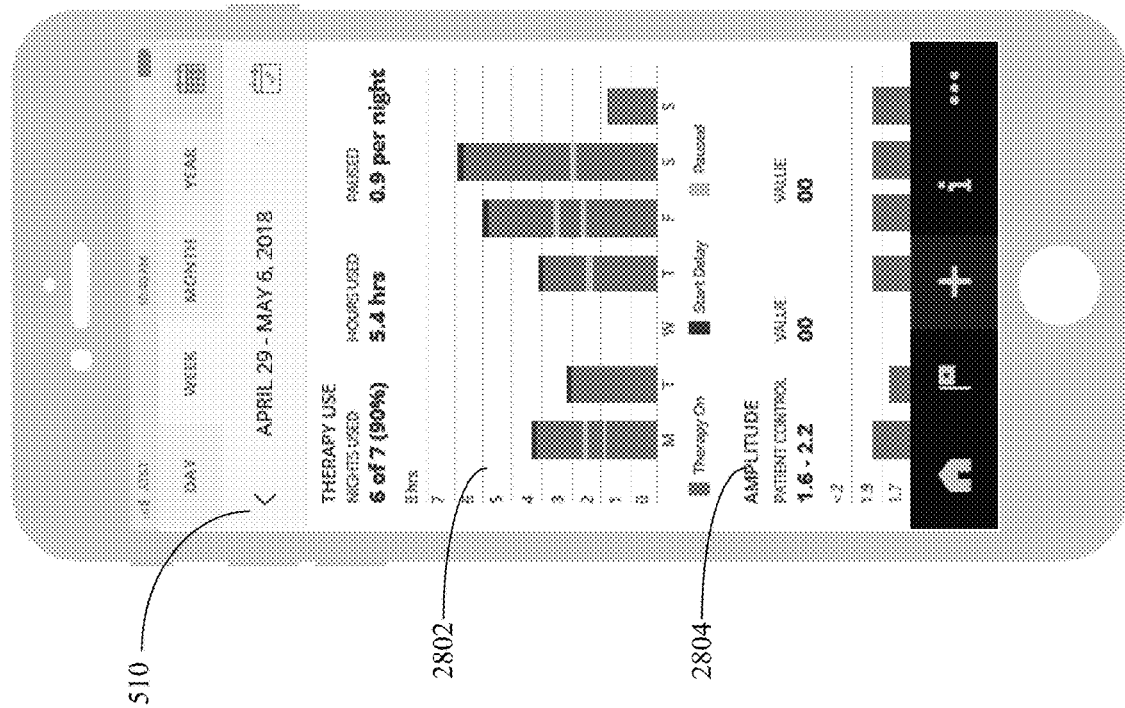
Figure 30:
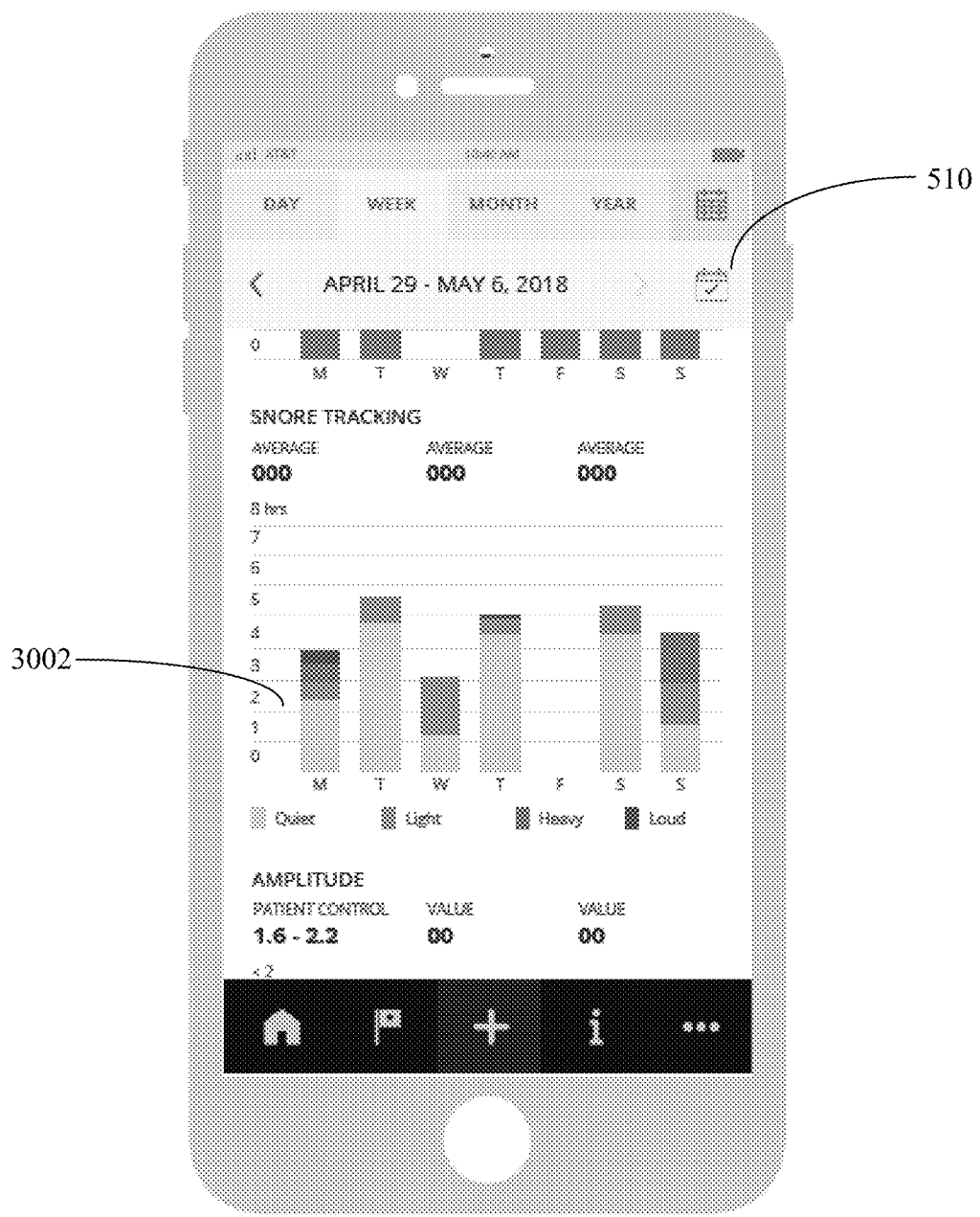

FIGS. 28 and 29 show History screen 510, which is a week view showing daily data, averages, and achievements. The patient can select a specific date range by selecting the calendar icon. Selecting the calendar with the checkmark icon will return the patient to the current day's (Today's) data. Therapy use data 2802 is presented as a stacked bar graph for each day of the week. The number and percentage of nights therapy was used during the week are displayed. The average number of hours therapy was used and the average number of pause events are respectively displayed. Stimulation amplitude data 2804 is graphically displayed in bar graph form for each day of the week. The predetermined amplitude range established by the clinician is also displayed. Scrolling down the History screen 510 reveals the patient's sleepiness score 2806 for each day of the week. Also displayed are the patient's achievements 2808 and sleep notes 2810. Snore tracking data 3002, shown in FIG. 30, is also presented on the History screen 510, such as after the amplitude section 2804. The snore tracking data 3002 is presented as a stacked bar graph for each day of the week.

Figure 32:
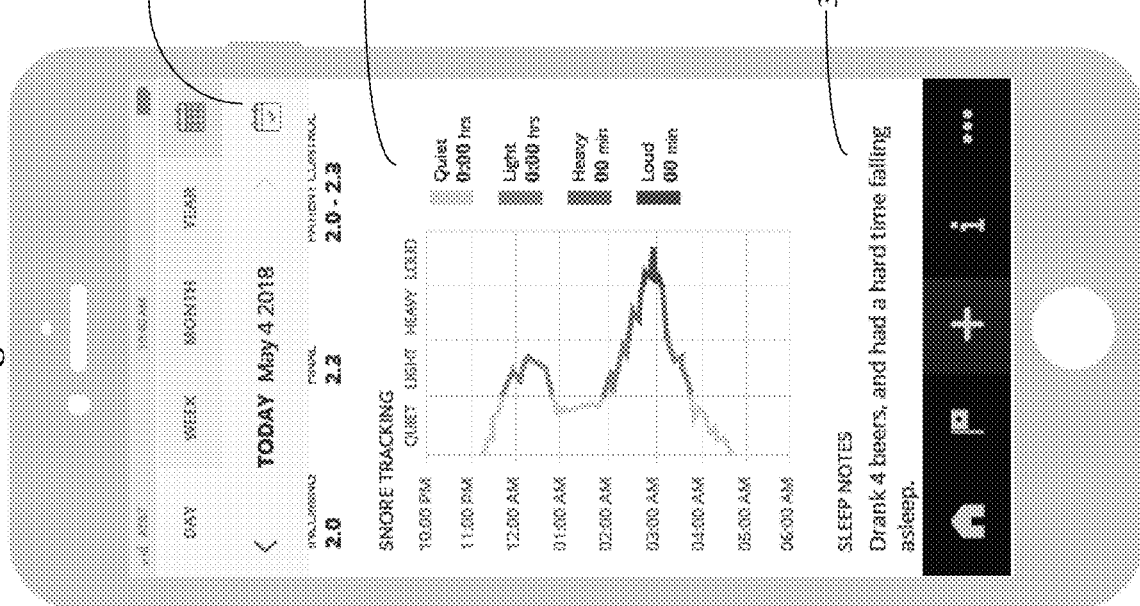
Figure 31:
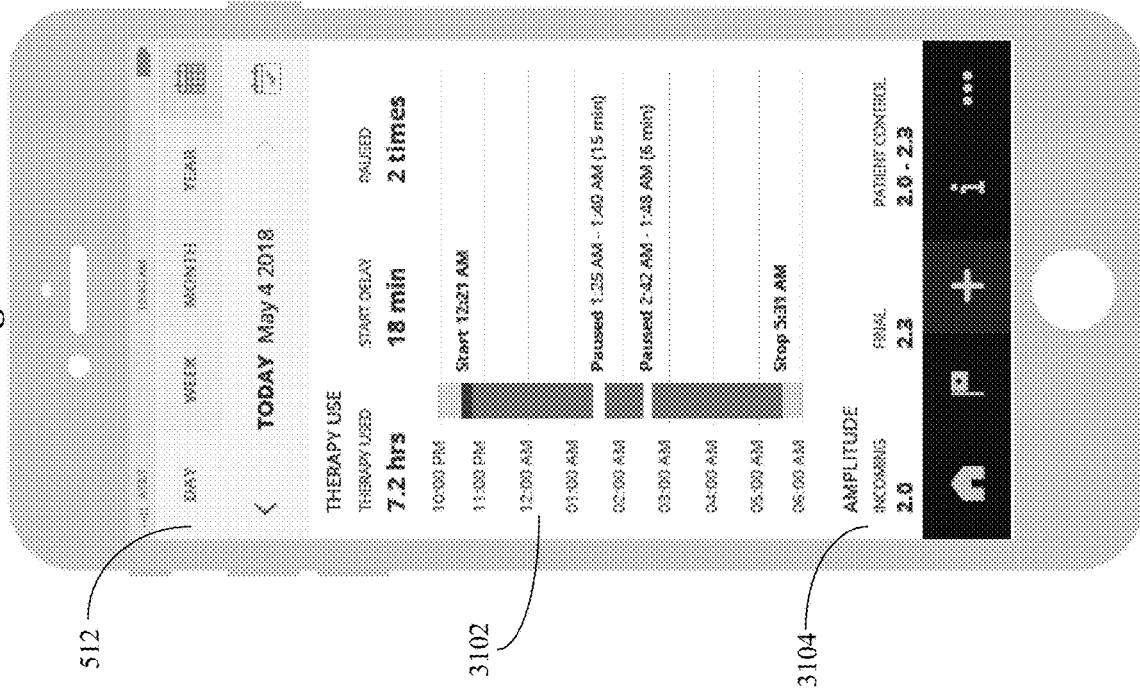

FIGS. 31 and 32 show History screen 512, which is a day view showing more detailed information on therapy utilization 3102, amplitude 3104, and snore tracking 3104. The day view defaults to the current day (Today), but can be selected by the patient using the calendar icon. The therapy use data 3102 provides a graphical representation (stacked bar graph) showing the time and duration for therapy ON, therapy pause, and therapy OFF phases. Amplitude data 3104 includes incoming, final, and patient control range data. The snore tracking data 3106 includes a snoring severity line chart presented as a function of time over the course of the night. Sleep notes 3108 are also presented.

Figure 33B:
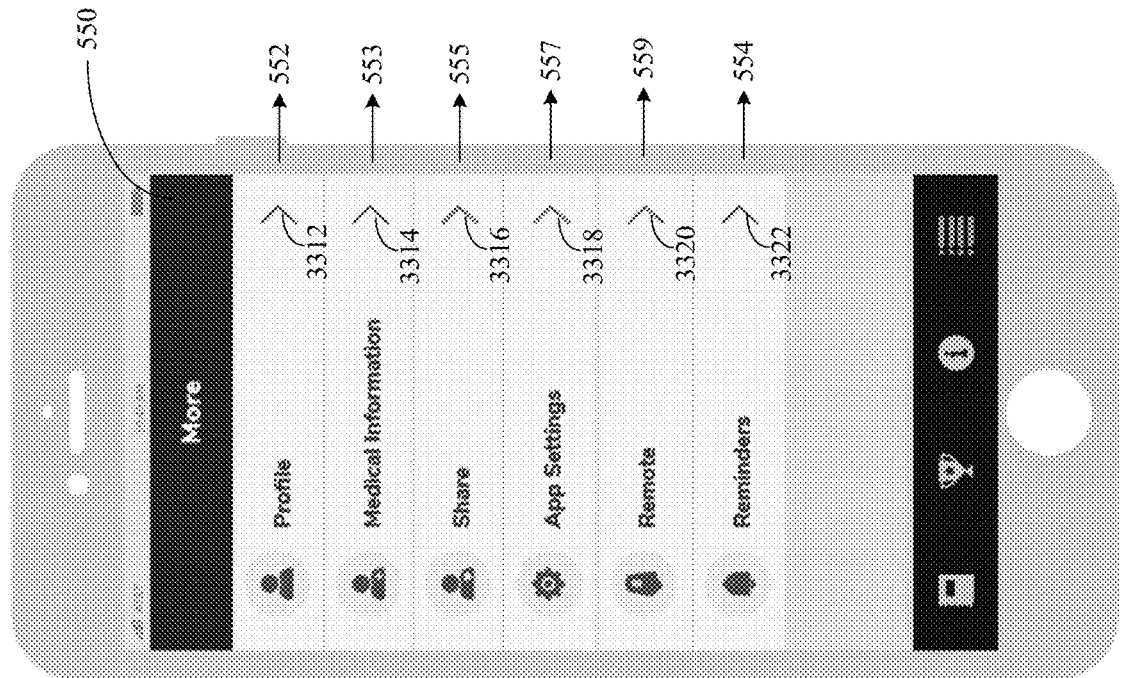
Figure 33A:
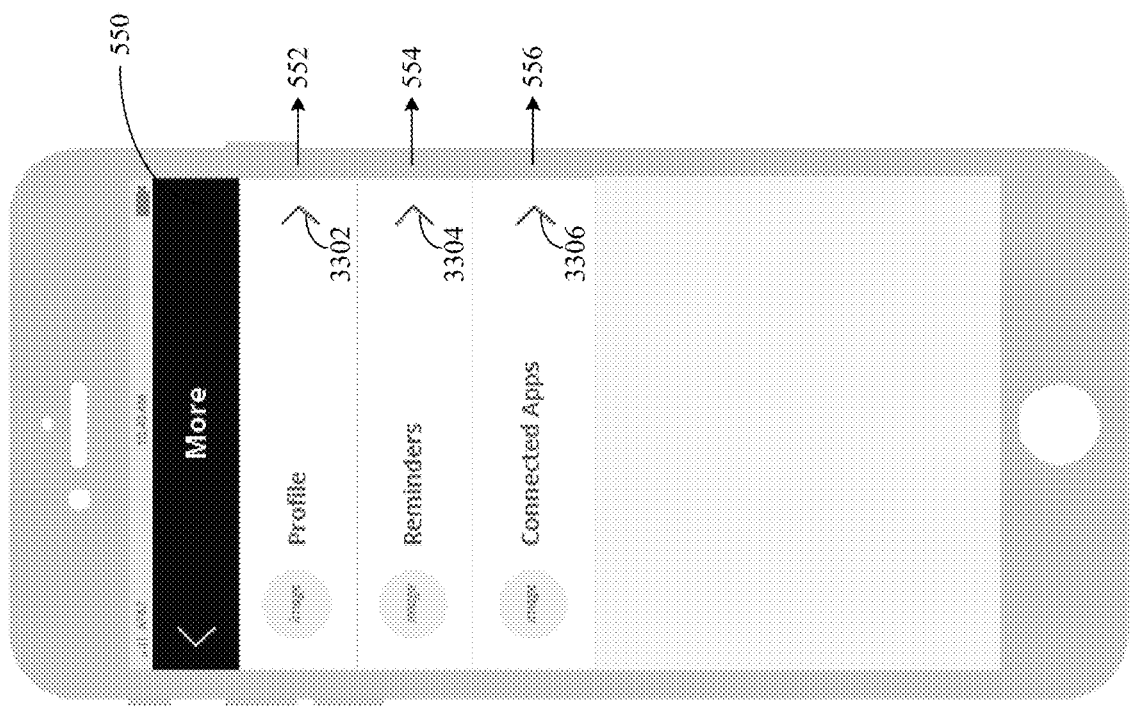
Figure 34:
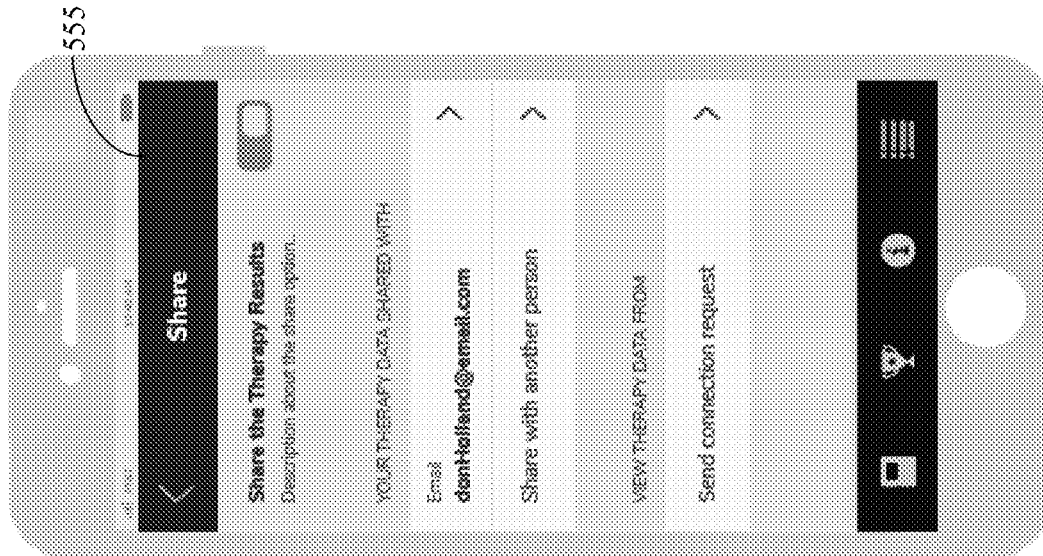
Figure 39:
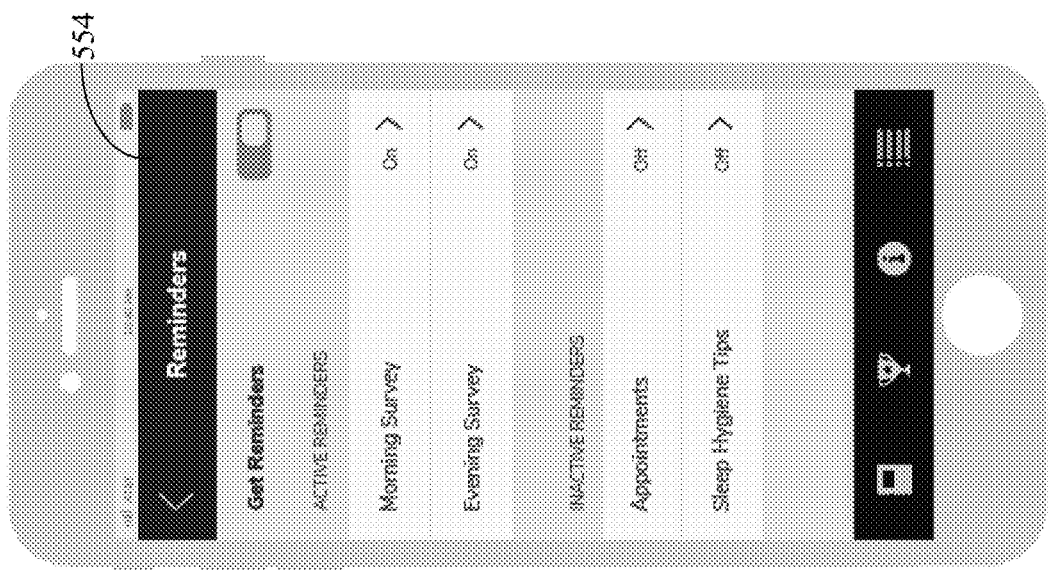

FIG. 33A shows an embodiment of More screen 550. The More screen 550 provides links to various settings and controls. For example, a Profile screen 552 can be accessed via button 3302 to view and edit profile information. A representative example of the Profile screen 552 is shown in FIG. 34. A Reminder screen 554 can be accessed via button 3304 to view and edit reminders. A representative example of the Reminder screen 554 is shown in FIG. 39. A Connected Apps screen 556 can be accessed via button 3306 to add and edit connected apps. A representative example of the Connected Apps screen 556 can include the App Setting screen 557 shown in FIG. 38.

Figure 35:
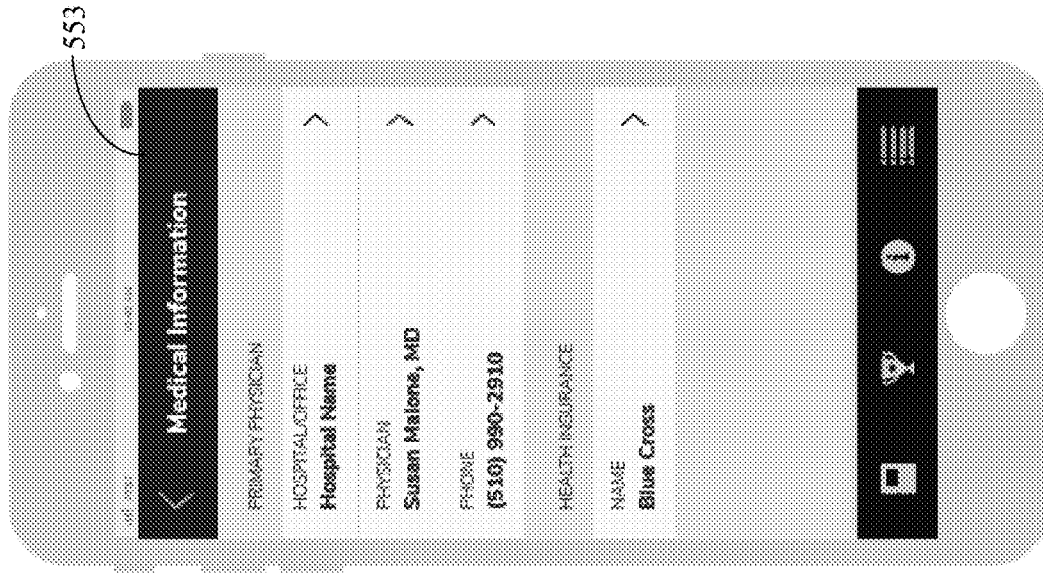

FIG. 33B shows another embodiment of More screen 550. The More screen 550 shown in FIG. 33B includes a Profile screen 552 which can be accessed via button 3312 to view and edit profile information (see, e.g., FIG. 34). A Medical Information screen 553 can be accessed via button 3314 to view and edit patient medical information. A representative example of the Medical Information screen 553 is shown in FIG. 35. In this representative example, the medical information accessible via the Medical Information screen 553 can include the patient's physician information (e.g., name, hospital/office, phone number, email address) and the patient's health insurance information.

Figure 36:
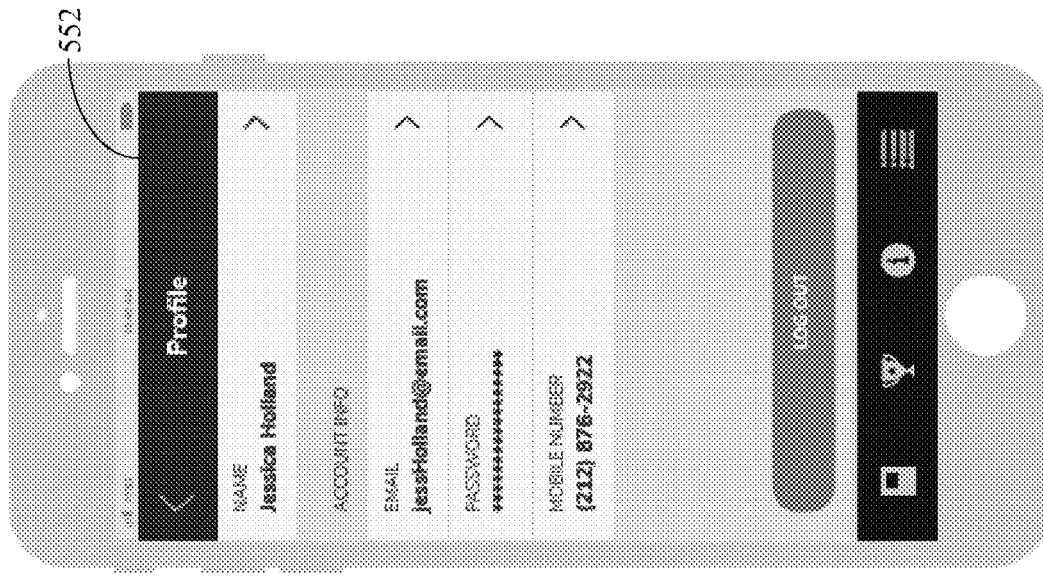

A Share screen 555 can be accessed via button 3316 to view and edit information (e.g., names, email addresses, text numbers) concerning persons (doctors, clinicians, caregivers, family/friends) and/or entities with whom medical and other data can be shared. A representative example of the Share screen 555 is shown in FIG. 36. In general, the Share screen 555 allows the patient to share therapy and other medical information with others (persons and/or entities) via the smartphone. The Share screen 555 also allows the patient to view patient therapy data from a remote source via a connection established by the patient using a connection request. The source of the shared therapy/medical data and other data can be the patient's smartphone and/or a remote server that communicates with the patient's smartphone and other information resources (e.g., medical clinic server).

Figure 38:
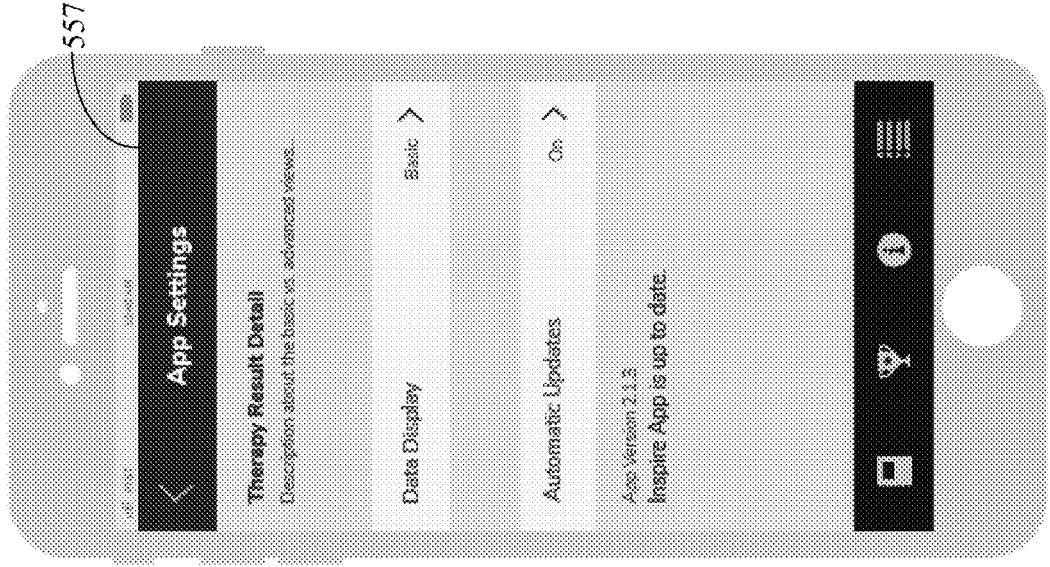
Figure 37:
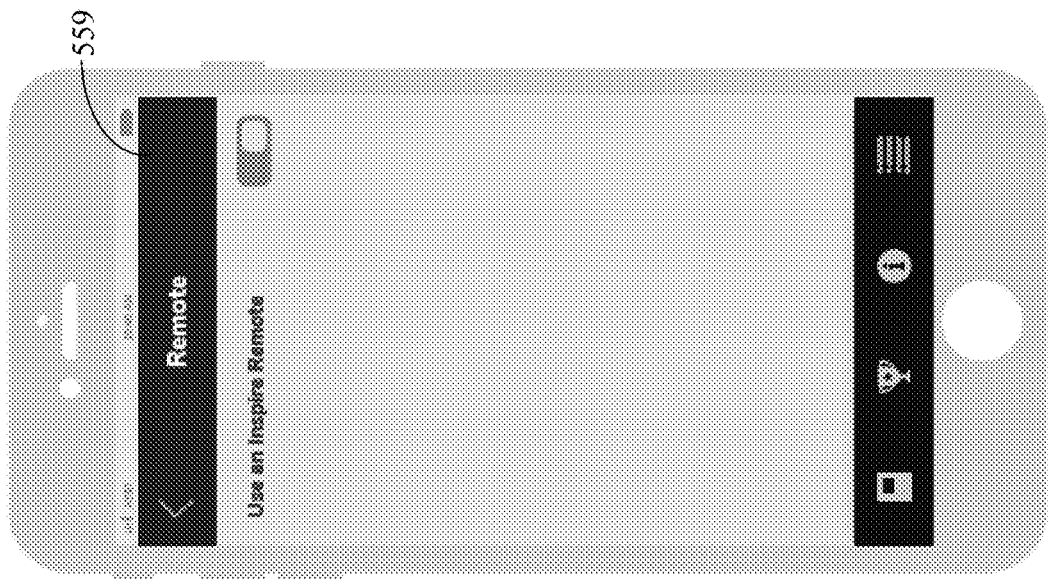

An App Settings screen 557 can be accessed via button 3318 to view and edit settings for one or more apps (e.g., connected apps) executable by the patient's smartphone. A representative example of the App Settings screen 557 is shown in FIG. 38. The App Settings screen 557 can be used to set up automatic app updates for the patient's smartphone, initiate a manual app update, and/or select various ways data can be presented to the patient on the smartphone display (e.g., basic views or advanced views). A Patient Remote screen 559 can be accessed via button 3320 to view and edit settings for communicating with and/or controlling a patent remote configured to communicate with and/or program a medical device (e.g., implantable medical device). A Reminder screen 554 can be accessed via button 3322 to view and edit reminders. In the representative example shown in FIG. 39, active reminders can be set, such as a Morning Survey reminder and an Evening Survey reminder. Activation of the Morning Survey reminder and the Evening Survey reminder can cause the mobile app to present the Morning Check-in and Evening Check-in screens 4302, 4402 shown in FIGS. 43 and 44. Inactive reminders can also be set, such as an Appointments reminder and a Sleep Hygiene Tips reminder.

FIGS. 40-61 show representative screens and functions associated with sleep log functionality implemented by a consumer electronic device in accordance with various embodiments. The sleep log functionality provides for the gathering of sleep-related information input by the patient and/or acquired automatically by the mobile app executed by the consumer electronic device. For example, sleep log data can be manually input (e.g., patient-subjective sleep log data input using a touch keyboard or verbal inputs) by the patient using the various screens shown in FIGS. 40-61. Additionally or alternatively, some of the sleep log data (e.g., patient-objective sleep log data) can be gathered automatically from the mobile app by, for example, sensing usage patterns (e.g., use of the patient's smartphone before bed and upon waking) as well as environmental sensors, such as ambient light (e.g., via the smartphone's ambient light sensor), motion (e.g., via the smartphone's accelerometer or gyro), and sound sensors (e.g., via the smartphone's microphone). The sleep log functionality implemented by the mobile app executed on the patient's consumer electronic device can additionally provide the patient with sleep hygiene tips and educational content.

As is shown in FIG. 5, sleep log functionality can be implemented by the patient's smartphone using a Sleep Log screen 537. The Sleep Log screen 537 allows the patient to initiate sleep log functionality using the representative screens shown in FIGS. 40-56. These screens allow the patient to input various types of sleep log information and to receive sleep hygiene tips. The patient can receive therapy and device education via the Therapy & Device Education screen 539. Activating the Therapy & Device Education screen 539 causes the presentation of screens that provide educational information on therapy deliverable to the patient, the therapy device implanted in the patient, and how to track the patient's sleep details. Representative educational screens are shown in FIGS. 57-61.

Figure 40:
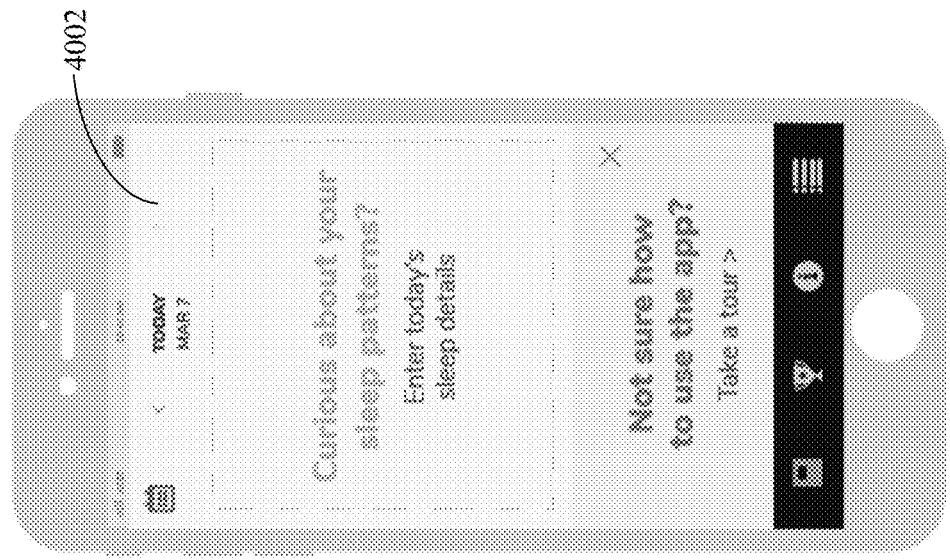

FIG. 40 shows a screen 4002 that can be presented to the patient in response to activating the Sleep Log/Sleep Hygiene Tips screen 537 shown in FIG. 5. Screen 4002 includes a button that allows the patient to begin entering the current day's sleep details. The screen 4002 also allows the patient to take a tour in order to understand how to use the mobile app that implements the sleep log functionality. The tour implemented by the mobile app can include presentation of screen 4102 shown in FIG. 41. Screen 4102 provides information on how to track the patient's sleep details. For example, information is presented graphically and/or textually on how the patient can enter sleep data concerning morning details, evening details, sleep issues, energy levels, etc.

Figure 42:
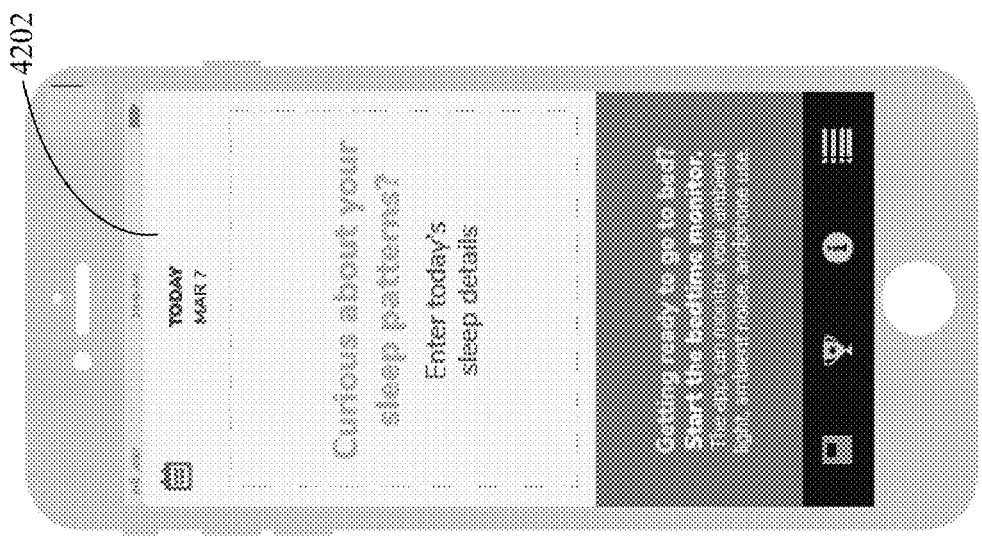
Figure 41:
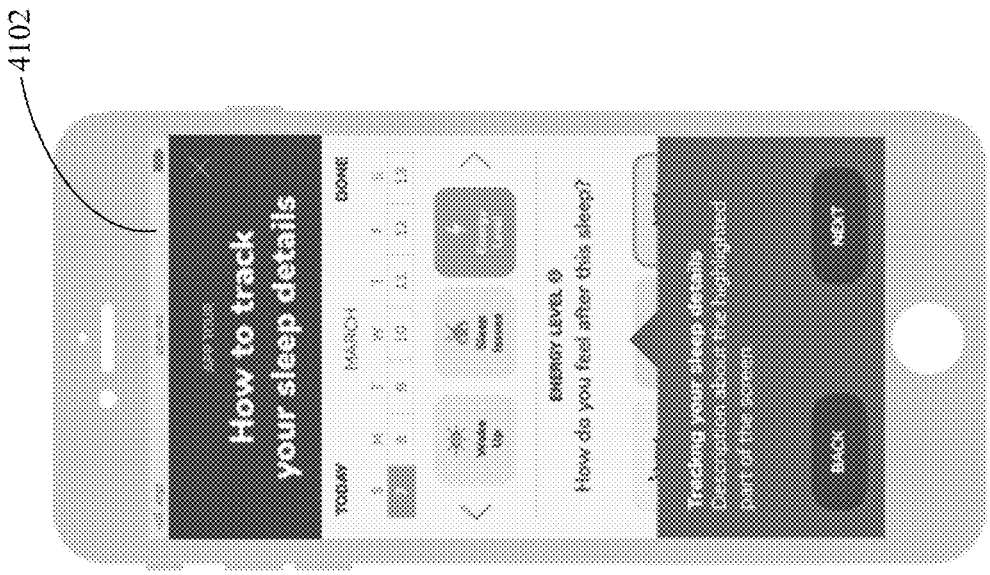

FIG. 42 shows a variation of the screen 4002 shown in FIG. 40. Screen 4202 shown in FIG. 42 includes a button that allows the patient to begin entering the current day's sleep details, and also allows the patient activate a bedtime monitor. The bedtime monitor causes the mobile app to monitor the patient's sleep environment. For example, the bedtime monitor implemented by the mobile app causes environmental sensors of the patient's smartphone to monitor ambient light, ambient noise, and phone use. As was previously discussed, these environmental sensors can include an ambient light sensor, an accelerometer or gyro, and a microphone of the smartphone.

Figure 43:
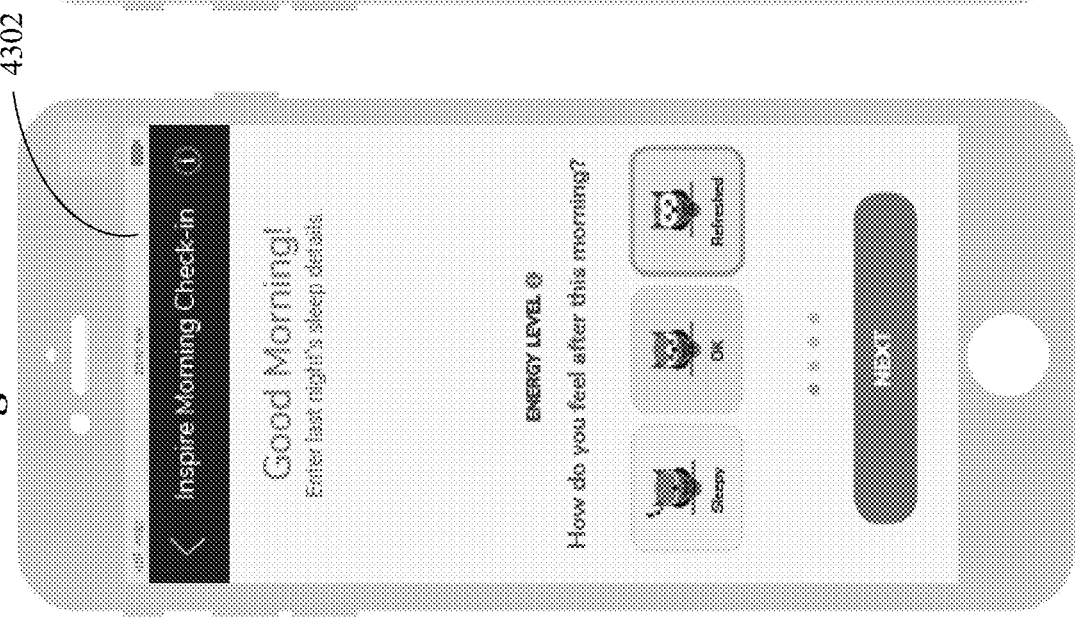

FIG. 43 shows a Morning Check-in screen 4302, which can be activated manually by the patient or automatically by an active reminder. Among other information, the Morning Check-in screen 4302 allows the patient to input his or her energy level (e.g., sleepy, okay, refreshed) in the morning by activation of the appropriate button. The Morning Check-in information acquired through screen 4302 provides insight into the quality of the previous night's sleep.

Figure 44:
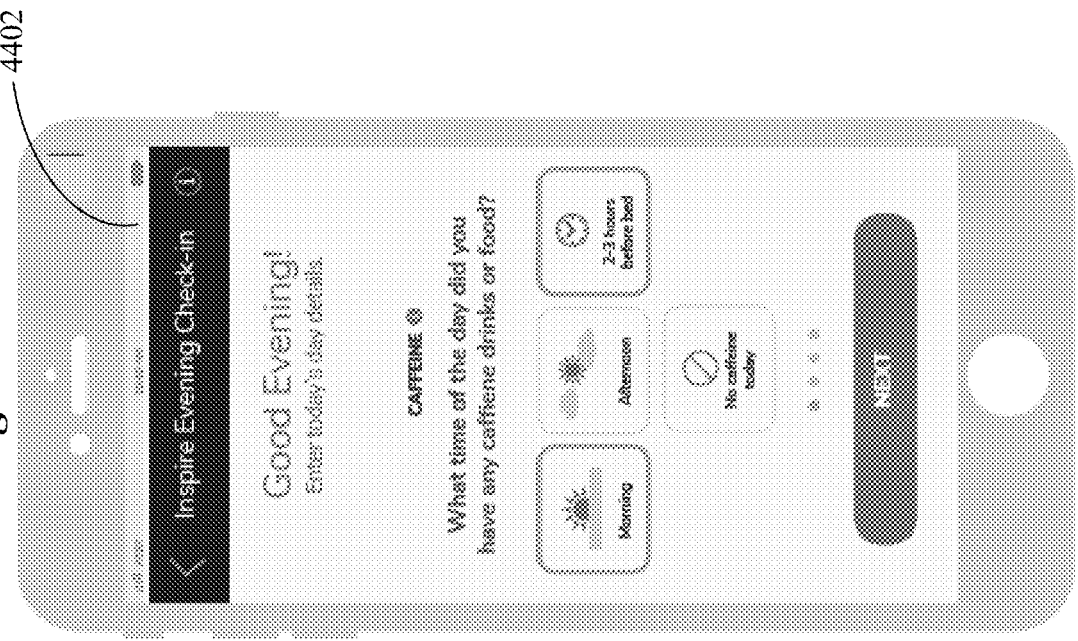

FIG. 44 shows an Evening Check-in screen 4402, which can be activated manually by the patient or automatically by an active reminder. Among other information, the Evening Check-in screen 4402 allows the patient to input details about the current day that can impact the quality of the upcoming night's sleep. For example, the mobile app can present text and/or graphics that allows the patient to input the time of day in which caffeine, alcohol, and heavy meals have been consumed, all of which can negatively impact the quality of the patient's upcoming night's sleep.

Figure 47:
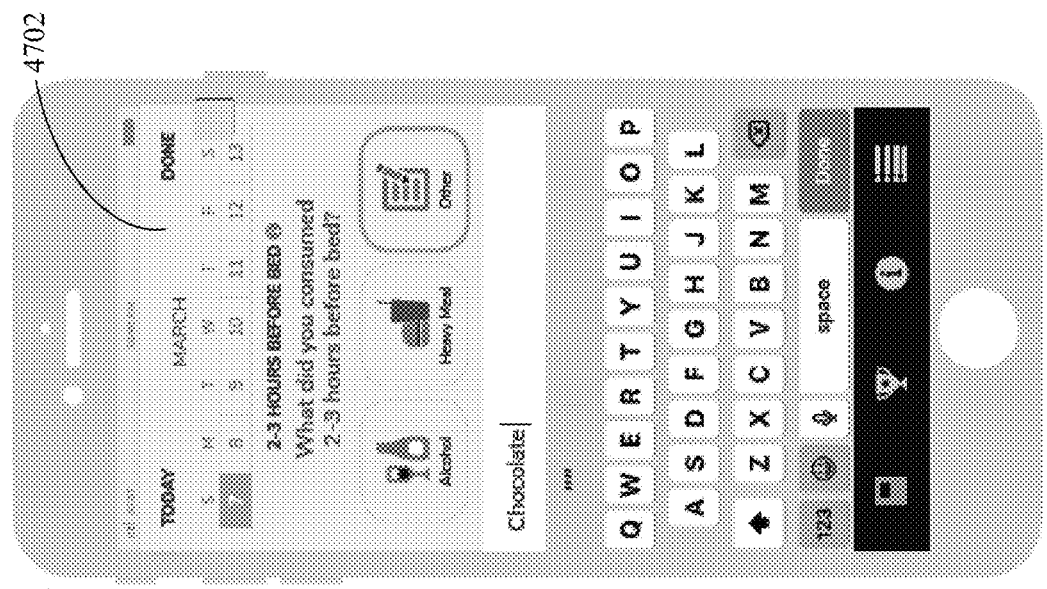
Figure 46:
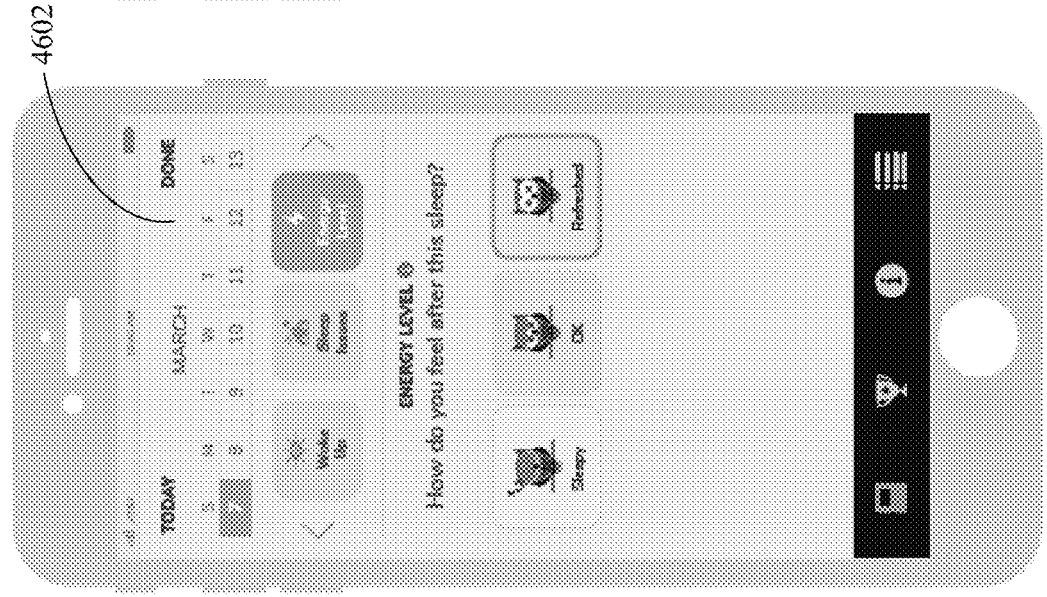
Figure 45:
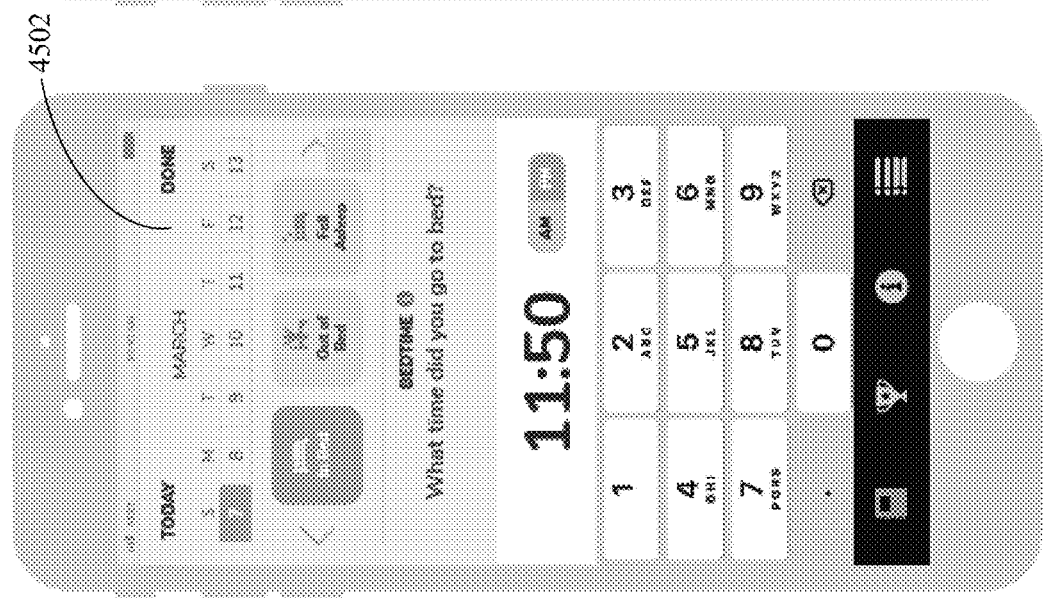

FIGS. 45-47 shows screens that allow the patient to input sleep log information for each day of the week. Screen 4502 shown in FIG. 45 allows the patient to input bedtime information, such as the time of day the patient was in bed, out of bed, and fell asleep. Screen 4602 shown in FIG. 46 allows the patient to input the patient's energy level after the previous night's sleep. Screen 4702 shown in FIG. 47 allows the patient to input information concerning what he or she consumed two to three hours before bedtime. For example, the patient can enter whether or not he or she consumed alcohol, a heavy meal, or other consumable (e.g., chocolate) shortly before bedtime.

Figure 48:
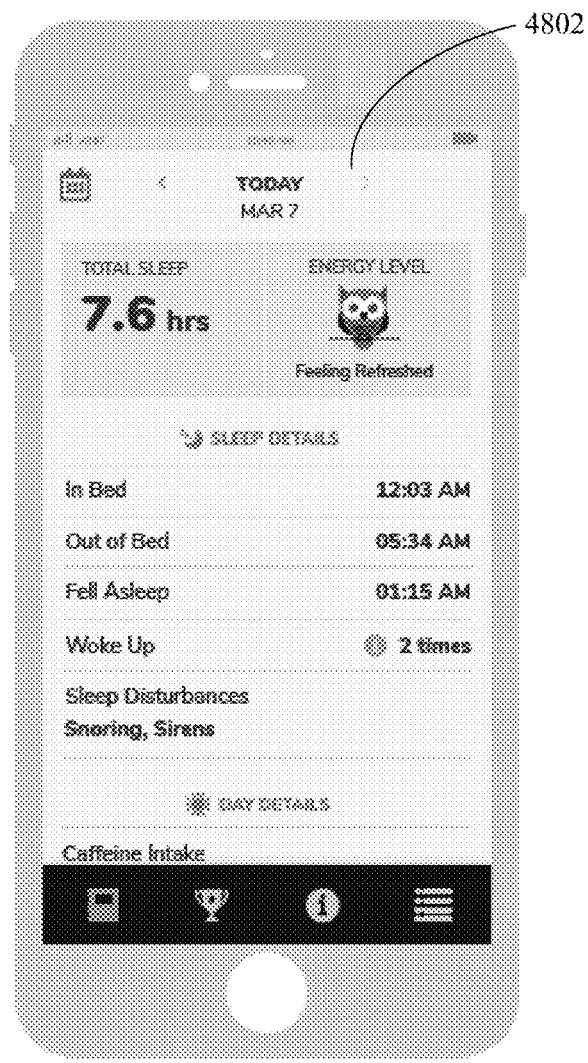
Figure 49:
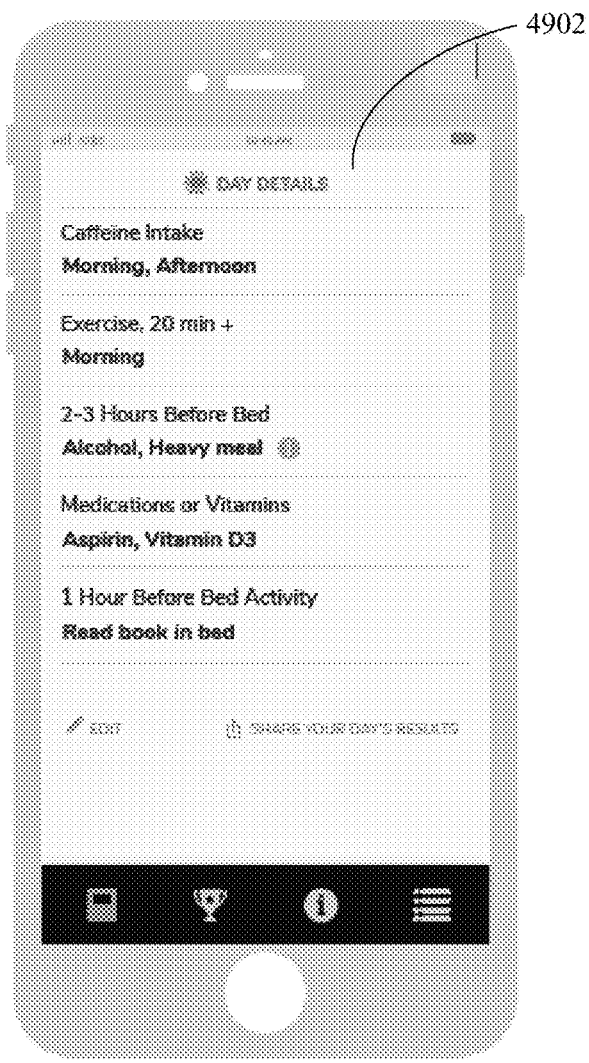

FIGS. 48 and 49 show screens that summarize sleep log details of the patient for a particular day. Screen 4802 shown in FIG. 48 shows the total duration of sleep, the patient's energy level following the previous night sleep, the time the patient was in bed, out of bed, and fell asleep, and any sleep disturbances (e.g., snoring, sirens). Screen 4902 shown in FIG. 49 is a continuation of screen 4802 shown in FIG. 48. Screen 4902 summarizes the patient's caffeine intake, amount of exercise, food and drink consumption prior to bedtime, medications or vitamins, and patient activities one hour prior to bedtime (e.g., reading a book, watching the TV).

Figure 50:
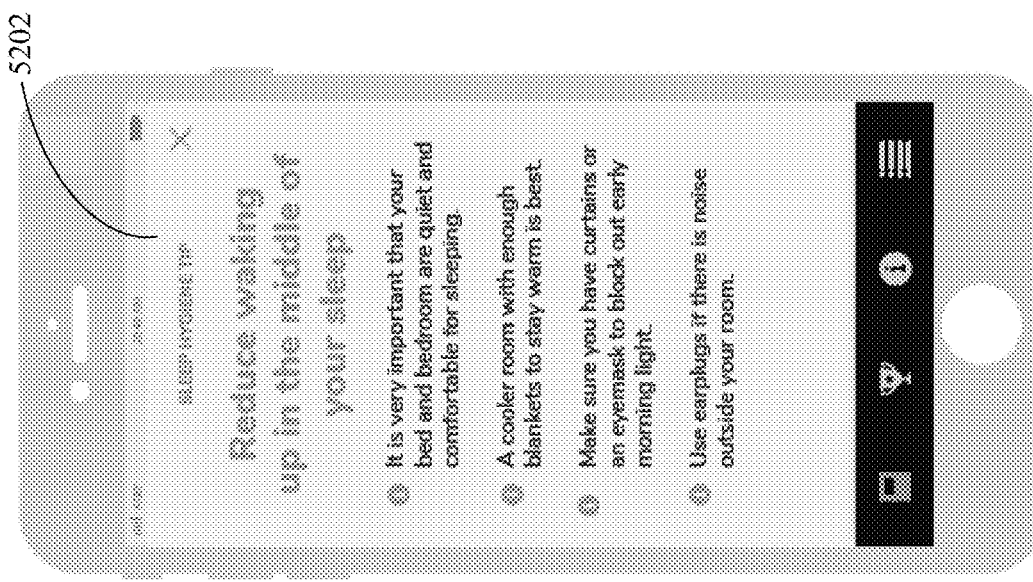
Figure 51:
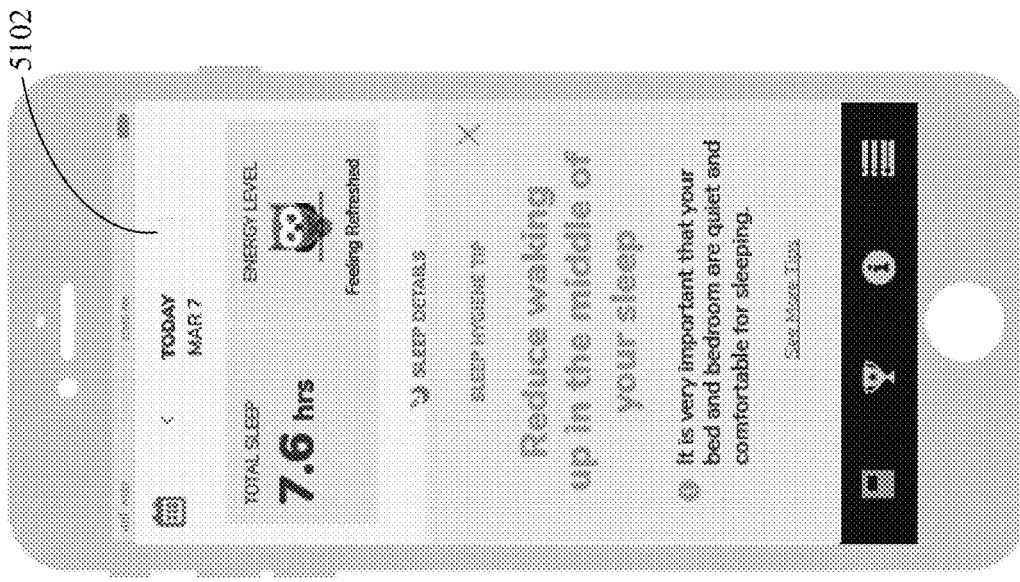
Figure 52:
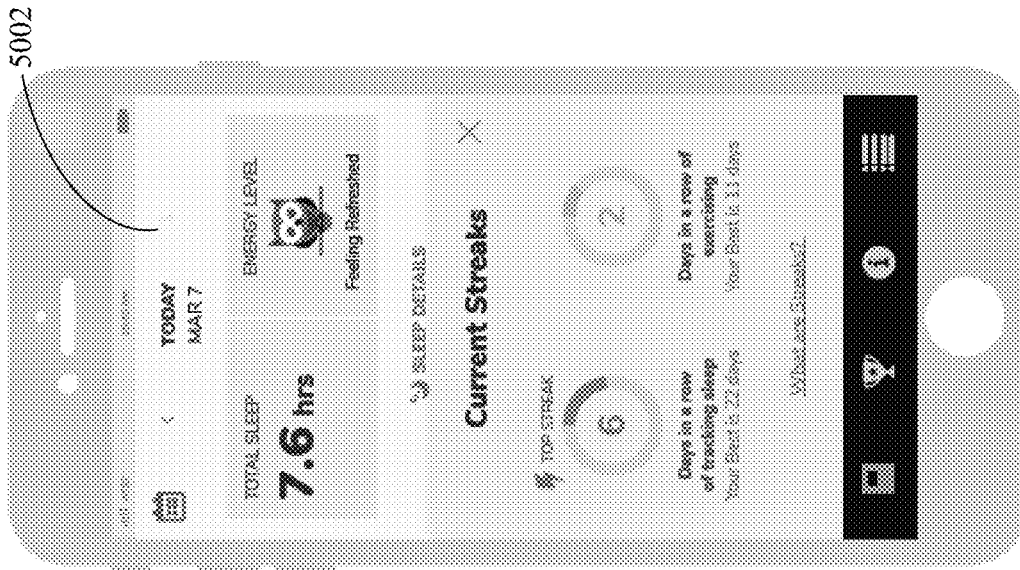
Figure 54:
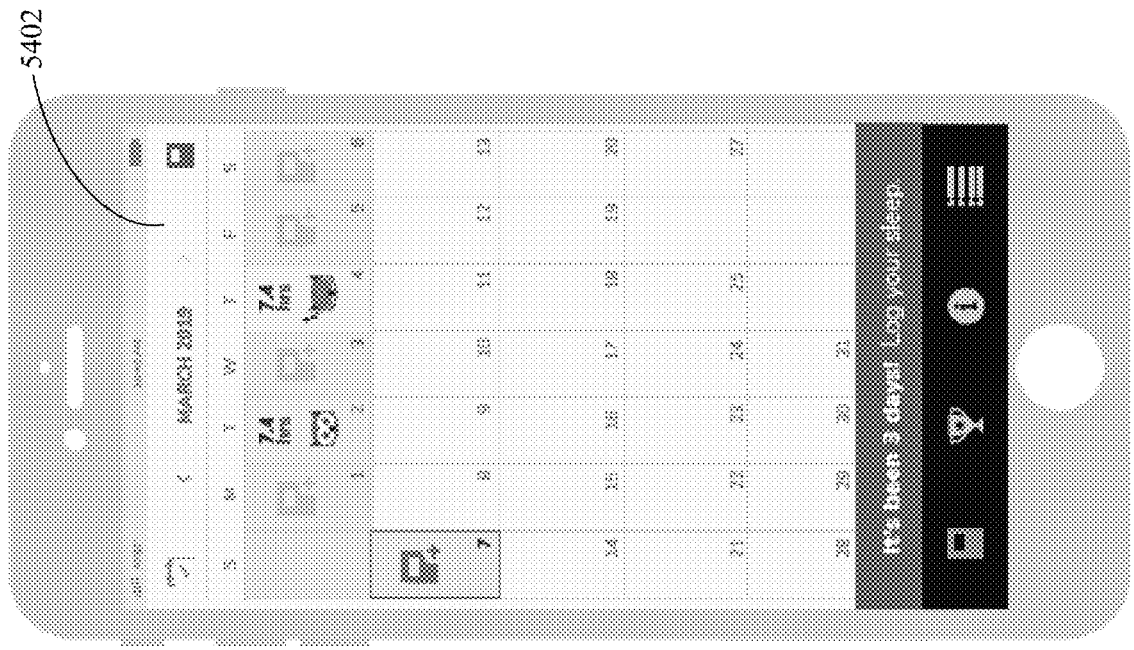

FIGS. 50-52 show screens that present additional sleep details to the patient. Screen 5002 shown in FIG. 50 shows the patient's achievements in addition to total sleep and energy level. For example, patient achievement can be presented in terms of current streaks, such as the number of consecutive days in which the patient tracked his or her sleep and the number of consecutive days in which the patient exercised. Presentation of patient achievement information provides motivation for improved patient sleeping habits. FIGS. 51 and 52 show sleep hygiene tips in addition to total sleep and energy level information. The sleep hygiene tips provide information concerning the patient's sleep environment which can significantly improve the patient's quality of sleep. The sleep hygiene tips can provide information concerning bedroom quietness and comfort, bedroom temperature, and ambient light levels in the bedroom.

Figure 53:
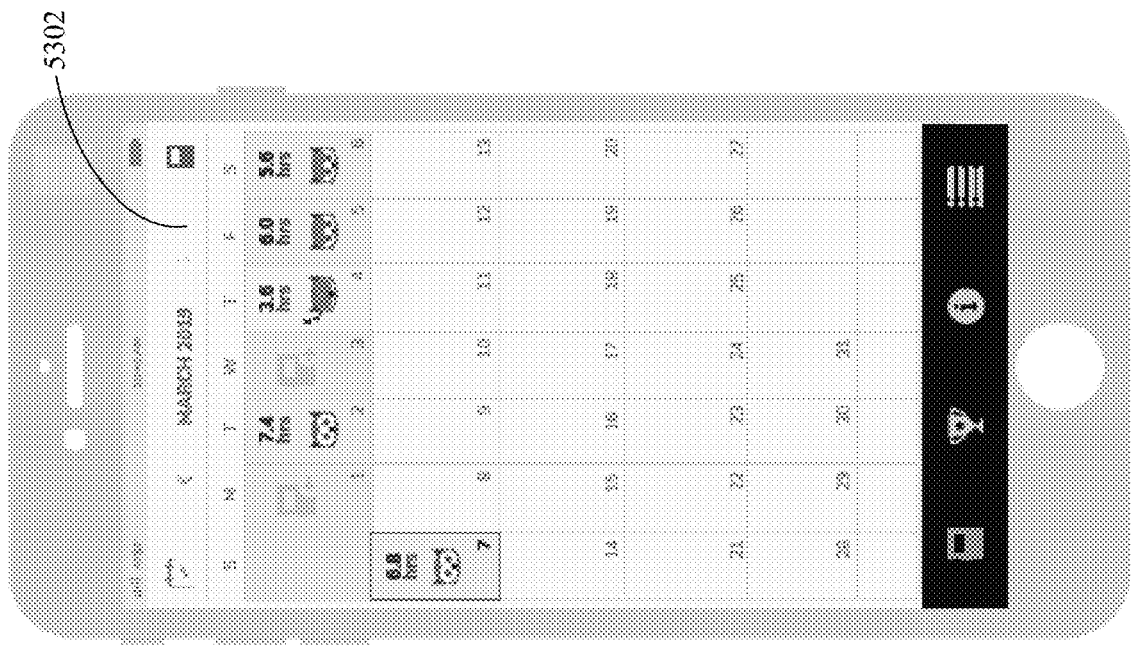

Screen 5302 shown in FIG. 53 provides a monthly calendar view of the patient's sleep details. As shown, a graphic showing the total sleep duration and energy level of the patient is presented for each day of the month. Additional sleep details are provided by clicking on any one of the days of the month. Screen 5402 shown in FIG. 54 includes a number of days of the month in which no sleep log information has been input. The mobile app can be programmed to remind the patient to enter sleep log information when a specified number of days (e.g., 1, 2, or 3) of sleep log information is missing. In the example shown in FIG. 54, the screen 5402 presents a reminder to the patient that it has been three days since sleep log data has been input.

Figure 55:
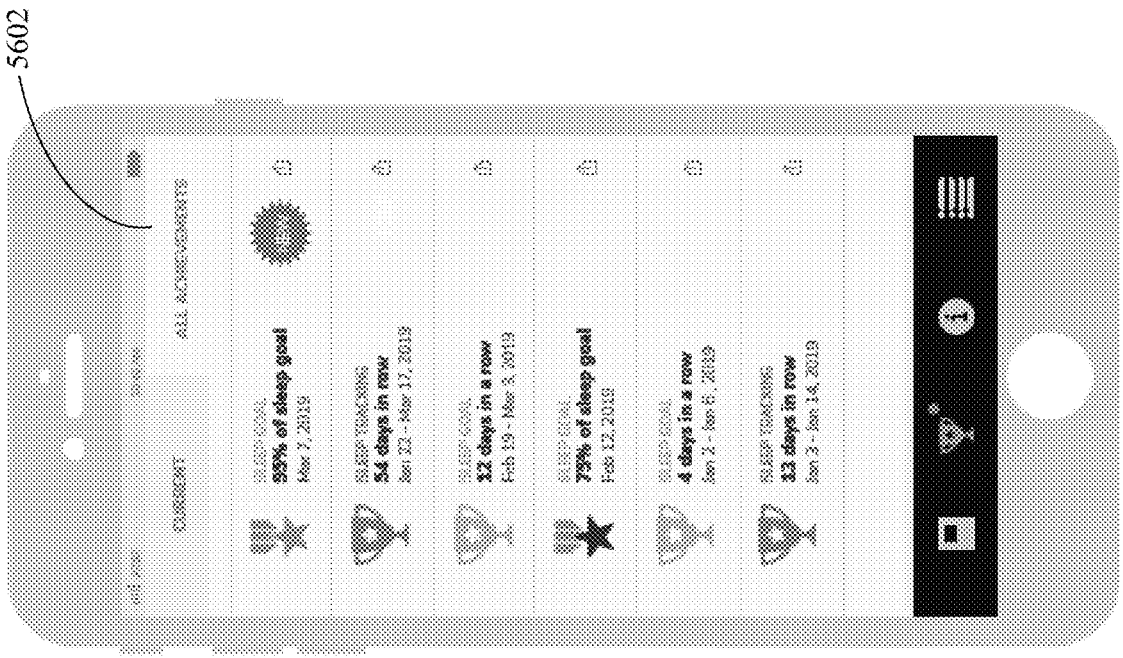
Figure 56:
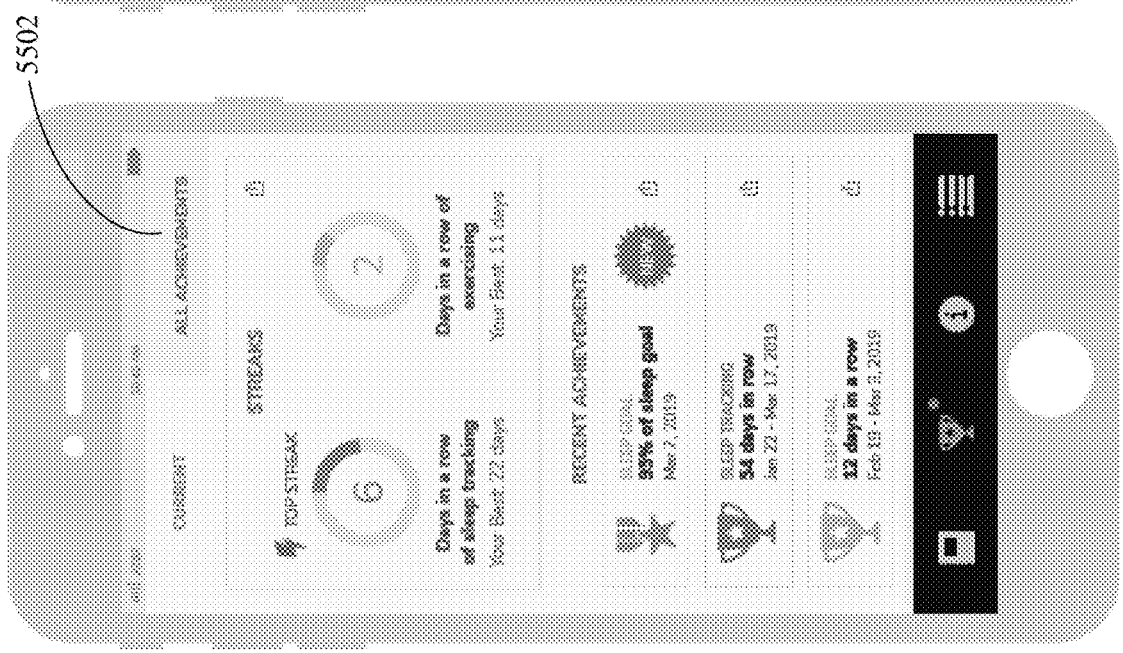

FIGS. 55 and 56 show screens that present achievement information to the patient. Screens 5502 and 5602 shown in FIGS. 55 and 56 allow the patient to view current and all streaks and achievements. For example, the streaks can include the consecutive number of days in which the patient entered sleep log information and participated in exercise. The achievements can include the percentage of achieving a sleep goal, the number of days in which sleep was logged by the patient, and the number of days in which a predefined sleep goal was achieved.

Figure 59:
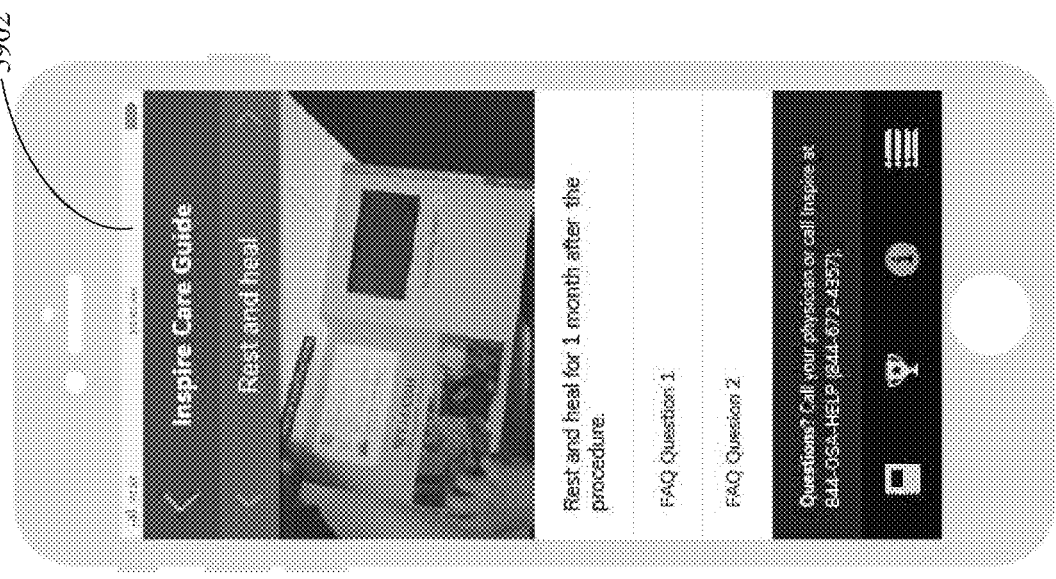
Figure 58:
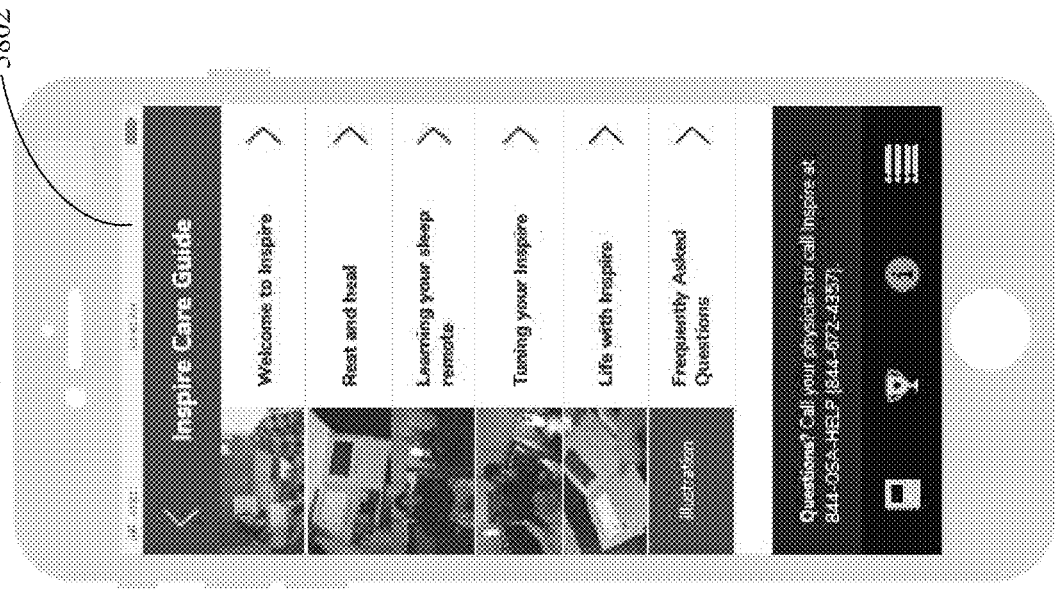
Figure 57:
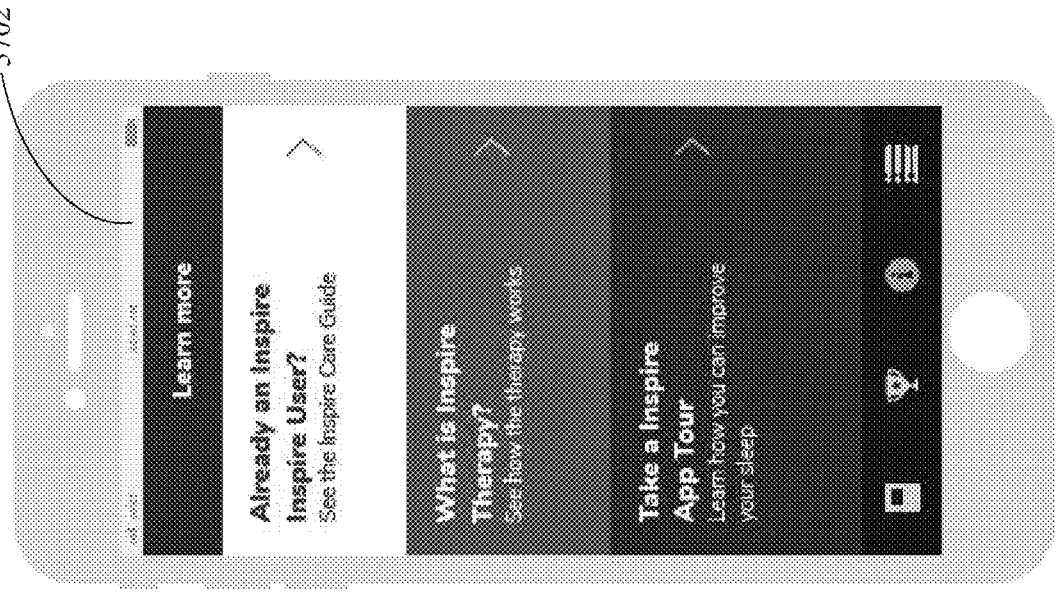

FIGS. 57-61 show screens that provide various types of educational information to the patient in response to activating the Therapy and Device Education screen 539 shown in FIG. 5. Screen 5702 shown in FIG. 57 allows the patient to view a care guide for the therapy device, information on how the therapy works, and information on how the patient can improve his or her sleep. Screen 5802 shown in FIG. 58 shows details of a care guide, which includes information concerning the use of a patient remote and how to tune the therapy device and/or therapy delivered by the device, and provides answers to frequently asked questions, among other information. Screen 5902 shown in FIG. 59 shows information concerning rest and healing after implant of the therapy device, which can be activated by the button shown on screen 5802 of FIG. 58.

Figure 60:
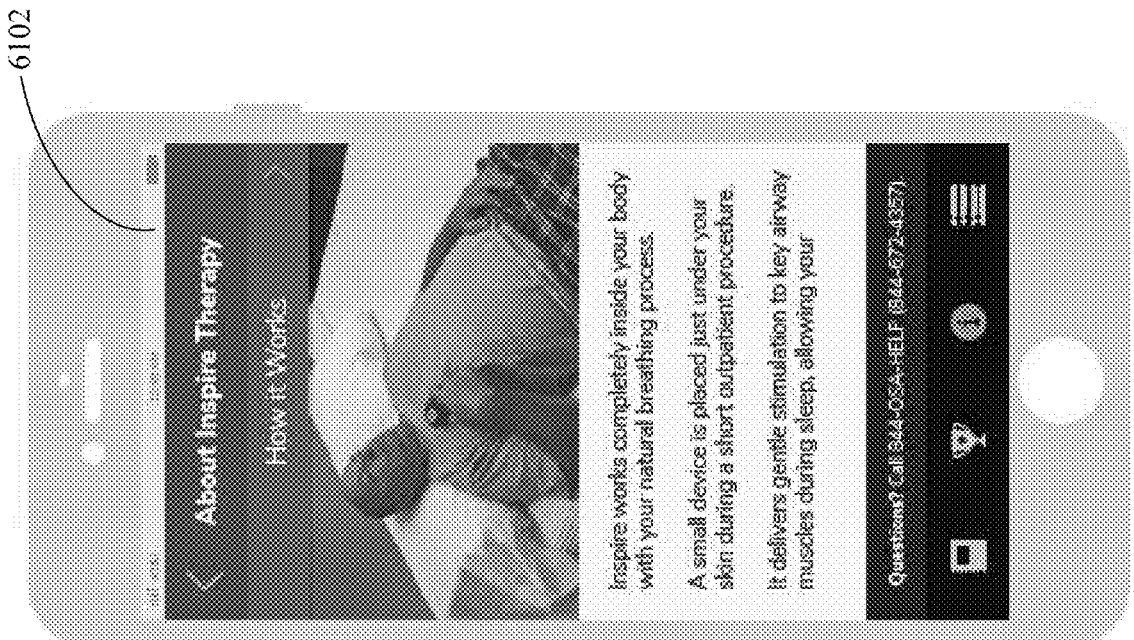
Figure 61:
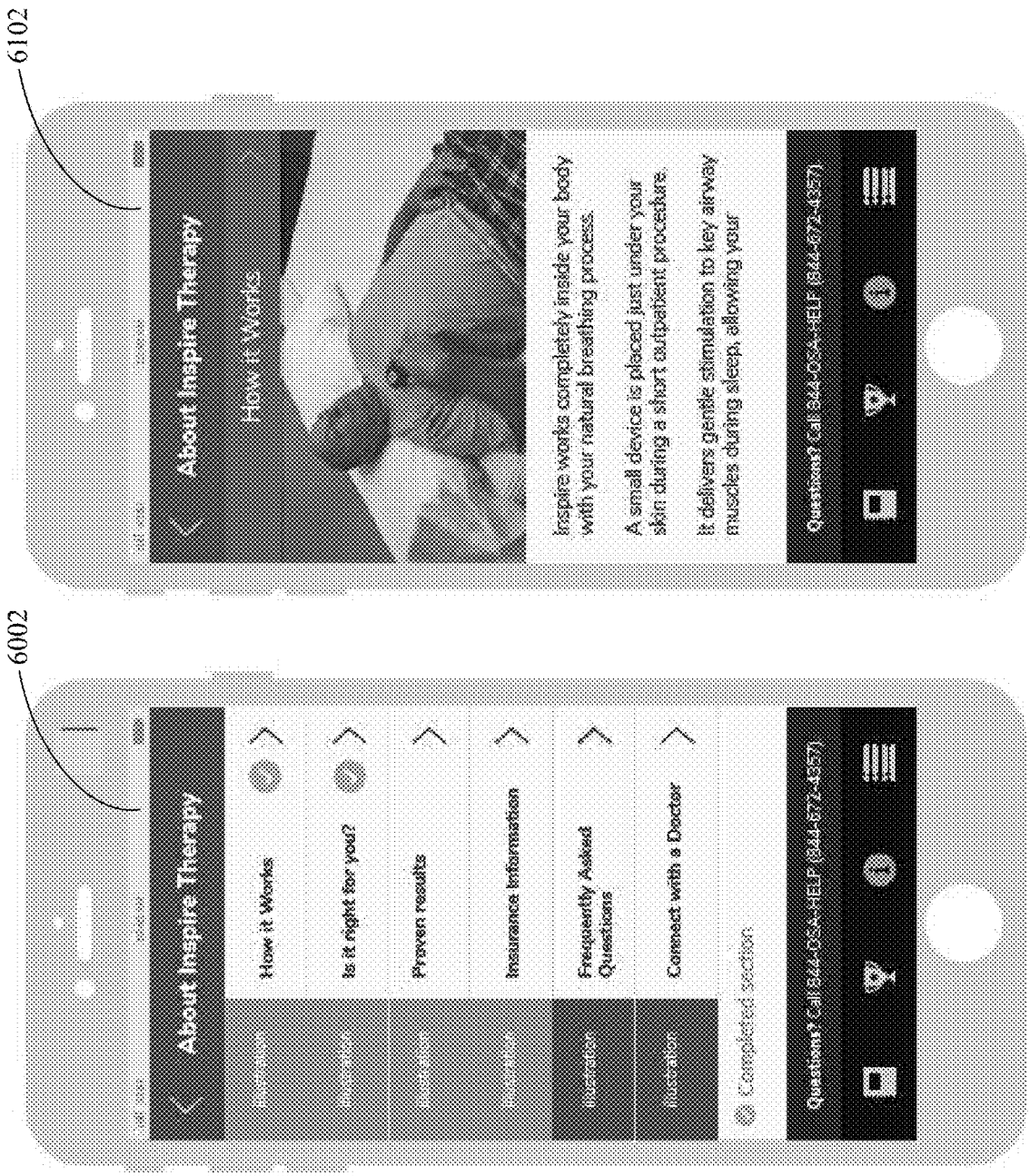

Screen 6002 shown in FIG. 60 provides the patient with detailed information concerning how therapy delivered by the therapy device works and proven results. Screen 6002 also provides insurance information, answers to frequently asked questions, and information on connecting with a doctor (e.g., the patient's doctor or a doctor knowledgeable about the therapy device). Screen 6102 shown in FIG. 61 provides additional details on how the therapy works, which can be activated by the corresponding button shown on screen 6002 of FIG. 60.

Figure 62:
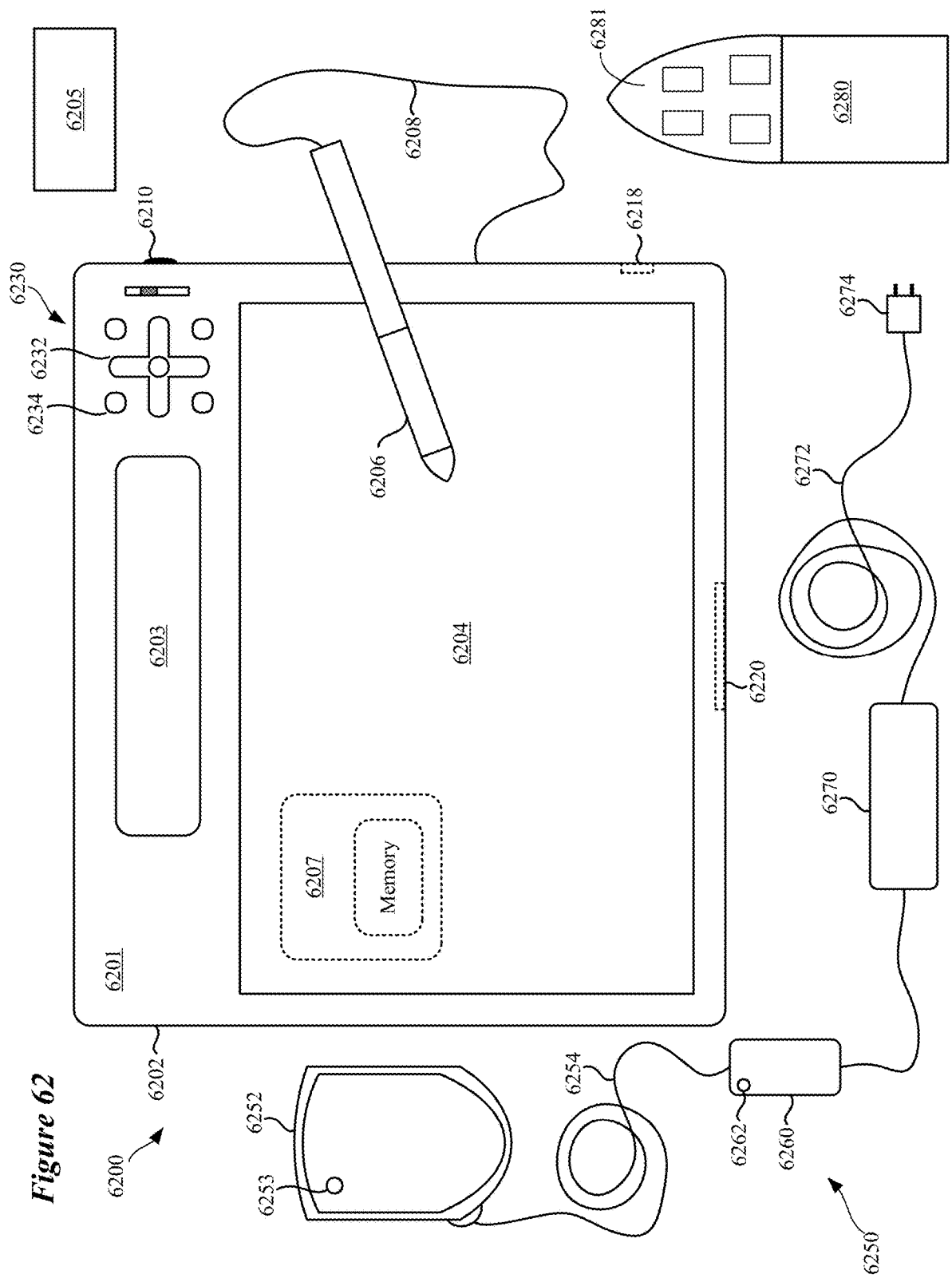
FIG. 62 shows a representative wireless programmer configured to communicate with an implantable therapy device in accordance with various embodiments.

FIG. 62 shows a medical system/device that can be used to generate patient medical data which can be uploaded to a remote server in accordance with various embodiments. FIG. 62 shows a wireless programmer 6202 configured to communicate with a patient medical device 6205 via a telemetry cable 6250. According to various embodiments, the wireless programmer 6202 can be implemented as a tablet computer or other mobile computing device (e.g., a phablet, notebook or laptop). The wireless programmer 6202 is configured to implement an application (app) or a browser that facilitates clinician interaction with the telemetry cable 6250 and the patient medical device 6205. In some embodiments, the patient medical device 6205 is a neurostimulation device configured to deliver a neurostimulation therapy for treating an obstructive disordered breathing condition of the patient. In such embodiments, the neurostimulation device 6205 includes a neurostimulator and a stimulation lead that extends from the housing of the neurostimulator to the hypoglossal nerve in the patient's neck. A sensing lead extends from the housing of the neurostimulator and is implanted at an intercostal muscle location of the rib cage. The sensing lead detects intercostal muscle movement during patient respiration, signals from which are used to detect patient respiration. A pulse generator in the neurostimulator provides electrical stimulation to the hypoglossal nerve via the stimulation lead based on detected patient respiration.

The wireless programmer 6202 can be used by a clinician to interrogate the patient medical device 6205 and make adjustments to various parameters (referred to as "programming"), monitor therapy delivered by the patient medical device 6205, and monitor patient adherence to prescribed therapy. FIG. 62 also shows a wireless patient remote 6280 configured to facilitate patient adjustment of one or more therapy settings of the patient medical device 6205 directly (i.e., without the need of programmer 6202).

The telemetry cable 6250 communicates wirelessly with the patient medical device 6205 and facilitates wireless communication between the patient medical device 6205 and the wireless programmer 6202. The wireless programmer 6202 includes a display 6204 and a stylus 6206 which allows the clinician to interact with the display 6204, such as by inputting, modifying, and reviewing data. In some embodiments, the display 6204 can be configured as a touchscreen, in which case the stylus 6206 may be excluded or an optional accessory. The wireless programmer 6202 includes a number of interfaces, buttons, and controls, several of which are shown in the illustrative embodiment of FIG. 62. A power button 6210 is provided on an upper right edge of the housing 6201, and a cluster of controls 6230 is provided on an upper right portion of the front surface of the housing 6202. The control cluster 6230 includes a multi-position control 6232 that allows the clinician to interact with a processor 6207 and display 6204 of the programmer 6202 in various ways. The processor 6207 of the programmer 6202 can be programmed to implement the various processes and functions described herein. Additional buttons 6234 can be situated proximate (or apart from) the control cluster 6230. The wireless programmer 6202 includes a number of different interfaces/components including a power connector plus USB port 6218 and a network cable and USB port 6220. The interfaces and components listed above are for purposes of illustration, not of limitation.

The telemetry cable 6250 is configured to wirelessly communicate with both the wireless programmer 6202 and the patient medical device 6205. The telemetry cable 6250 effectively serves as a wireless bridge or modem between the programmer 6202 and the patient medical device 6205. In accordance with the embodiment shown in FIG. 62, the telemetry cable 6250 includes a telemetry head 6252 configured to wirelessly communicate with the patient medical device 6205 via a near-field link. The telemetry head 6252 is shown to include a status indicator 6253, such as an LED indicator. In some embodiments, the telemetry head 6252 is configured to inductively communicate with the patient medical device 6205 via a near-field link.

A cable 6254 extends from the telemetry head 6252 and is connected to a wireless transceiver 6260. The wireless transceiver 6260 may be configured for short-range radio frequency (RF) communication. For example, the wireless transceiver 6260 may be configured to implement a short-range RF communication link, such as by implementing a Bluetooth® or ZigBee® communications protocol. In some embodiments, the wireless transceiver 6260 can be configured to wirelessly communicate with existing network infrastructure via an appropriate RF communication protocol, such as Wi-Fi®. The wireless transceiver 6260 is shown to include a status indicator 6262. Power is supplied to the telemetry cable 6250 by way of a power supply 6270, which is shown to include a power cable 6272 terminated by a standard AC wall plug 6274. The power supply 6270 provides power for both the wireless transceiver 6260 and the telemetry head 6252.

The patient remote 6280 (patient remote) is shown to include buttons to allow the patient to modify therapy parameters, and status indicators for implantable device status (e.g., remote and implantable device communication status and implantable device battery status) and remote status (remote battery status). The patient remote 6280 is utilized by a patient during home use of the therapy and to make necessary adjustments of therapy parameters (e.g., stimulation amplitude) if needed or desired. The patient remote 6280 shown in FIG. 62 has a control panel 6281 which includes a number of user actuatable control buttons. The control buttons provided on the control panel 6281 allow the patient to turn therapy on and off, pause therapy, and allow the patient to adjust one or more parameters that affect the operation of the implantable medical device that is surgically implanted in the patient. For example, the control panel 6281 can include a therapy ON button and a therapy OFF button, which can be actuated to respectively turn on and off stimulation therapy by the patient. An increase control provided on the control panel 6281 allows the patient to increase stimulation strength within a range selected by the clinician. A decrease control provided on the control panel 6281 allows the patient to decrease the stimulation strength within a range pre-selected by the clinician.

The wireless programmer 6202, patient remote 6280, and patient medical device 6205 (e.g., a neurostimulator) can be implemented in accordance with commonly-owned U.S. Pat. No. 9,839,786 (Rondoni et al.) and U.S. Pat. Pub. No. 2016/0193468 (Rondoni et al.), each of which is incorporated herein by reference.

In this disclosure, reference is made to various processors. A processor as disclosed herein may be a single processor or multiple processors. A processor can be implemented as one or more of a multi-core processor, a digital signal processor (DSP), a microprocessor, a programmable controller, a general-purpose computer, a special-purpose computer, a hardware controller, a software controller, a combined hardware and software device, such as a programmable logic controller, a programmable logic device (e.g., FPGA, ASIC), a personal computer (PC), a main frame computer, a laptop, a notebook, a tablet, phablet or a personal digital assistant, such as a smartphone. A processor can include or be coupled to memory, such as RAM, SRAM, ROM, flash, SSD (solid-state drive), or a hard drive (HDD). A processor can be a component of a computing or communication device that cooperates with a communication interface (e.g., wired or wireless interface), a display (e.g., a touch screen), memory (RAM, ROM, flash, SSD, hard drive), and a user interface (e.g., keyboard, mouse, voice control interface, touch screen). A processor can include or be coupled to one or more communication interfaces, such as a wired and/or wireless interface (e.g., USB, FireWire®, Lightning®, GSM, CDMA, GPRS, HSDPA, Bluetooth®, ZigBee®, IEEE 802.11, ISO/IEEE 11073 compliant interface). A processor of the present disclosure can be programmed to execute program instructions or code (e.g., software, firmware) to cause the processor to perform the processes disclosed herein, such as those described with reference to the Figures.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof

What is claimed is:

1. A method, comprising:
   establishing communication between a therapy device implantable in a patient and a consumer electronic device operable by the patient;
   controlling, by the consumer electronic device, a predetermined set of therapy device functions in response to patient inputs to the consumer electronic device;
   transmitting therapy data from the therapy device to the consumer electronic device;

wherein the transmitted therapy data includes a date and time when therapy was delivered to the patient by the therapy device; and
presenting at least a portion of the transmitted therapy data on a display of the consumer electronic device.

2. The method of claim 1, wherein the predetermined set of therapy device functions comprises turning on the therapy device, turning off the therapy device, and pausing therapy delivery by the therapy device.

3. The method of claim 1, wherein the predetermined set of therapy device functions comprises adjusting an amplitude of therapy delivered by the therapy device.

4. The method of claim 1, wherein the therapy data comprises therapy utilization data.

5. The method of claim 4, wherein the therapy utilization data comprises a start delay and data indicating a date and time when therapy was delivered, therapy was paused, and therapy was turned off in response to patient inputs to the consumer electronic device.

6. The method of claim 1, wherein the therapy data comprises data indicating therapy settings programmed into the therapy device by the consumer electronic device and a clinician programmer.

7. The method of claim 6, wherein the therapy data comprises:
a predetermined range of therapy amplitudes programmed into the therapy device by a clinician; and
patient-selected therapy amplitudes programmed into the therapy device by the patient.

8. The method of claim 7, comprising presenting the predetermined range of therapy amplitudes and the patient-selected therapy amplitudes on the display.

9. The method of claim 1, comprising:
transmitting, to the consumer electronic device, physiologic data acquired from one or more sensors coupled to or positioned proximate the patient; and
presenting the therapy data and the physiologic data on the display.

10. The method of claim 1, comprising:
transmitting, to the consumer electronic device, diagnostic data acquired from the therapy device; and
presenting the therapy data and the diagnostic data on the display.

11. The method of claim 1, wherein:
the therapy data comprises therapy utilization data and a target therapy duration; and
presenting the therapy data comprises presenting the therapy utilization data and target therapy duration graphically in the form of a stacked bar graph on the display.

12. The method of claim 11, wherein the stacked bar graph has an open ring configuration.

13. The method of claim 1, wherein:
the therapy data comprises therapy utilization data and a target therapy duration;
the therapy utilization data comprises a start delay and data indicating a date and time when therapy was delivered, therapy was paused, and therapy was turned off in response to patient inputs to the consumer electronic device; and
presenting the therapy data comprises presenting, on the display, the target therapy duration and, in temporal order and in proportion to duration, the start delay, the therapy delivered, the therapy paused, and the therapy turned off in the form of a stacked bar graph.

14. The method of claim 13, wherein the stacked bar graph has an open ring configuration.

15. The method of claim 13, comprising:
transmitting, to the consumer electronic device, physiologic data acquired from one or more sensors coupled to or positioned proximate the patient; and
presenting, on the display and in temporal alignment with the therapy utilization data, the physiologic data as a stacked bar graph having an open ring configuration positioned within or outside of the therapy utilization data, wherein the physiologic data is presented as bars having a size proportional to a magnitude of the physiologic data.

16. The method of claim 15, wherein:
the therapy device comprises a neurostimulation device configured to deliver a neurostimulation therapy for treating an obstructive disordered breathing condition; and
the physiologic data comprises snoring data.

17. The method of claim 16, wherein the sensor configured to produce the snoring data comprises a microphone of the consumer electronic device.

18. The method of claim 17, wherein the snoring data is presented as bars corresponding to quiet, light, heavy, and loud snoring.

19. The method of claim 1, wherein the therapy device comprises a neurostimulation device configured to deliver a neurostimulation therapy for treating an obstructive disordered breathing condition.

20. The method of claim 1, comprising:
generating patient-subjective information in response to patient inputs to the consumer electronic device; and
presenting the patient-subjective information on the display.

21. The method of claim 20, wherein the patient-subject information comprises a score calculated by the consumer electronic device in response to patient answers to a medical questionnaire.

22. The method of claim 20, wherein:
the patient-subjective information comprises sleep log information; and
the sleep log information is input to the consumer electronic device by the patient.

23. The method of claim 1, comprising:
acquiring patient-objective sleep log data automatically using one or more environmental sensors of the consumer electronic device; and
presenting the patient-objective sleep log data on the display.

24. The method of claim 1, comprising:
transmitting the therapy data from the consumer electronic device to a remote server; and
presenting the therapy data on a display coupled to the remote server.

25. A system, comprising:
a therapy device configured to be implanted in a patient;
a consumer electronic device operable by the patient, the consumer electronic device configured to control a predetermined set of therapy device functions in response to patient inputs to the consumer electronic device, the consumer electronic device further configured to:
receive therapy data transmitted from the therapy device;
wherein the received therapy data includes data indicating a date and time when therapy was delivered to the patient by the therapy device; and
present at least a portion of the therapy data on a display of the consumer electronic device.

26. The system of claim 25, wherein the predetermined set of therapy device functions comprises turning on the therapy device, turning off the therapy device, and pausing therapy delivery by the therapy device.

27. The system of claim 25, wherein the predetermined set of therapy device functions comprises adjusting an amplitude of therapy delivered by the therapy device.

28. The system of claim 25, wherein the therapy data comprises therapy utilization data.

29. The method of claim 1, wherein the consumer electronic device is a device not subject to medical regulatory body approval.

30. The method of claim 1, comprising:
prior to the step of establishing, loading an app onto the consumer electronic device;
wherein the step of establishing communication includes a processor of the consumer electronic device executing program code of the app.

31. The method of claim 1, wherein the consumer electronic device is a smartphone.

32. The method of claim 1, wherein the step of transmitting therapy data includes:
transmitting therapy data from the therapy device to a patient remote device apart from the consumer electronic device; and
transmitting the therapy data received at the patient remote device from the patient remote device to the consumer electronic device.

33. The method of claim 32, further comprising:
operating, by the patient, the patient remote to cause the therapy device to pause therapy currently being delivered to the patient.

34. The method of claim 1, wherein the step of transmitting includes:
prompting the patient, via a visual display on the consumer electronic device, to actively initiate an upload of the therapy data to the consumer electronic device.

* * * * *